(12) United States Patent
Dean et al.

(10) Patent No.: US 10,599,154 B2
(45) Date of Patent: *Mar. 24, 2020

(54) METHOD FOR ACCURATE OBJECT DETECTION WITH MULTIPLE SENSORS

(71) Applicant: Patroness, LLC, Nashville, TN (US)

(72) Inventors: Jered Harvey Dean, Arvada, CO (US); Barry George Dean, Franklin, TN (US); Dan Alan Preston, Bainbridge Island, WA (US)

(73) Assignee: Patroness, LLC, Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/434,000

(22) Filed: Jun. 6, 2019

(65) Prior Publication Data

US 2019/0310647 A1  Oct. 10, 2019

Related U.S. Application Data

(63) Continuation of application No. 15/880,699, filed on Jan. 26, 2018.
(Continued)

(51) Int. Cl.
*G05D 1/02* (2020.01)
*A61G 5/04* (2013.01)
(Continued)

(52) U.S. Cl.
CPC ............ *G05D 1/0219* (2013.01); *A61G 5/04* (2013.01); *A61G 5/042* (2013.01); *G05D 1/0225* (2013.01); *G05D 1/0244* (2013.01); *G05D 1/0246* (2013.01); *G05D 1/0255* (2013.01); *G05D 1/0257* (2013.01); *G05D 1/0274* (2013.01); *G05D 1/0278* (2013.01); *A61G 2203/40* (2013.01); *A61G 2203/72* (2013.01);
(Continued)

(58) Field of Classification Search
CPC .................. G05D 1/0219; G05D 1/72; G05D 2201/0206; G05D 1/0274; G05D 1/0246; G05D 1/0225; G05D 1/0278; G05D 1/0257; G05D 1/0255; G05D 1/0244; G16H 10/60; G16H 50/50; G16H 40/63; G16H 20/30; A61G 5/042; A61G 2203/40; A61G 2203/72; A61G 5/04
See application file for complete search history.

(56) References Cited

U.S. PATENT DOCUMENTS

| 5,654,907 | A | 8/1997 | Lange |
| 2003/0184729 | A1 | 10/2003 | Bowers |

(Continued)

OTHER PUBLICATIONS

PCT/US2018/046062 International Search Report and Written Opinion, 13 pages, dated Oct. 22, 2018.
(Continued)

*Primary Examiner* — Nadeem Odeh
*Assistant Examiner* — Michael V Kerrigan
(74) *Attorney, Agent, or Firm* — Polsinelli PC

(57) ABSTRACT

A system and method for providing safety for a motorized mobile system (MMS) are optimized for accurate object detection, the method comprising generating one or more of a range measurement and a bearing measurement to an object using at least two sensors, wherein the range and bearing measurements have associated uncertainties.

29 Claims, 36 Drawing Sheets

Related U.S. Application Data

(60) Provisional application No. 62/612,617, filed on Dec. 31, 2017, provisional application No. 62/543,896, filed on Aug. 10, 2017.

(51) Int. Cl.
  G16H 50/50 (2018.01)
  G16H 20/30 (2018.01)
  G16H 40/63 (2018.01)
  G16H 10/60 (2018.01)

(52) U.S. Cl.
  CPC ..... G05D 2201/0206 (2013.01); G16H 10/60 (2018.01); G16H 20/30 (2018.01); G16H 40/63 (2018.01); G16H 50/50 (2018.01)

(56) References Cited

U.S. PATENT DOCUMENTS

| | | | |
|---|---|---|---|
| 2005/0154503 | A1 | 7/2005 | Jacobs |
| 2008/0294300 | A1 | 11/2008 | Ashmore et al. |
| 2009/0292468 | A1* | 11/2009 | Wu .................. G01S 13/726 701/301 |
| 2010/0312461 | A1 | 12/2010 | Haynie et al. |
| 2011/0190972 | A1* | 8/2011 | Timmons ............ G01C 21/34 701/31.4 |
| 2014/0146167 | A1* | 5/2014 | Friend ............... G01S 17/023 348/118 |
| 2014/0165159 | A1 | 8/2014 | Baade et al. |
| 2015/0183431 | A1 | 7/2015 | Nanami |
| 2015/0346724 | A1 | 12/2015 | Jones et al. |
| 2017/0043771 | A1 | 2/2017 | Ibanez-Guzman et al. |

OTHER PUBLICATIONS

Surmann et al. "An autonomous mobile robot with a 3D laser range finder for 3D exploration and digitalization of indoor environments," Robotics and Autonomous Systems, Sep. 22, 2003, 18 pages; Retrieved from http://www2.inf.uni-osnabrueck.de/hertzberg/Papers/SurmannEtAIRAAS-2003.pdf.

ANSI/IEEE Std 802.2, "IEEE Standard for Information technology—Telecommunications and information exchange between systems—Local and metropolitan area networks—Specific requirements—Part 2: Logical Link Control", The Institute of Electrical and Electronics Engineers, Inc., New York, NY, USA, ISBN 1-55937-019-X, Dec. 31, 1989, 114 pages.

"Bluetooth Core Specification, v5.0", Bluetooth SIG, Inc., Dec. 6, 2016, 2822 pages, retrievable at https://www.bluetooth.org/en-us/specification/adopted-specifications.

ETSI European Standard EN 302 663 (V1.2.1), "Intelligent Transport Systems (ITS); Access layer specification for Intelligent Transport Systems operating in the 5 GHz frequency band", European Telecommunications Standards Institute, Sophia Antipolis, France, Reference REN/ITS-0040028, Jul. 2013, 24 pages.

ETSI Harmonized European Standard EN 302 571 (V1.2.1), "Intelligent Transport Systems (ITS); Radio commmunications equipment operating in the 5 855 MHz to 5 925 MHz frequency band; Harmonized EN covering the essential requirements of article 3.2 of the R&TTE Directive", European Telecommunications Standards Institute, Sophia Antipolis, France, Reference REN/ERM-TG37-009, Sep. 2013, 47 pages.

ETSI Technical Specification TS 102 687 (V1.1.1), "Intelligent Transport Systems (ITS); Decentralized Congestion control Mechanisms for Intelligent Transport Systems operating in the 5 GHz range; Access layer part", European Telecommunications Standards Institute, Sophia Antipolis, France, Reference DTS/ITS-0040014, Jul. 2011, 45 pages.

ETSI Technical Specification TS 102 792 (V1.2.1), "Intelligent Transport Systems (ITS); Mitigation techniques to avoid interference between European CEN Dedicated Short Range Communication (CEN DSRC) equipment and Intelligent Transport Systems (ITS) operating in the 5 GHz frequency range", European Telecommunications Standards Institute, Sophia Antipolis, France, Reference RTS/ITS-00438, Jun. 2015, 23 pages.

IEC Std. 61851-1:2017 "Electric vehicle conductive charging system—Part 1: General requirements", the International Electrotechnical Commission, Geneva, Switzerland, ISBN 978-2-8322-3766-3, Feb. 7, 2017, 292 pages.

IEEE Std. 802.11-2016, "IEEE Standard for Information technology—Telecommunications and information exchange between systems Local and metropolitan area networks—Specific requirements—Part 11: Wireless LAN Medium Access Control (MAC) and Physical Layer (PHY) Specifications", The Institute of Electrical and Electronics Engineers, Inc., New York, NY, USA, ISBN 978-1-5044-3645-8 STDPD22369, Dec. 14, 2016, 3534 pages.

IEEE Std. 802.15.1-2005, "Wireless medium access control (MAC) and physical layer (PHY) specifications for wireless personal area networks (WPANs)", The Institute of Electrical and Electronics Engineers, Inc., New York, NY, USA, ISBN 0-7381-4707-9 SH95323, Jun. 14, 2005, 600 pages.

IEEE Std. 802.15.4-2015, "IEEE Standard for Low-Rate Wireless Networks", The Institute of Electrical and Electronics Engineers, Inc., New York, NY, USA, ISBN 978-1-5044-0846-2 STDPD20893, Apr. 22, 2016, 708 pages.

IEEE Std. 802.15.4q-2016, "IEEE Standard for Low-Rate Wireless Networks Amendment 2: Ultra-Low Power Physical Layer", The Institute of Electrical and Electronics Engineers, Inc., New York, NY, USA, ISBN 978-1-5044-0782-3 STD20852, Apr. 29, 2016, 52 pages.

IEEE Std. 802.15.4t-2017, "IEEE Standard for Low-Rate Wireless Networks Amendment 4: Higher Rate (2 Mb/s) Physical (PHY) Layer", The Institute of Electrical and Electronics Engineers, Inc., New York, NY, USA, ISBN 978-0-1-5044-3933-6 STDPD22524, Apr. 14, 2017, 25 pages.

IEEE Std. 802.16-2012, "IEEE Standard for Air Interface for Broadband Wireless Access Systems", The Institute of Electrical and Electronics Engineers, Inc., New York, NY, USA, ISBN 978-0-7381-7291-0 STD97266, Aug. 17, 2012, 2544 pages.

IEEE Std. 802-2014, "IEEE Standard for Local and Metropolitan Area Networks: Overview and Architecture", The Institute of Electrical and Electronics Engineers, Inc., New York, NY, USA, ISBN 978-0-7381-9219-2 STD98723, Jun. 30, 2014, 74 pages.

IEEE Std. 1003.1-2008, "IEEE Standard for Information Technology—Portable Operating System Interface (POSIX)", The Institute of Electrical and Electronics Engineers, Inc., New York, NY, USA, ISBN 978-0-7381-5798-6 STD95820, Dec. 1, 2008, 3874 pages.

IEEE Std. 1609.0-2013, "IEEE Guide for Wireless Access in Vehicular Environments (WAVE)—Architecture", The Institute of Electrical and Electronics Engineers, Inc., New York, NY, USA, ISBN 978-0-7381-8756-3 STD98459, Mar. 5, 2014, 78 pages.

IEEE Std. 1609.2-2016, "IEEE Standard for Wireless Access in Vehicular Environments—Security Services for Applications and Management Messages", The Institute of Electrical and Electronics Engineers, Inc., New York, NY, USA, ISBN 978-1-5044-0767-0 STD20841, Mar. 1, 2016, 884 pages.

IEEE Std. 1609.4-2016, "IEEE Standard for Wireless Access in Vehicular Environments (WAVE)—Multi-Channel Operation", The Institute of Electrical and Electronics Engineers, Inc., New York, NY, USA, ISBN 978-1-5044-0761-8 STD20838, Mar. 21, 2016, 205 pages.

IEEE Std. 1609.11-2010, "IEEE Standard for Wireless Access in Vehicular Environments (WAVE)—Over-the-Air Electronic Payment Data Exchange Protocol for Intelligent Transportation Systems (ITS)", The Institute of Electrical and Electronics Engineers, Inc., New York, NY, USA, ISBN 978-0-7381-6501-1 STD97080, Jan. 9, 2011, 62 pages.

IEEE Std. 1609.12-2016, "IEEE Standard for Wireless Access in Vehicular Environments (WAVE)—Identifier Allocations", The Institute of Electrical and Electronics Engineers, Inc., New York, NY, USA, ISBN 978-1-5044-0765-6 STD20840, Mar. 11, 2016, 39 pages.

IEEE Std. 11073-20601-2014, "IEEE Health informatics—Personal health device communication—Part 20601: Application profile—Optimized Exchange Protocol", The Institute of Electrical and

(56) References Cited

OTHER PUBLICATIONS

Electronics Engineers, Inc., New York, NY, USA, ISBN 978-0-7381-9314-4 STD98793, Oct. 10, 2014, 253 pages.
ISO/IEC 7498-1:1994, "Information technology—Open Systems Interconnection—Basic Reference Model: The Basic Model", Geneva, Switzerland, Reference No. ISO/IEC 7498-1:1994(E), Nov. 15, 1994, 68 pages.
ISO/IEC Std. 15408-1:2009, 3rd Edition: "Information technology—Security techniques—Evaluation criteria for IT security—Part 1: Introduction and general model", The International Organization for Standardization and the International Electrotechnical Commission Joint Technical Committee, Geneva, Switzerland, Reference No. ISO/IEC 15408-1:2009(E), Dec. 15, 2009, 74 pages.
ISO/IEC Std. 15408-2:2008, 3rd Edition: "Information technology—Security techniques—Evaluation criteria for IT security—Part 2: Security functional components", the International Organization for Standardization and the International Electrotechnical Commission Joint Technical Committee, Geneva, Switzerland, Reference No. ISO/IEC 15408-2:2008(E), Aug. 15, 2008, 240 pages.
ISO/IEC Std. 15408-3:2008, 3rd Edition: "Information technology—Security techniques—Evaluation criteria for IT security—Part 3: Security assurance components", the International Organization for Standardization and the International Electrotechnical Commission Joint Technical Committee, Geneva, Switzerland, Reference No. ISO/IEC 15408-3:2008(E), Aug. 15, 2008, 188 pages.
ISO/IEC Std. 18092:2013, "Information technology—Telecommunications and information exchange between systems—Near Field Communication—Interface and Protocol (NFCIP-1)", the International Organization for Standardization and the International Electrotechnical Commission Joint Technical Committee, Geneva, Switzerland, Reference No. ISO/IEC 18092:2013(E), Mar. 15, 2013, 52 pages.
ISO/IEC Std. 18092:2013 Technical Corrigendum 1, "Information technology—Telecommunications and Information exchange between systems—Near Field Communication—Interface and Protocol (NFCIP-1)", the International Organization for Standardization and the International Electrotechnical Commission Joint Technical Committee, Geneva, Switzerland, Reference No. SO/IEC 18092:2013/Cor.1:2015(E), Jul. 15, 2015, 2 pages.
ITU-T Recommendation X.691 (2015), "Information technology—ASN.1 encoding rules: Specification of Packed Encoding Rules (PER)", International Telecommunication Union, Geneva, Switzerland, Aug. 2015, 74 pages.
SAE Std. J1772_201710, "SAE Electric Vehicle and Plug in Hybrid Electric Vehicle Conductive Charge Coupler", SAE International, Warrendale, Pennsylvania, USA, Oct. 13, 2017, 116 pages.
Office Action for U.S. Appl. No. 15/880,699, System and Methods for Sensor Integration in Support of Situational Awareness for a Motorized Mobile System, dated Aug. 8, 2019, 32 pages.
Office Action for U.S. Appl. No. 16/433,989, System and Methods for Sensor Integration in Support of Situational Awareness for a Motorized Mobile System, dated Aug. 8, 2019, 23 pages.

\* cited by examiner

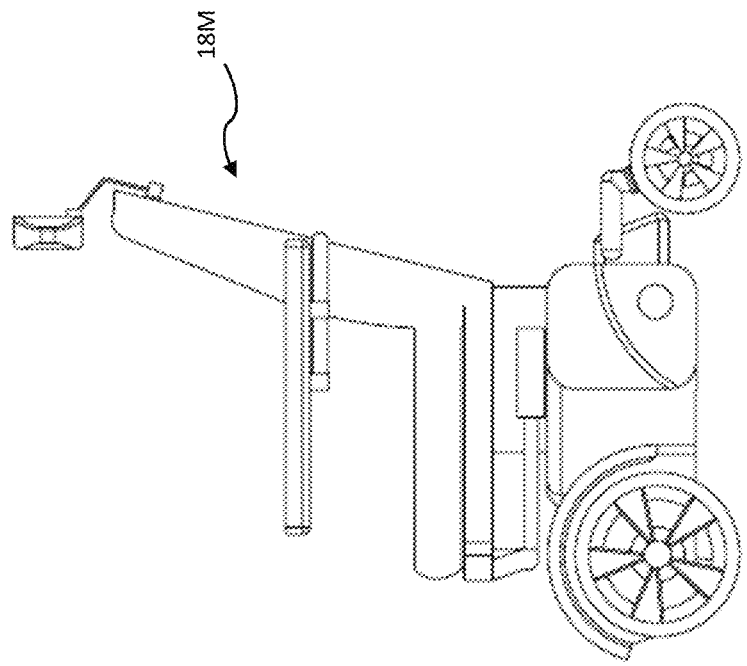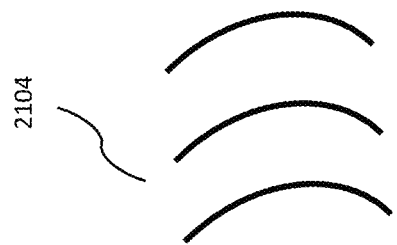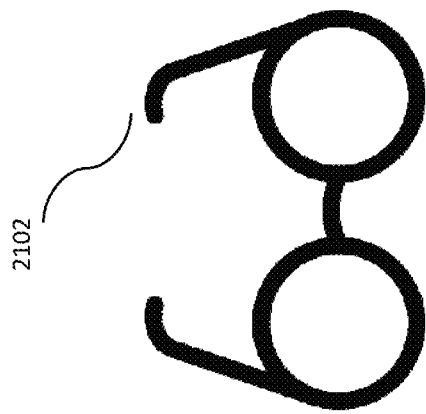
FIG. 21

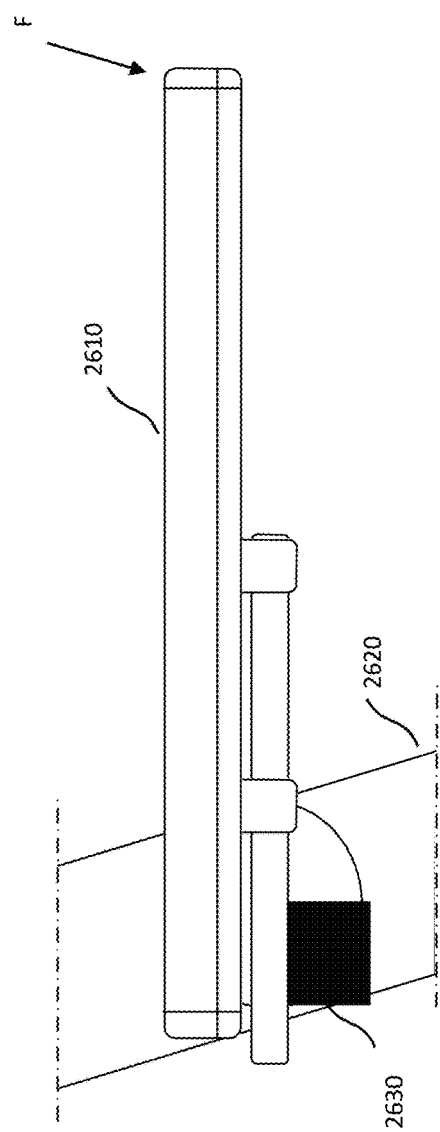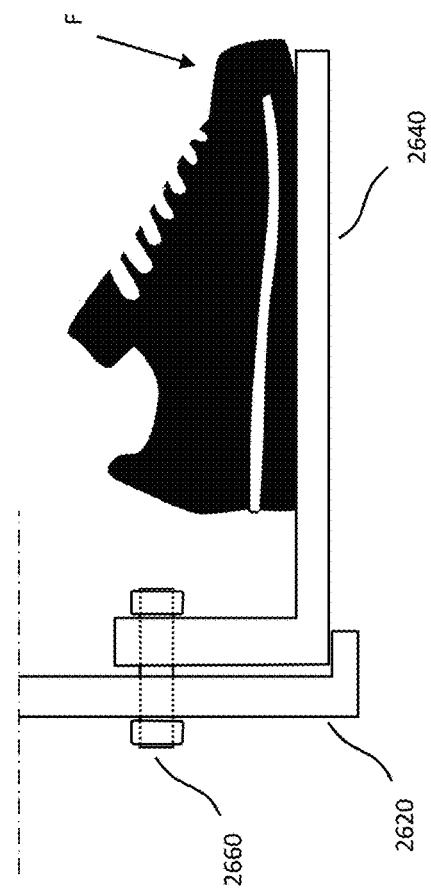

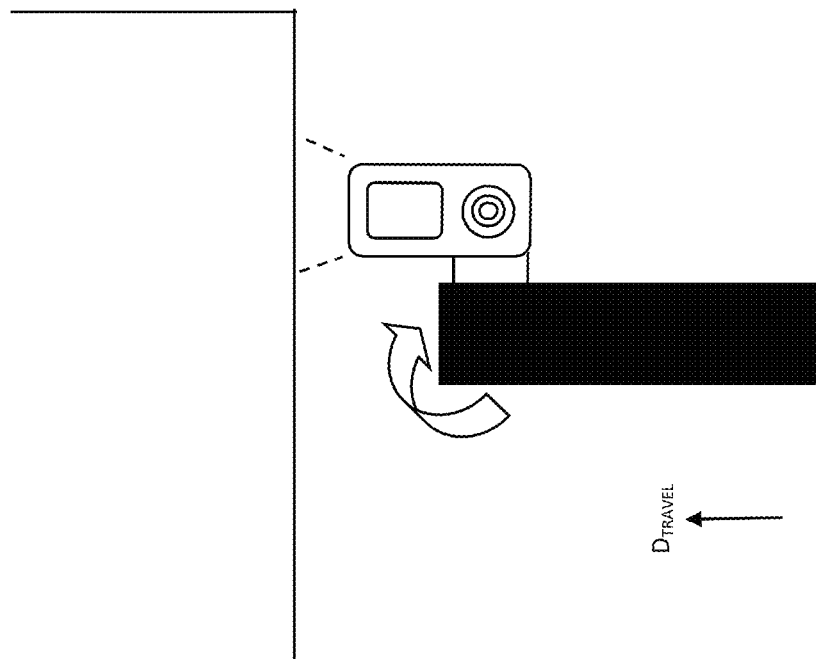
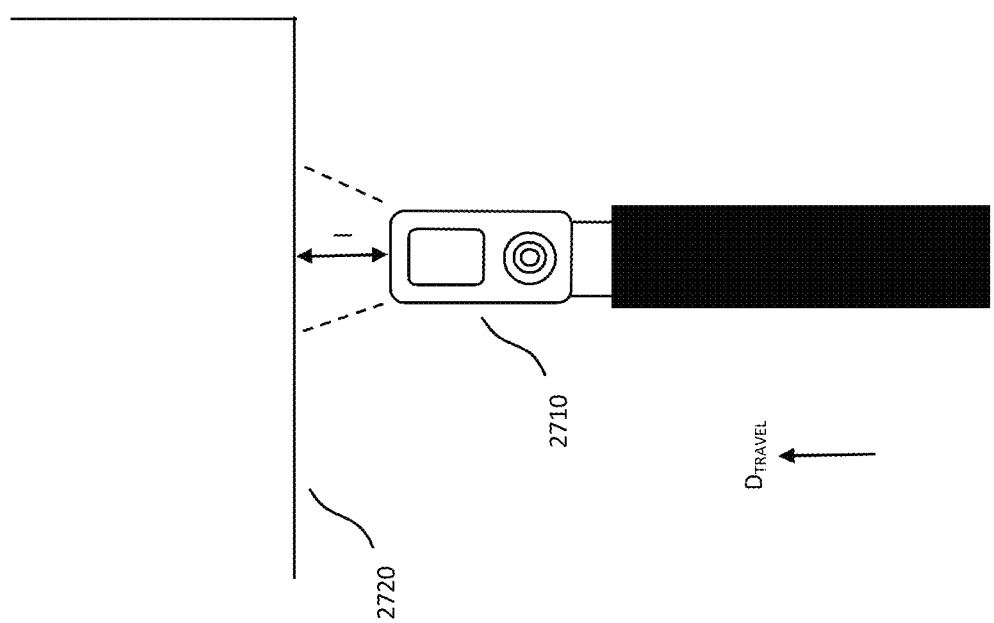
FIG. 27B
FIG. 27A

METHOD FOR ACCURATE OBJECT DETECTION WITH MULTIPLE SENSORS

RELATED APPLICATIONS

The present application is a continuation of U.S. patent application Ser. No. 15/880,699, entitled System and Methods for Sensor Integration in Support of Situational Awareness for a Motorized Mobile System, filed Jan. 26, 2018, which claims priority to U.S. Provisional Patent App. No. 62/543,896, entitled Systems and Methods for Motorized Mobile Systems, filed Aug. 10, 2017, and U.S. Provisional Patent App. No. 62/612,617, entitled Systems and Methods for Enhanced Autonomous Operations of a Motorized Mobile System, filed Dec. 31, 2017, which are incorporated herein by reference in their entirety. The present application is related to U.S. patent application Ser. No. 16/433,989, entitled System and Methods for Sensor Integration in Support of Situational Awareness for a Motorized Mobile System, filed on the same date as the present application, which is incorporated herein by reference in its entirety. The present application also is related to U.S. patent application Ser. No. 15/880,663, entitled Secure Systems Architecture for Integrated Motorized Mobile Systems, filed Jan. 26, 2018, U.S. patent application Ser. No. 15/880,686, entitled Federated Sensor Array for Use with a Motorized Mobile System and Method of Use, filed Jan. 26, 2018, all of which are incorporated herein by reference in their entirety.

INVENTORS

| | | | |
|---|---|---|---|
| Jered H. Dean | US Citizen | US Resident | Arvada, CO |
| Barry G. Dean | US Citizen | US Resident | Franklin, TN |
| Dan A. Preston | US Citizen | US Resident | Bainbridge Island, WA |

COPYRIGHT NOTICE

Contained herein is material that is subject to copyright protection. The copyright owner has no objection to the facsimile reproduction by anyone of the patent document or the patent disclosure, as it appears in the United States Patent and Trademark Office patent file or records, but otherwise reserves all rights to the copyright whatsoever. The following notice applies to the software, screenshots and data as described below and in the drawings hereto and All Rights Reserved.

FIELD

This disclosure relates generally to control systems and sensor systems for motorized mobile systems.

BACKGROUND

Drive-by-wire (DbW), steer-by-wire, or x-by-wire technology is the use of electrical or electro-mechanical systems for performing vehicle functions traditionally achieved by mechanical linkages. This technology replaces the traditional mechanical control systems with electronic control systems using electromechanical actuators and human-machine interfaces. The technology is similar to the fly-by-wire systems used in the aviation industry. Use of these "by-wire" systems began with manned aircraft, migrated to drones, as well as marine and rail operations, and are now being used in autonomous or self-driving vehicle applications. These once expensive technologies are emerging in the market as commodity products, including products with sensors, processors, integrated mobile devices, and various communication mediums, including bandwidth increases for soon to be $5^{th}$ generation (5G) wireless devices on 5G networks.

This application and co-pending applications will create and achieve safe, secure independence and a richer experience for all motorized mobile system (MMS) users. As an example of the need for improved MMSs, consider that today, with the advances in robotics and systems of systems integration, as well as medical advances that allow device integration with the human nervous system, there is a widening split between MMS users with varying physiological functionality. Some mobile chair users may have significant remaining upper body mobility and cognitive function. An example of this would be a person who does not have the use of their legs and who uses a manual mobile chair for mobility, but is otherwise able to navigate day-to-day life with minimal to no assistance. Such an individual may be able to adapt to an artificial limb, such as a leg, or an exoskeleton and reasonably be able to go about their day to day life with few restrictions. However, another example would be a user with certain health issues that greatly impacts the user's mobility and/or cognition. It is unlikely that these users will benefit from the same artificial leg or exoskeleton technologies due to their physiological condition. These users may use a motorized mobile system, such as a mobile chair.

Many mobile chair users report they are frequently frustrated by the general public's poor understanding of their abilities and needs. In general, the mobile chair is an extension of a user's body. People who use them have different disabilities and varying abilities. Some can use their arms and hands, while others can get out of their mobile chairs and walk for short distances. "Disability" is a general, medical term used for a functional limitation that interferes with a person's ability to walk, hear, learn, or utilize other physiological and/or cognitive functions of the body.

Conditions like cerebral palsy can be a sub-set of either physiological or cognitive disabilities since there are a number of sub-types classified based on specific ailments they present, resulting in varying degrees of ability. For example, those with stiff muscles have what is medically defined as spastic cerebral palsy, those with poor coordination have ataxic cerebral palsy, and those with writhing movements have athetoid cerebral palsy, each type requiring individual mobility plans.

Following are a few definitions used in this disclosure.

People with disabilities: This term represents a universe of potential conditions, including physical, cognitive, and/or sensory conditions.

Mobility disability: This term represents a condition for a person who uses a mobile chair or other MMS to assist in mobility.

User: This term refers to an individual who uses an MMS. A "user" of a mobile chair is referred to herein as a "mobile chair user".

Operator: This term refers to an individual who operates an MMS, including manual, local, and remote operation.

Caregiver: This term represents any individual that assists an MMS user. Family, friends, aides, and nurses may all be included in this category. The term "Attendant" is used synonymously with the term caregiver.

Technician: This term includes one or more of those individuals who setup, service, modify, or otherwise work technically on an MMS. These individuals may be formally licensed or may include operators and caregivers who are comfortable working with the system.

A mobile chair is essentially a chair with wheels used when walking is difficult or impossible due to illness, injury, or disability. Mobile chairs come in a wide variety to meet the specific needs of their users, including:

Manual self-propelled mobile chairs.
Manual attendant-propelled mobile chairs.
Powered mobile chairs (power-chairs).
Mobility scooters.
Single-arm drive mobile chairs.
Reclining mobile chairs.
Standing mobile chairs.
Combinations of the above.

Mobile Chairs include specialized seating adaptions and/or individualized controls and may be specific to particular activities. The most widely recognized distinction in mobile chairs is powered and unpowered. Unpowered mobile chairs are propelled manually by the user or attendant while powered mobile chairs are propelled using electric motors.

Motorized mobile chairs are useful for those unable to propel a manual mobile chair or who may need to use a mobile chair for distances or over terrain which would be fatiguing or impossible in a manual mobile chair. They may also be used not just by people with 'traditional' mobility impairments, but also by people with cardiovascular and fatigue-based conditions. A Motorized Mobile System (MMS) is a non-automobile motorized device which provides powered mobility to one or more users, including such systems as powered mobile chairs, mobility scooters, electronic conveyance vehicles, riding lawn mowers, grocery carts, all-terrain vehicles (ATVs), golf carts, and other recreational and/or medical mobility systems, but excludes automobiles (passenger cars, trucks, passenger buses, and other passenger or property transporting motorized vehicles intended for licensed operation on state and national highways). For the sake of clarity, a mobile chair MMS is described herein as an exemplary embodiment; however, it should be clear that the same or similar systems and methods may be applied to other MMS embodiments.

A mobile chair MMS is generally four-wheeled or six-wheeled and non-folding. Four general styles of mobile chair MMS drive systems exist: front, center, rear, and all-wheel drive. Powered wheels are typically somewhat larger than the trailing/castering wheels, while castering wheels on a motorized chair are typically larger than the casters on a manual chair. Center wheel drive mobile chair MMSs have casters at both front and rear for a six-wheel layout and are often favored for their tight turning radii. Front wheel drive mobile chair MMSs are often used because of their superior curb-climbing capabilities. Power-chair chassis may also mount a specific curb-climber, a powered device to lift the front wheels over a curb of 10 cm or less.

Mobile chair MMSs are most commonly controlled by arm-rest mounted joysticks which may have additional controls to allow the user to tailor sensitivity or access multiple control modes, including modes for the seating system. For users who are unable to use a hand controller, various alternatives are available, such as sip-and-puff controllers, worked by blowing into a sensor. In some cases, a controller may be mounted for use by an aide walking behind the chair rather than by the user. Capabilities include turning one drive-wheel forward while the other goes backward, thus turning the mobile chair within its own length.

The seating system on a mobile chair MMS can vary in design, including a basic sling seat and backrest, optional padding, comfortable cushions, backrest options, and headrests. Many companies produce aftermarket seat, back, leg, and head rest options which can be fitted onto mobile chair MMSs. Some seat, back, leg, and head rests are produced to aid with increased need for stability in the trunk or for those at increased risk of pressure sores from sitting. Leg rests may be integrated into the seating design and may include manual and/or powered adjustment for those users who want or need to vary their leg position. Mobile chair MMSs may also have a tilt-in-space, or reclining facility, which is particularly useful for users who are unable to maintain an upright seating position indefinitely. This function can also help with comfort by shifting pressure to different areas over time, or with positioning in a mobile chair when a user needs to get out of the chair or be hoisted.

Most mobile chairs are crash tested to ISO standards 7176 and 10542. These standards mean that a mobile chair can be used facing forward in a vehicle if the vehicle has been fitted with an approved tie down or docking system for securing the mobile chair and a method of securing the occupant to the mobile chair.

Rehabilitation engineering is the systematic application of engineering sciences to design, develop, adapt, test, evaluate, apply, and distribute technological solutions to problems confronted by individuals with disabilities. Current practitioners of rehabilitation engineering are often forced to work with limited information and make long term decisions about the technologies to be used by an individual on the basis of a single evaluation; a snapshot in time. Under current best-case conditions, rehabilitation engineering practitioners work closely in a long-term relationship with their clients to follow-up and readjust assistive technology systems on a regular basis. However, even in these situations, they are often working with limited information and only at periodic intervals.

What is needed is an evolution of existing motorized mobile systems (MMSs) to consider the users' abilities, needs, and health, with the goal of a safe, secure, and social independence. To accomplish this, systems and methods are disclosed herein comprising: integrated software and hardware systems, sensors for situational awareness, sensors for user monitoring, communications between users and caregivers, users and other users, and users and the "cloud", and human machine interfaces (HMIs) designed for users with a variety of physiological and cognitive conditions. The systems and methods disclosed herein are based on new underlying technologies, architectures, and network topologies that support the evolution of the MMS.

SUMMARY

Four co-pending-applications disclose various aspects of improved MMSs. All four are disclosed as related above and each incorporates by reference herein in the entirety of the other applications in full.

The application entitled "Secure Systems Architecture for Motorized Mobile Systems," relates to systems and methods for implementing a control system onboard an MMS capable of securely communicating with and utilizing external systems. This may include integrating external devices and user health monitoring sensors with an off the shelf (OTS) or custom MMS. Integration of a smart device, such as a smart phone or tablet, with an OTS or custom MMS is another example. Today, most smart devices contain a host of applications and sensors, including one or more of image capturing devices, rate and acceleration sensors, gyroscopes, global positioning system (GPS) receivers, biometric sensors, iris scanners, fingerprint scanners, and facial recognition software. Other sensors are possible. A secure architecture for an MMS controller is disclosed in support of device integration and data security with a focus on extensibility.

The application entitled "Federated Sensor Array for Use with a Motorized Mobile System and Method of Use" discloses the integration of non-contact sensors and control logic into an MMS controller. The federated sensors have overlapping sensing fields, generally operate independently, and report certain data relevant to navigation and stability which is then used by the MMS controller. Motor, seat, and auxiliary controllers may be hosted in the MMS controller along with the federated sensor logic. The integration of these systems and applications into an MMS lays the foundation for situational awareness (SA).

Situational awareness is the ability to be cognizant of oneself in a given space. It is an organized knowledge of objects and state kinematics in relation to oneself in a given space or scenario. Situational awareness also involves understanding the relationship of these objects when there is a change of position or kinematic state. The goal is to integrate this data into the MMS and use it to support a richer, safer, and more independent experience for the user.

The application entitled "System and Methods for Sensor Integration in Support of Situational Awareness for a Motorized Mobile System" further discloses the integration of new sensor technologies in support of a deeper and richer situational awareness for the user. These new systems use the data generated about the user, the environment, targets in the environment, and the user's relationship to them. This information may be generated from one or more sources and include data from non-contact sensors, like radar, optical, laser, and ultrasonic sensors. These non-contact sensors can generate data about the environment, including range measurements, bearing measurements, target classification, and target kinematics. The new sensors provide a much richer set of data about the environment.

The federated system uses a single type of sensor that generates a single report (i.e. a communication with or identifying data sensed by the sensor) with what is called a single mode variance, where each sensor has distinct capabilities and one or more fixed errors inherent to the sensor. Ultra-sonic sensors have better range determination than cross range position determination, for instance. In an example, using data from a different type of sensor, a good cross range report can be generated, but with poor down range determination. In this evolving system, the best of two (or more) separate reports may be combined. This is referred to as a dual mode variance.

The application entitled "System and Methods for Enhanced Autonomous Operations of a Motorized Mobile System" discloses the implementation of advanced filtering techniques and sensor fusion in support of situational awareness and autonomy. Adding more sensors to a federation of sensors increases expense, weight, and power consumption. Integration and use of sensor fusion (e.g. using different types of sensors in one system) and advanced filtering techniques improves the information the MMS controller uses to track the user and environment, while reducing complexity and cost when compared to a federated approach. Decision logic consisting of data association techniques, track and target management, handling out of sequence measurements, and sensor frame management are all building blocks for this leap in system capability.

In this enhanced system, raw data is received and "filtered", or as is known in the art fused, with other data related to the MMS user and their activities while navigating in the environment. The other data may include certain biometric data, user inputs, and user activities. Filtering and state estimation are some of the most pervasive tools of engineering. In some embodiments, a model may be used to form a prediction of a state into the future, followed by an observation of the state or actual measurement of the expectation. A comparison of the predicted state and the measured state is then made. If the observations made are within the predicted measurements, the model may be adjusted by reducing the covariance of the next measurement, thereby increasing system confidence. If the observations are outside of the predicted measurements, the model may be adjusted to increase the covariance of the next measurement, thereby decreasing system confidence.

In this enhanced system, the MMS is fully aware of its environment and can travel safely wherever the user wishes to go, within reason. Moreover, the MMS may learn to anticipate the needs of the user. The result is a user experience that is safe, secure, and independent, based on the user's base abilities and current condition.

Other systems may be integrated to improve user experience. As a non-limiting example, augmented reality (AR) may be included. Augmented reality is a live direct or indirect view of a physical, real-world environment where the elements are augmented (or supplemented) by computer-generated sensory input. The input can be sound, smell, or graphics. It is related to a more general concept called computer-mediated reality, in which a view of reality is modified, possibly even diminished rather than augmented, by a computer. As a result, the technology functions by enhancing one's current perception of reality. Virtual Reality (VR) is another technology that may be integrated to improve user experience. By contrast, VR replaces the real world with a simulated one. Augmentation is conventionally in real time and in semantic context with environmental elements, such as sports scores on TV during a match. However, VR refers to computer technologies that use VR headsets, sometimes in combination with physical spaces or multi-projected environments, to generate realistic images, sounds, and other sensations that simulate a user's physical presence in a virtual or imaginary environment.

In another aspect, a method for a motorized mobile system (MMS) comprises generating first sensor data about an object from a first sensor, wherein the first sensor data about the object comprises a first range measurement to the object and a first bearing measurement to the object, the first range measurement has an associated first uncertainty, and the first bearing measurement has an associated second uncertainty. The method further comprises generating second sensor data about the object from a second sensor, wherein the second sensor data about the object comprises a second range measurement to the object and a second bearing measurement to the object, the second range measurement has an associated third uncertainty, and the second bearing measurement has an associated fourth uncertainty. A lower range uncertainty between the first uncertainty and the third uncertainty is selected by a processor. A lower bearing uncertainty between the second uncertainty and the fourth uncertainty is selected by the processor. The bearing measurement associated with the selected lower bearing uncertainty and the range measurement associated with the selected lower range uncertainty are combined by the processor as a location of the object within a reduced area of uncertainty.

In another aspect, a method for a motorized mobile system (MMS) comprises generating first sensor data about an object from a first sensor, the object located proximate to the motorized mobile system, wherein the first sensor data about the object comprises a first range measurement to the object and a first bearing measurement to the object, the first range measurement has an associated first uncertainty, and the first bearing measurement has an associated second uncertainty. The method further comprises generating second sensor data about the object from a second sensor, the object located proximate to the motorized mobile system, wherein the second sensor data about the object comprises a second range measurement to the object and a second bearing measurement to the object, the second range measurement has an associated third uncertainty, and the second bearing measurement has an associated fourth uncertainty. A lower range uncertainty between the first uncertainty and the third uncertainty is selected by a processor. A lower bearing uncertainty between the second uncertainty and the fourth uncertainty is selected by the processor. The bearing measurement associated with the selected lower bearing uncertainty and the range measurement associated with the selected lower range uncertainty are combined by the processor as a location of the object within a reduced area of uncertainty.

Applicant(s) herein expressly incorporate(s) by reference all of the following materials identified in each paragraph below. The incorporated materials are not necessarily "prior art".

ISO/IEC 15408-1:2009, 3rd Edition: "Information technology—Security techniques—Evaluation criteria for IT security—Part 1: Introduction and general model".

ISO/IEC 15408-2:2008, 3rd Edition: "Information technology—Security techniques—Evaluation criteria for IT security—Part 2: Security functional components".

ISO/IEC 15408-3:2008, 3rd Edition: "Information technology—Security techniques—Evaluation criteria for IT security—Part 3: Security assurance components".

802.11-2016: "IEEE Standard for Information technology—Telecommunications and information exchange between systems Local and metropolitan area networks—Specific requirements—Part 11: Wireless LAN Medium Access Control (MAC) and Physical Layer (PHY) Specifications".

1609.0-2013: "IEEE Guide for Wireless Access in Vehicular Environments (WAVE)—Architecture".

1609.2-2016: "IEEE Standard for Wireless Access in Vehicular Environments—Security Services for Applications and Management Messages".

1609.4-2016: "IEEE Standard for Wireless Access in Vehicular Environments (WAVE)—Multi-Channel Operation".

1609.11-2010: "IEEE Standard for Wireless Access in Vehicular Environments (WAVE)—Over-the-Air Electronic Payment Data Exchange Protocol for Intelligent Transportation Systems (ITS)".

1609.12-2016: "IEEE Standard for Wireless Access in Vehicular Environments (WAVE)—Identifier Allocations".

ETSI EN 302 663 (V1.2.1): "Intelligent Transport Systems (ITS); Access layer specification for Intelligent Transport Systems operating in the 5 GHz frequency band."

ETSI EN 302 571 (V1.2.1): "Intelligent Transport Systems (ITS); Radiocommunications equipment operating in the 5 855 MHz to 5 925 MHz frequency band; Harmonized EN covering the essential requirements of article 3.2 of the R&TTE Directive".

ETSI TS 102 792 (V1.2.1): "Intelligent Transport Systems (ITS); Mitigation techniques to avoid interference between European CEN Dedicated Short Range Communication (CEN DSRC) equipment and Intelligent Transport Systems (ITS) operating in the 5 GHz frequency range".

IEEE 802-2014: "IEEE Standard for Local and Metropolitan Area Networks: Overview and Architecture".

ANSI/IEEE Std 802.2 (1998): "IEEE Standard for Information technology—Telecommunications and information exchange between systems—Local and metropolitan area networks—Specific requirements—Part 2: Logical Link Control".

ISO/IEC 7498-1:1994: "Information technology—Open Systems Interconnection—Basic Reference Model: The Basic Model".

ITU-T Recommendation X.691 (2015): "Information technology—ASN.1 encoding rules: Specification of Packed Encoding Rules (PER)".

ETSI TS 102 687 (V1.1.1): "Intelligent Transport Systems (ITS); Decentralized Congestion Control Mechanisms for Intelligent Transport Systems operating in the 5 GHz range; Access layer part".

IEEE 1003.1-2008: "IEEE Standard for Information Technology—Portable Operating System Interface (POSIX (R))".

IEEE 802.15.1-2005: "Wireless medium access control (MAC) and physical layer (PHY) specifications for wireless personal area networks (WPANs)".

IEEE 802.15.4-2015: "IEEE Standard for Low-Rate Wireless Networks".

ISO/IEC 18092:2013: "Information technology—Telecommunications and information exchange between systems—Near Field Communication—Interface and Protocol (NFCIP-1)".

IEEE 802.16-2012: "IEEE Standard for Air Interface for Broadband Wireless Access Systems".

ISO/IEEE 11073-20601-2014: "IEEE Health informatics—Personal health device communication—Part 20601: Application profile—Optimized Exchange Protocol".

Bluetooth SIG: "Bluetooth Core Specification", v5.0.

If it is believed that any of the above-incorporated material constitutes "essential material" within the meaning of 37 CFR 1.57(d)(1)-(3), applicant(s) reserve the right to amend the specification to expressly recite the essential material that is incorporated by reference as allowed by the applicable rules.

Aspects and applications presented here are described below in the drawings and detailed description. Unless specifically noted, it is intended that the words and phrases in the specification and the claims be given their plain and ordinary meaning to those of ordinary skill in the applicable arts. The inventors are aware that they can be their own lexicographers if desired. The inventors expressly elect, as their own lexicographers, to use only the plain and ordinary meaning of terms in the specification and claims unless they clearly state otherwise and expressly set forth the "special" definition of that term. Absent such clear statements of intent to apply a "special" definition, it is the inventors' intent and desire that the plain and ordinary meaning to the terms be applied to the interpretation of the specification and claims.

Further, the inventors are informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f) to define the systems, methods, processes, and/or apparatuses disclosed herein. To the contrary, if the provisions of 35 U.S.C. § 112(f) are sought to be invoked to define the embodiments, the claims will specifically and expressly state the exact phrases "means for" or "step for" and will also recite the word "function" (i.e., will state "means for performing the function of . . . "), without also reciting in such phrases any structure, material, or act in support of the function. Thus, even when the claims recite a "means for performing the function of . . . " or "step for performing the function of . . . .", if the claims also recite any structure, material, or acts in support of that means or step then it is the clear intention of the inventors not to invoke the provisions of 35 U.S.C. § 112(f). Moreover, even if the provisions of 35 U.S.C. § 112(f) are invoked to define the claimed embodiments, it is intended that the embodiments not be limited only to the specific structures, materials, or acts that are described in the preferred embodiments, but in addition, include any and all structures, materials, or acts that perform the claimed function as described in alternative embodiments or forms, or that are well known present or later-developed equivalent structures, materials, or acts for performing the claimed function.

BRIEF DESCRIPTION OF THE DRAWINGS

A more complete understanding of the systems, methods, processes, and/or apparatuses disclosed herein may be derived by referring to the detailed description when considered in connection with the following illustrative figures. In the figures, like-reference numbers refer to like-elements or acts throughout the figures.

FIG. 21 depicts an S-MMS paired to an augmented reality (AR) device via a wireless link.

FIG. 26A depicts an exemplary placement of sensors to measure forces on an arm rest.

FIG. 26B depicts an exemplary placement of sensors to measure forces on a foot rest.

FIG. 27A depicts an embodiment of a self-retracting control unit when extended.

FIG. 27B depicts an embodiment of a self-retracting control unit when retracted.

Figure 1:
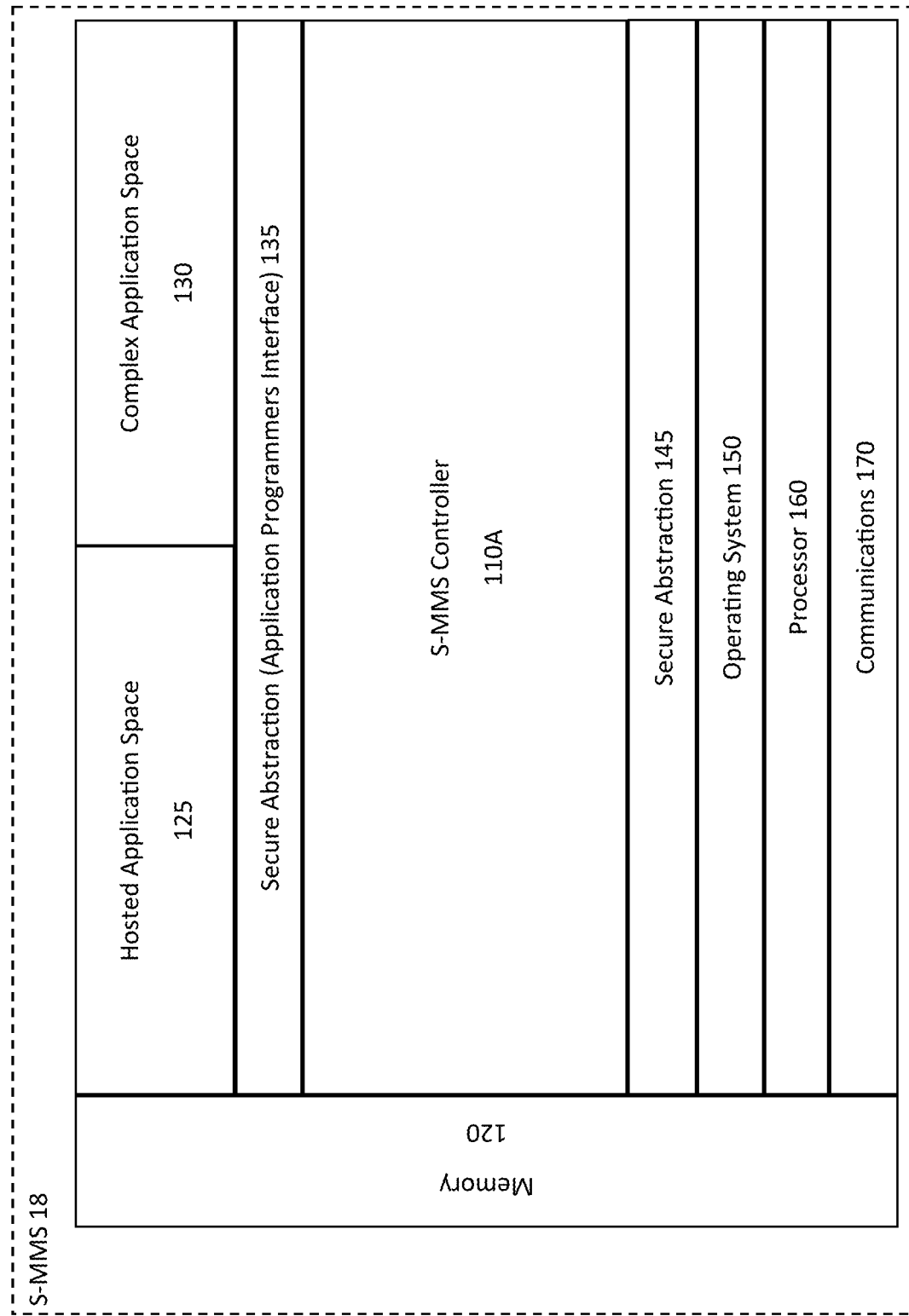
FIG. 1 depicts a control system architecture with hardware and software components for an S-MMS.

Elements and acts in the figures are illustrated for simplicity and have not necessarily been rendered according to any particular sequence or embodiment.

DETAILED DESCRIPTION

In the following description, and for the purposes of explanation, numerous specific details, process durations, and/or specific formula values are set forth in order to provide a thorough understanding of the various aspects of exemplary embodiments. However, it will be understood by those skilled in the relevant arts that the apparatus, systems, and methods herein may be practiced without all of these specific details, process durations, and/or specific formula values. Other embodiments may be utilized and structural and functional changes may be made without departing from the scope of the apparatus, systems, and methods herein. It should be noted that there are different and alternative configurations, devices, and technologies to which the disclosed embodiments may be applied. The full scope of the embodiments is not limited to the examples that are described below.

In the following examples of the illustrated embodiments, references are made to the accompanying drawings which form a part hereof, and in which is shown by way of illustration various embodiments in which the systems, methods, processes, and/or apparatuses disclosed herein may be practiced. It is to be understood that other embodiments may be utilized and structural and functional changes may be made without departing from the scope.

Systems and methods are disclosed for use of multiple sensors and their associated data on a smart motorized mobile system (S-MMS). Referring generally to FIGS. 1-34, systems, methods, and apparatuses for providing safety and independence for S-MMS users are illustrated. The systems and methods disclosed support non-automobile motorized mobile systems, such as powered mobile chairs, mobility scooters, electronic conveyance vehicles, riding lawn mowers, grocery carts, ATVs, golf carts, off-road vehicles, and other recreational and/or medical mobility systems, but excludes automobiles. For the purposes of this disclosure, automobiles are defined as passenger cars, trucks, passenger buses, and other passenger or property transporting motorized vehicles intended for licensed operation on state and national highways. A non-limiting, illustrative example of a motorized mobile chair is used throughout the disclosure. In various embodiments, a placement or location of at least one sensor may be determined based at least in part upon unique S-MMS dynamic characteristics, user seating position, wheel or track location associated with the S-MMS, or other characteristics relevant to the disclosed systems and methods.

Some embodiments of the systems disclosed may be referred to as separate generations based on level of capability. While these generations are discussed as separate embodiments, it should be clear that any one or more aspects of any one or more generations may be combined to form other systems not explicitly disclosed herein (or in the related co-pending applications). The generations are as follows: Generation 0 (Gen 0), Generation I (Gen I), Generation II (Gen II), and Generation III (Gen III).

The motorized mobile systems in existence today may be referred to herein as Generation 0. Generation 0 is an MMS with a user interface and a control system. Generation 0 is hosted in a controller with a Human Machine Interface (HMI) typically consisting of a joystick, tactile surface array, sip and puff type array, or similar interface. The joystick receives input indicating "move forward", the command is generated, and control instructions are sent to a motor controller, which responds with a preconfigured response. The control instructions may include a change in state or an adjustment of an operating parameter. The state of the art for a Generation 0 system is to provide extremely simple control instructions and open loop limits on the MMS. Open loop systems lack the ability for self-correcting actions. An example of an open loop limit currently in use on MMSs is to cut the maximum MMS speed to a predetermined set point if the user raises the seat position above a certain threshold. The motor controller responds directly to the user input regardless of the environment proximate to the MMS. A new user may have a learning curve to master before they can confidently maneuver close to people, objects, or in confined environments.

A Smart Motorized Mobile System (S-MMS) of the present disclosure is an evolution of MMS technology, and includes embodiments of a new controller and control architecture, some of which include secure methods for collecting and transmitting data across one or more networks.

The present application and one or more related applications disclose improved generations of S-MMS architectures, including Generations I-III architectures. Generation I is an embodiment for a group of sensors reporting to a controller for the S-MMS. Generation II embodiments further include consideration for scanning and/or image sensors operating in overlapping regions. Using a sensor with good down range error, and a second sensor with good cross range error, a Generation II system embodiment can coordinate reports in real-time, associate them, and take the best measurements in an ability to make the situational awareness picture more accurate. This use of more than one sensor is typically referred to as dual mode variance.

Generation II S-MMSs may take advantage of their ability to exchange data with other like equipped systems about their environment. In addition to other like equipped systems, the S-MMS may be configured to receive data from traffic through Dedicated Short-Range Communications (DSRC) across an IEEE 802.11P link. This data may help the user to better navigate next to a road way, or along paths that are shared by automobiles and other MMSs. For an S-MMS user, the ability to announce one's presence and the ability to control traffic could be lifesaving.

Generation II systems are based on historical data or on observations of state at a finite time, in this case time $T_1$. In one example, an event is measured at time $T_1$, the event is processed at time $T_2$, data for the processed event is transmitted at time $T_3$, the data for the processed event is related to other data at time $T_4$, and any other actions that need to be carried out are done at time $T_5$. This can be done very quickly, e.g. from tenths of a second to even seconds. Regardless of delay, it is all historic.

Generation III is an embodiment for a multi-generation controller architecture and logic. In some embodiments, a Generation III system may host one or more of the previous generations or combinations thereof. Generation III systems go beyond dual mode variance to true sensor fusion.

The S-MMS controller may be one or more processors (hardware), application-specific integrated circuits, or field-programmable gate arrays that host the disclosed architecture. Control signals may be via wired or wireless communications, and comprised of digital and/or analog signals.

Control System Embodiment

FIG. 1 depicts an embodiment of an S-MMS 18 control system composed of hardware and software components. An S-MMS controller 110 lies between two secure abstraction layers 135 and 145. Abstraction layers are used as a way of hiding the implementation details of a particular set of functionalities, allowing the separation of concerns to facilitate interoperability and platform independence. The upper abstraction layer 135 abstracts through an Application Programmers Interface (API) to a hosted application space 125 and a complex application space 130. The API is a set of subroutine definitions, protocols, and tools for building applications. An API allows for communication between the various components. The complex application space 130 may include hosted control logic for an S-MMS 18. Below the S-MMS controller 110 and its secure abstraction 145 is a breakout of the operating system 150, one or more processors 160 (which are hardware), and a communications layer 170, which may include a hardware communications interface. Memory 120, which is hardware, cross cuts all of the layers in the depicted embodiment and may include volatile and non-volatile non-transitory computer storage media for storing information. The S-MMS controller 110 is software that executes on one or more processors 160 on the S-MMS 18 and is stored in memory 120.

Figure 2:
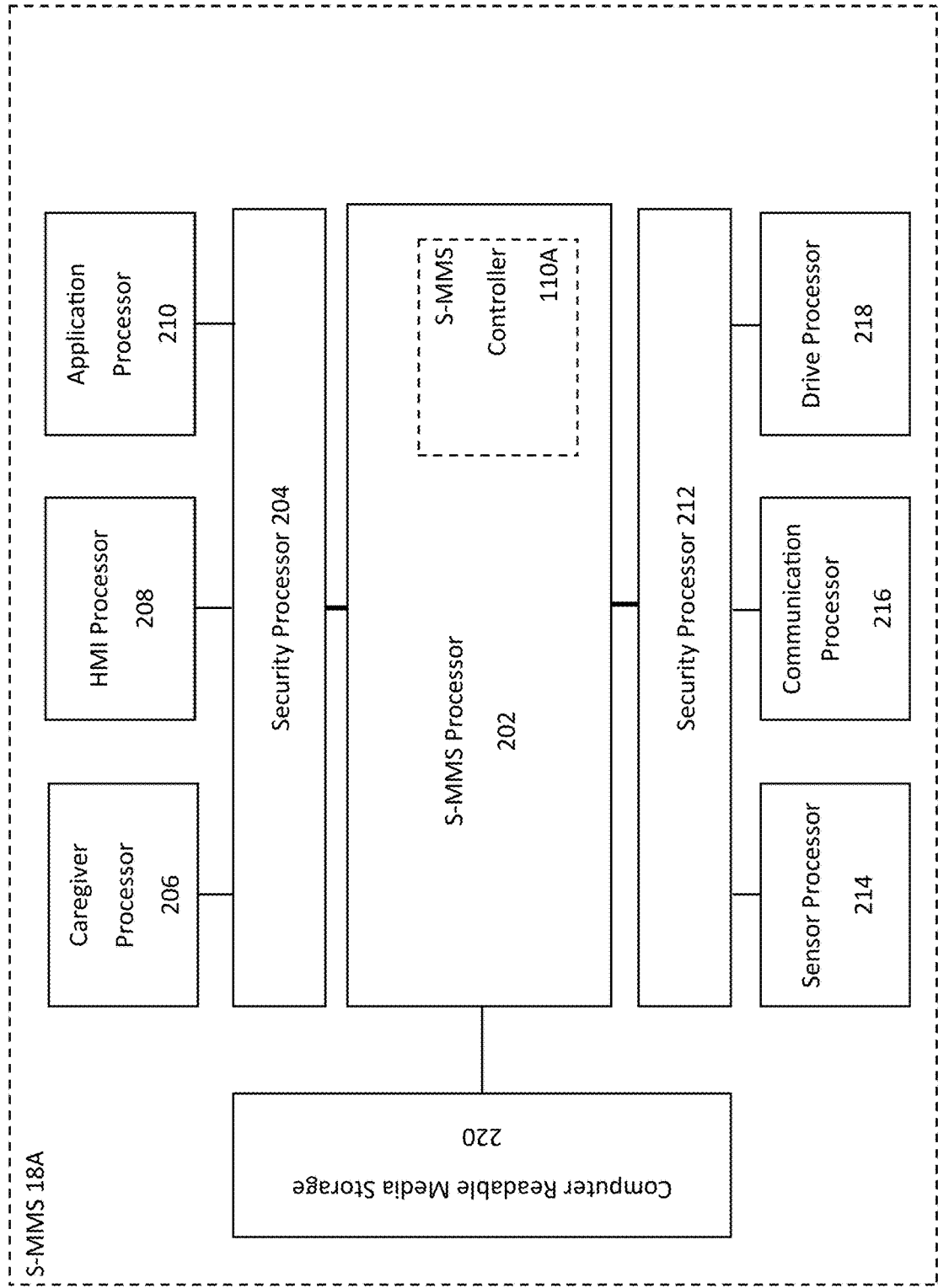
FIG. 2 depicts an embodiment of an S-MMS hardware architecture.

With a focus now on the one or more hardware processors that the S-MMS controller 110 is executed on and interacts with, FIG. 2 depicts a hardware embodiment of an S-MMS 18A architecture. The depicted electrical architecture comprises an S-MMS processor 202 between two security processors 204 and 212, each of which is hardware. The S-MMS processor 202 may be paired with a lock-step processor (not depicted) for critical life, health, and safety applications, in some embodiments. The security processors 204 and 212 may host (i.e. execute) modules and other software, such as the previously disclosed secure abstraction APIs 135 and 145. Additionally or alternatively, the security processors may host services, such as watch-dog and data source authentication services. The S-MMS controller 110A is hosted on an S-MMS processor 202. The processors may comprise one or more of a processor, multiple processors, an application-specific integrated circuit, or a field-programmable gate array.

The S-MMS controller 110A utilizes computer readable storage media 220, which includes the memory 120, for data storage and retrieval during operation. Executable program instructions for the S-MMS controller 210D also may be stored in the memory 120. The memory 120 is one or more of a volatile and non-volatile non-transitory computer storage medium for storing information and may be located onboard the S-MMS 18A, may be remote storage available on a smart device or server, or some combination of the foregoing. One or more secure, encrypted memory partitions are used to store electronic protected health information (ePHI) and other secure health data. The data stored on the secure memory is only made available to one or more pre-authorized systems, wherein the pre-authorized system comprises a device or service associated with an individual user. This may include a mobile motorized system, a smart device, a computer, a data terminal, or a device or service associated with an approved third party.

The S-MMS 18A hardware system may comprise multiple additional processors beyond the core S-MMS processor 202. In the case of a power wheelchair S-MMS, these additional hardware processors may include one or more caregiver processors 206, one or more HMI processors 208, one or more application processors 210, one or more sensor processors 214, one or more communication processors 216, and one or more drive processors 218, each of which is hardware. Each processor executes software and may produce control signals wherein the control signal is a wired or wireless signal, and wherein the control signal comprises one or more of a digital or an analog signal, and generally comprises or indicates data, instructions, and/or a state. A brief description of each of the additional processors for the depicted embodiment is provided below.

A caregiver processor 206 may be physically attached to the S-MMS or may be part of a remote device. In one embodiment, a caregiver processor 206 is a duplicate HMI and associated processor for the S-MMS that allows a caregiver to physically drive or otherwise maneuver or control the S-MMS or its components.

An HMI processor 208 may accept one or more user inputs from one or more HMI devices, such as a joystick or touch screen, and convert them into one or more control signals with data and/or instructions which are transmitted in response to the one or more user inputs at the HMI. Control instructions may comprise one or more of a calculation, a logical comparison, a state, a change in state, an instruction, a request, data, a sensor reading or record, an adjustment of an operating parameter, a limitation of a feature or capability, or an enablement of a feature or capability.

An application processor 210 may include one or more processors embedded in ancillary products, such as a seat controller, lighting controller, or $3^{rd}$ party device. Typically, these processors receive one or more control signals that causes them to respond with a preconfigured response, wherein the preconfigured response may include moving, measuring, changing a state, transmitting data, or taking operational control of the associated hardware (e.g. raising, lowering, or angling a seat or increasing or decreasing a light brightness or turning a light on or off). An application processor 210 may additionally or alternatively supply data about the S-MMS or use data generated from one or more sensors.

A sensor processor 214 receives data generated from one or more sensors used by the S-MMS or otherwise associated with one or more characteristics of the mobile system or a user of the mobile system. The received data may be stored in a memory and/or transmitted. Multiple sensors may use a single sensor processor 214 or multiple processors. Additionally or alternatively, individual sensors may have their own (e.g. dedicated) processors.

A communication processor 216 is used to establish one or more connections with one or more devices and transmits communications to, and receives communications from, one or more devices through associated devices of the S-MMS (e.g. one or more transceivers). Devices may communicate with the processor via wired or wireless means. These devices may be located on the S-MMS 18A or may be remote to the S-MMS 18A. A communication processor 216 may be part of a communication system for a mobile system for secure transmission and/or secure reception of data. In some embodiments, the S-MMS processor 202 may have an integrated communication processor or the S-MMS processor performs the functions of the communication processor In an exemplary embodiment, a communication processor 216 on the S-MMS 18A is configured to establish secure connections between the S-MMS 18A and one or more other wireless devices over which data is transmitted and received by the communication processor and the one or more wireless devices. Responsive to a secure connection being established by the communication processor 216 with a wireless device, the communication processor retrieves from a secure memory 220 one or more of stored first data or stored second data; wherein first data is data generated from one or more sensors associated with one or more characteristics of the mobile system (e.g. sensors on or used by the S-MMS 18A for measurement of distances, angles, or planes at which the S-MMS is operating, drive speed or direction, angular momentum, or other operational characteristics of the S-MMS itself) and second data is data generated from one or more sensors associated with a user of the mobile system (e.g. user presence in the seat, heart rate, seat moisture, or other characteristics of the user of the S-MMS). One or more of the first data and second data is then communicated to the wireless device via the secure connection for storage in a secure second memory of the wireless device. The wireless device associated and the communication processor 216 may communicate using one or more of cellular, 802.11, Wi-Fi, 802.15, Bluetooth, Bluetooth Low Energy, 802.20, and WiMAX.

A drive processor 218 receives one or more control signals, for example from the S-MMS controller 110A, that cause the drive processor to respond with a preconfigured response to the steering system and/or drive motor(s) of the S-MMS, wherein the preconfigured response includes one or more of taking operational control of the steering system or drive motor(s), steering the S-MMS, or starting and/or stopping one or more drive motors to move the S-MMS in one or more directions. A drive processor 218 may additionally or alternatively supply data generated from one or more sensors associated with one or more characteristics of the mobile system to the S-MMS controller 110A.

In some embodiments, one or more sensors may be mounted to different physical locations on an S-MMS 18A. In some embodiments, the sensing area/view/field of one or more sensors may overlap the sensing area/view/field of one or more other sensors or a contiguous sensing field may exist between sensors to obtain a complete 360-degree sensing area view around the S-MMS 18A, which is referred to herein as a federation of sensors. In some embodiments, the one or more sensors are non-cooperating independent sensors that generate a detection response to objects with some confidence (e.g. generate a control signal that indicates one or more objects were detected and a distance to the one or more objects or other measurement data relative to the one or more objects). In such an embodiment, the kinematic states of detection that can be determined include position and time of detection. In some embodiments, control logic may be deployed in an S-MMS controller 110A to create an integrated system of systems within the S-MMS 18A.

Situational Awareness System

Situational awareness (SA) is the perception of environmental elements, objects, conditions, and events with respect to the observer, in terms of time and space. Situational awareness involves being aware of what is happening in the vicinity of the user to understand how information, events, and one's own actions will impact objectives, both immediately and in the near future. More importantly, situational awareness involves the comprehension of information's meaning, and the projection of an object's status after some variable has changed or occurred, such as time, or some other variable has changed or occurred, such as a predetermined event. Situational awareness is also the field of study concerned with understanding the environment critical to a decision-making process in a complex dynamic system. Dynamic situations may include ordinary, but nevertheless complex, tasks such as maneuvering an S-MMS in an environment safely.

A federation of sensors may be oriented proximate to an S-MMS 18 in such a way to ensure 360-degree sensor coverage. These sensors may report to an S-MMS controller 110 that is tasked with receiving information from one or more sensors, interpreting information from one or more sensors, and taking action based on information provided by the one or more sensors. The S-MMS controller 110 may attempt to assign meaning to the information and create a projection of one or more statuses or states of the S-MMS 18, including after some variable has changed or occurred. When one or more sensors report data identifying an object, the S-MMS controller 110 may respond based on those reports, either automatically or with user input.

Figure 3:
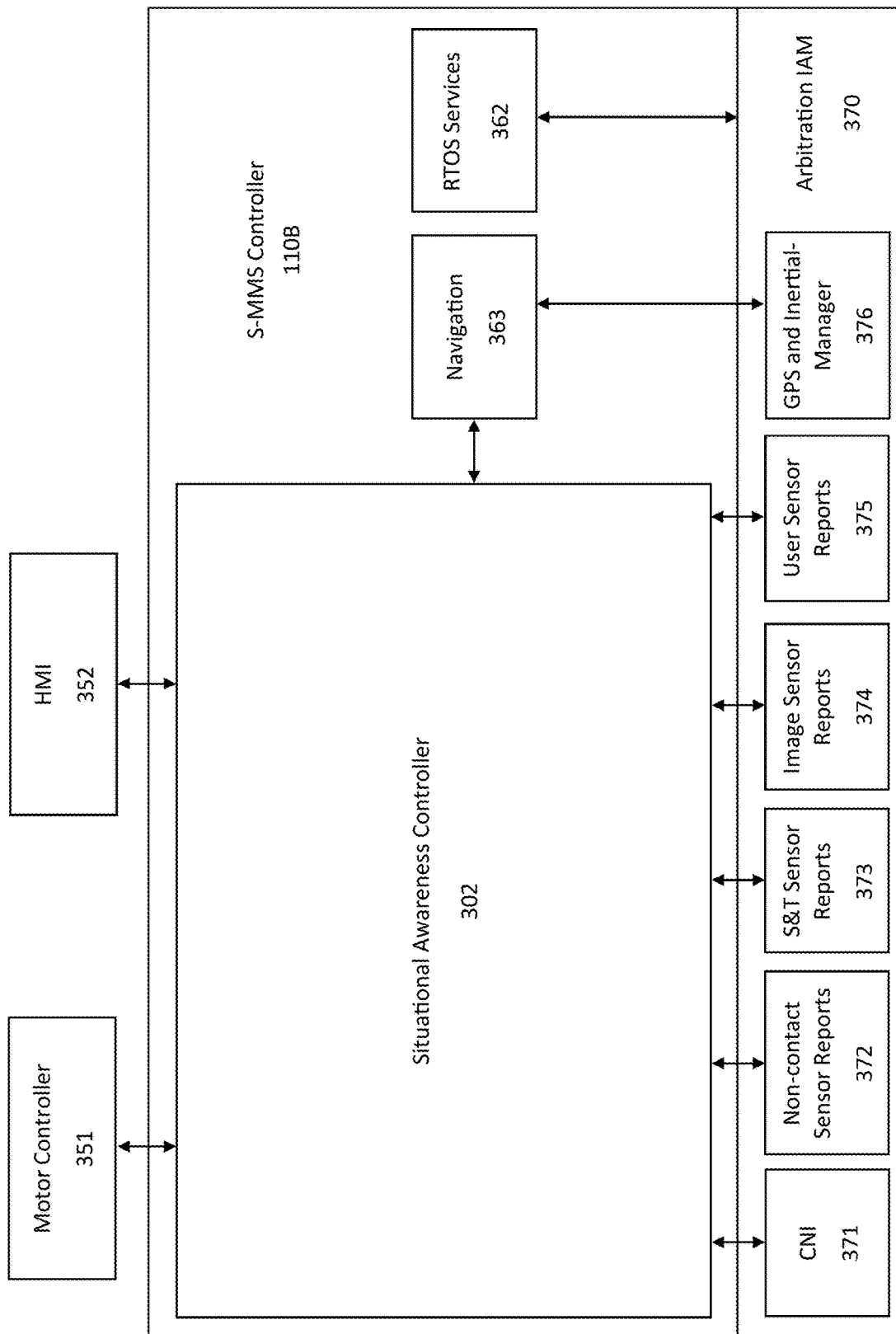
FIG. 3 depicts an embodiment of a control system architecture for an S-MMS hosting an integrated situational awareness controller.

FIG. 3 depicts an embodiment in which the S-MMS controller 110B is deployed on an S-MMS. The depicted embodiment comprises a situational awareness controller 302 within the S-MMS controller 110B. The S-MMS situational awareness controller 302 communicates with a motor controller 351 and a Human Machine Interface (HMI) 352. In some embodiments, one or more of the motor controller 351 and HMI 352 may be integrated into the S-MMS controller 110B. The depicted S-MMS controller 110B further comprises real-time operating system (RTOS) services 362 and navigation 363.

An arbitration Information Assurity Manager (IAM) 370 manages sensor reports from one or more sensors on or used by the S-MMS 18 and may include communication, navigation, and identification (CNI) 371 processing capabilities. Communications received from a sensor are termed sensor reports. In some embodiments, the arbitration IAM 370 resides on a security or arbitration processor 212 (FIG. 2). Additionally or alternatively, functions of the CNI 371 may be performed by a dedicated communication processor 216 (FIG. 2). Sensor reports received and managed by the arbitration IAM 370 may include non-contact sensor reports 372, search and track sensor reports 373, image sensor reports 374, and user sensor reports 375. Sensor reports (372-375) may be composed of data stored in one or more of long-term or short-term system memory 120 or read from an input port on an S-MMS 18A processor (e.g. processors 212, 216 or 214). A report (371-376) may include additional data beyond a simple measurement, including sensor status, confidence levels, or other information.

Non-contact sensors are devices used to take a measurement, often a distance, without coming in contact with the detected object. There are many types of non-contact sensors, including optical (e.g. LIDAR), acoustic (e.g. RADAR or ultrasonic), and magnetic (e.g. hall effect sensor). Microphones may additionally be included as a non-contact sensor. Search and track sensors may include image and non-contact sensor types, but are sensors that often have larger fields of view and may scan within these fields of view. Image sensors detect and convey information that constitutes an image or series of images/video, wherein the image(s)/video may contain light or electromagnetic radiation information on an area. These sensor reports interface to the specific sensor types in the system to identify measurements, detections, number, efficiency, health, degraded performance, states, statuses, and/or other data of each sensor in the sensing system.

The depicted arbitration IAM 370 further comprises a global positioning system (GPS) and inertial manager 376. In the depicted embodiment, the situational awareness controller 302 communicates with the CNI 371, sensor reports 372, 373, 374, and 375 and navigation 363. Navigation 363 communicates with the GPS and inertial manager 376 in the arbitration IAM 370. The depicted embodiment of the situational awareness controller 302 includes logic to manage the sensors, including one or more of on and off, sweep rate, sensor volume, regional interrogation, and/or other operations.

The CNI 371 manages communications through system links and off board links to enable vehicle to device, intra-vehicle, and inter-vehicle communication and coordination, including cooperative navigation among vehicles and using other devices and identification of devices and vehicles. In some embodiments, the CNI 371 identifies other data sources and retrieves data from other data sources, including for threats detected and kinematic states of sensors, vehicles, and devices. The CNI 371 is also responsible for GPS corrected system-wide time and processor time sync across the system in conjunction with the operating system. For example, the CNI 371 receives an accurate time via the GPS and inertial manager 376 and transmits that accurate time to all hardware processors along with an instruction to sync their internal clocks to that accurate time. This time coordination function is important in some embodiments since errors in time coordination can introduce as much error in system performance as a bad sensor reading in those embodiments. Propagating a sensor measurement to the wrong point in time can induce significant confusion to filters, such as a Kalman filter, especially if time goes backward due to sync errors.

The CNI 371, in some embodiments, may be configured to receive data from one or more different sources, including other like-equipped S-MMSs, vehicles and traffic devices, among others, through a Dedicated Short-Range Transceiver (DSRC), for instance, across an IEEE 802.11P link, which may be formatted in an IEEE 1609 format. This data may help the user to better navigate next to a roadway or along paths that are shared by automobiles. Some embodiments may allow for traffic lights, speed signs, and traffic routing to be dynamically altered. For an S-MMS user, the ability to announce one's presence and thereby enable a traffic control device to effect a change in traffic, such as by changing a stop light to red, could be lifesaving.

A search and track function 373 may be used to maintain sensor health, detect sensor failures, monitor sensor zones of coverage (sensor zones), and notify the situational awareness controller 302 or other component of the S-MMS controller 110B of sensor system degradation or other states. The search and track function 373 may also manage the transition of sensors from online and off-line states (including plug and play future options).

The user sensor reports 375, in some embodiments, may be configured to receive data from one or more sensors used to monitor user condition, user position, and/or user status. This data may allow for assistive behaviors to be triggered and/or tuned by the situational awareness controller 302 to the human in the loop of the S-MMS 18.

The GPS and inertial manager 376 includes one or more inertial measurement unit (IMU) data services that receives one or more reports from an attitude and heading reference system (AHRS) that includes an IMU. An IMU of an AHRS consists of one or more sensors on three axes that provide attitude information of the S-MMS 18 to the GPS and inertial manager 376, including yaw, pitch, and roll of the S-MMS and deviations to each. As an example, an x-axis may typically be lateral across the S-MMS 18 coaxial with the axles of the front wheels of the S-MMS, extending 90-degrees left and 90-degrees right, a y-axis may extend forward and rearward of the S-MMS, and a z-axis may extend vertically through the S-MMS, 90-degrees to the x and y axes. An IMU typically comprises acceleration and rate determining sensors on each axis. In the case of x, y, and z measurements, the IMU is referred to as a 6-Degree of Freedom (DOF) sensor. Some IMUs also have a small hall device on each axis to measure the magnetic line of flux of the earth's magnetic poles, similar to a compass, that allows for the calculation of true, earth referenced orientation. These IMU embodiments are referred to as a 9-DOF sensor and are more accurate than a 6-DOF sensor. However, some systems may interpolate the z-axis by detecting gravity on either the x or y axes, which may be less accurate. The IMU is fixed to the S-MMS 18 in some embodiments and provides reports to the GPS and inertial manager 376.

The GPS and inertial manager 376 also receives GPS signals from a GPS receiver. The GPS receiver may be mounted to the S-MMS 18, be part of a smart device paired or otherwise linked to the S-MMS, or be another receiver that transmits signals to the S-MMS or a smart device linked to the S-MMS.

Navigation 363, in the depicted embodiment, is an inertial reference system, including an inertial navigation system (INS), for navigating using dead reckoning (DR). Dead reckoning is the process of calculating the S-MMS 18 current position by using a previously determined position, or fix, and advancing that position based upon known or estimated speeds and steering over elapsed time and heading. In one embodiment, DR uses GPS location data (e.g. via GPS and inertial manager 376) to update the INS DR fix. Speed, heading, and elapsed time data are then provided by the INS function of navigation 363 to the situational awareness controller 302. S-MMS speed (e.g. velocity and/or acceleration) may be received directly from one or more motor controllers 351. Additionally, speed and heading may be received or calculated from one or more GPS and inertial manager 376 reports. Elapsed time is provided by RTOS services 362. The navigation 363 allows the S-MMS 18 to navigate inside a building without GPS or otherwise (e.g. outside of GPS coverage) to a similar degree of accuracy as navigating outside with continuous GPS data or otherwise. Speed, heading, and elapsed time for navigation 363, in some other embodiments, is calculated onboard the processors of internal and/or external sensors, including one or more GPS receivers and one or more solid state inertial measurement units (IMUs). In some embodiments, the S-MMS processor 202 calculates speed, heading, and elapsed time and generates steering and drive signals, including optionally based on one or more non-contact sensor reports and/or GPS and inertial manager reports.

Figure 4:
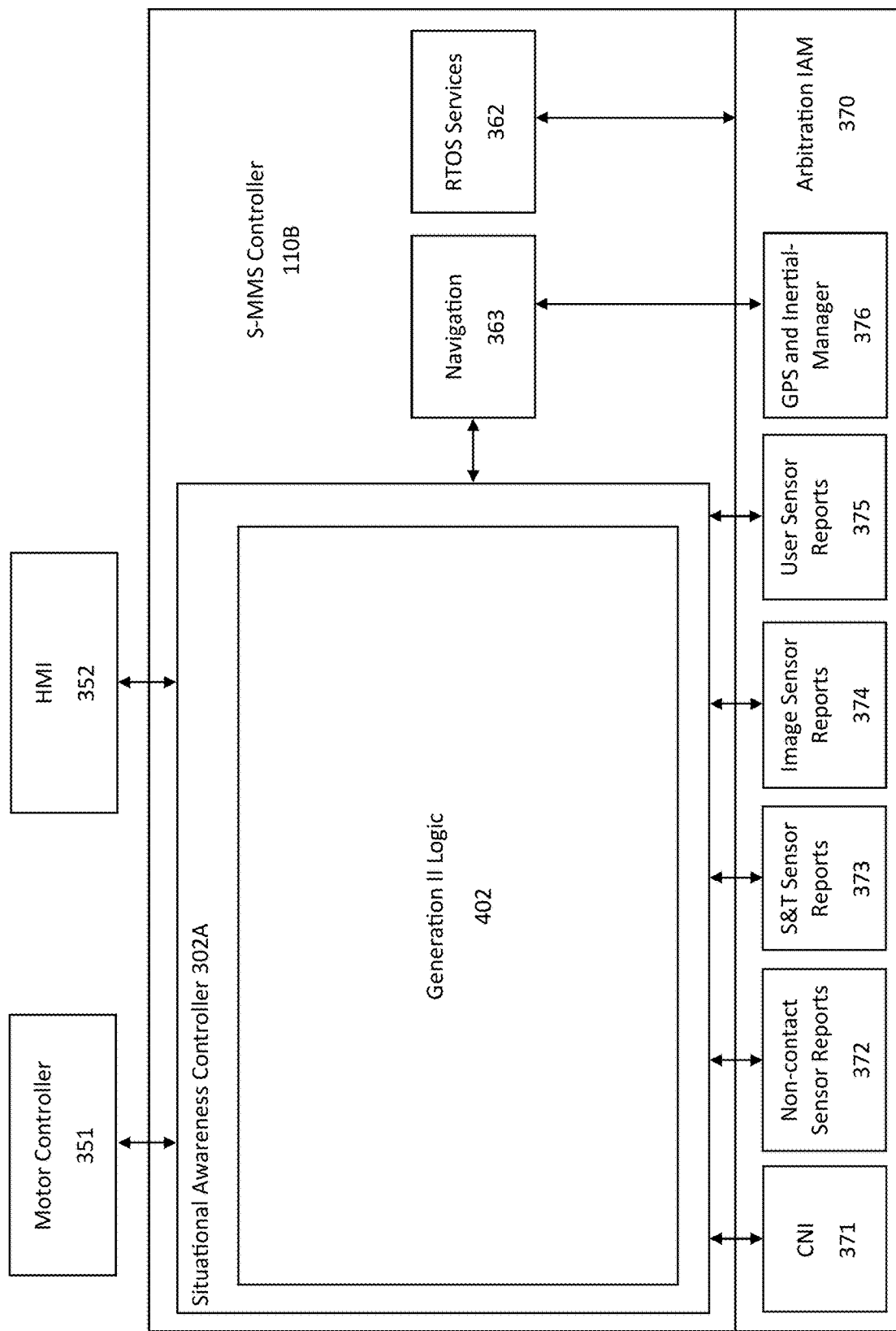
FIG. 4 depicts an embodiment of a control system architecture for an S-MMS with a situational awareness controller.

FIG. 4 illustrates an embodiment of a system in which logic 402 for one or more architectures, including one or more generations referenced above, is deployed on the control system architecture depicted in FIG. 3. The logic 402 may take full advantage of the entire suite of sensors available in the depicted control system embodiment and/or other sensors not depicted. The logic 402 processes reports and other data from smart sensors, including smart non-contact sensors 372, search and track sensors 373, and image sensors 374. These sensors often have larger fields of view and may scan within these fields of view. These sensors may be able to characterize reports, i.e. generate both quantitative and qualitative attributes to sensor reports and coordinate sensor reports in time. These capabilities may be used to support data association techniques that can eventually be used in predictive systems.

The complexity and capability of the situational awareness controller 302 may dictate the types of applications it will support. In one example, the logic 402 supports simple applications, like tip detection, drop off detection, and/or function override for safety. In another example, the logic 402 supports user assistance systems that will result in a workload reduction for both the user and/or caregiver. In another example, the logic 402 supports increased user independence due to increased confidence in system actions.

Figure 5:
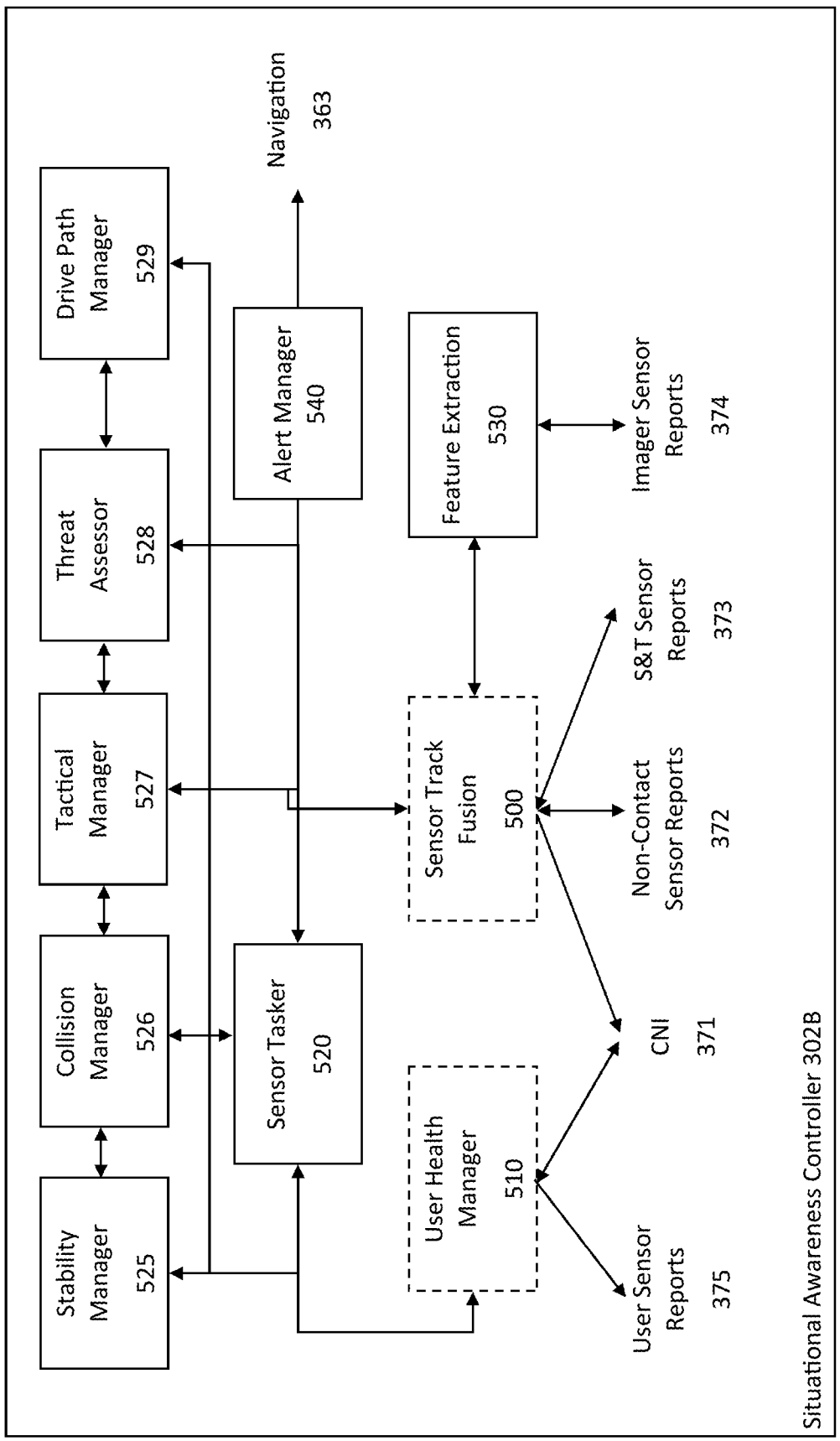
FIG. 5 depicts an embodiment of a situational awareness controller.

FIG. 5 depicts an embodiment of a situational awareness controller 302B that may be deployed in the architecture described by FIG. 4. The embodiment comprises a sensor track fusion 500, a user health manager 510, a sensor tasker 520, a stability manager 525, a collision manager 526, a tactical manager 527, a threat assessor 528, a drive path manager 529, a feature extraction 530, and an alert manager 540. These processes interact with the CNI 371, non-contact sensor reports 372, S&T sensor reports 373, image sensor reports 374, user sensor reports 375, and navigation 363.

Sensor track fusion (STF) 500 is responsible for processing, filtering, and reporting detections of one or more areas around an S-MMS 18 (e.g. between 0 and 360 degrees from a point or location on the S-MMS 18, 360 degrees around an S-MMS 18, and/or one or more overlapping areas from or around the S-MMS 18). This is accomplished by processing reports from the available sensors 371-375 and/or feature extraction 530. Next, recursive filtering (e.g. in one embodiment a Kalman filter) is used to estimate the state of each track based on the processed reports (e.g. 371-375, 530) in combination with one or more kinematic models (e.g. algorithms or mathematic equations) of possible track motion, for example, to determine if the track is in motion or stationary relative to the S-MMS. The estimate is compared to the state of each previously identified track maintained by the tactical manager 527 of the SAC 302B. If the STF 500 determines there is a high-quality match, the state of that track is updated in the tactical manager 527. If not, a new track is generated and communicated to the tactical manager 527. Upon track generation, a priority may be established based on time to impact by the threat assessor 528, and additional sensor data may be requested by transmitting a tasking request to sensor tasking 520.

Sensor fusion is the combining data from two or more sensors for the purpose of improving data quality and/or performance. In the embodiment depicted in FIG. 5, the boxes around the sensor track fusion 500 and user health manager 510 are dashed to indicate that all processes are historically based. These processes are focused on the creation of tracks and associating current sensor readings in ways that increase the confidence in the parameters (e.g. such as range and bearing) of those tracks.

The systems herein are predictive systems, wherein the sensor track fusion 500 and user health manager 510 processes may be enhanced based on one or more of:
- a prior knowledge of state,
- a prediction step based on a physical model,
- where measurements are made and compared to the measurements, and,
- an update step is performed that is either:
  - recursively used as a state transition model becoming the next prior knowledge of state, or
  - an output estimate of state for the next step.

This approach allows the S-MMS 18 to predict ahead of measurements an amount of time such that when an output estimate of state is generated, the system acts at $T_0$ or $T_k$ from $T_{k-1}$. Essentially, the estimate of state at time step k before the $k^{th}$ measurement has been taken into account along with the difference between the state transition step and the predicted step in uncertainty. Uncertainty, for the purpose of this disclosure, may be a parameter, associated with the result of a measurement, that characterizes the dispersion of the values that could reasonably be attributed to the measurement. In lay terms, the prediction of state is at some probability of accuracy surrounded by some uncertainty. At some point, the predictions are within the estimates and actions may be taken, essentially at time $T_0$.

The sensors used with the disclosed control system may operate with large fields of view (FOV). These FOVs may typically be in the 30 to 120-degree range, in some embodiments. Larger FOVs reduce the number of sensors needed to achieve situational awareness of the S-MMS 18. In some embodiments, two or more sensors operate in overlapping zones of coverage. This overlap allows sensor reports for a single track, condition, or object to be generated by more than one sensor and/or sensors of different types.

A user health manager (UHM) 510 is responsible for processing, filtering, and reporting changes in user behavior and/or health that may be relevant to the situational awareness controller 302B of the S-MMS. Data from user sensor reports 375, CNI 371, and/or HMI inputs 352 (FIG. 4) are used by the UHM 510 to monitor individual and combined health metrics. The UHM 510 then determines the appropriate timeline for any S-MMS controller 110B intervention or adjustments to SAC 302B behavior. The UHM 510 may further access a user profile and log user data to secure memory linked to the user profile.

A sensor tasker (ST) 520 responds to sensor information requests from sensor track fusion 500 and sensor information prioritizations from the threat assessor 528. These priorities are used by the sensor tasker 520 to change sensor update rates for possible unsafe conditions (e.g. such as collisions or tipping danger) and to manage sensor front-end resources to maintain the highest quality tracks on the closest detections. A track is a threat to the S-MMS 18 that has been identified by the SAC 302B and given a unique identifier for use in future calculations and processes. The sensor tasker 520 may act as a filter and utilizes the S-MMS system kinematic and identity information for decision making based on predefined decision boundaries to control the amount of sensor data provided to the SAC 302B at a given instant.

A stability manager 525 determines the stability of the S-MMS 18 and whether the upcoming ground is likely to cause instability (e.g. tipping) based on one or more inputs from navigation 363, sensor track fusion 500, and/or threat assessor 528. The stability of the S-MMS 18 is calculated based on orientation readings (e.g. pitch and/or roll) received from navigation 363 (e.g. from one or more inertial measurement units fixed to the S-MMS) in combination with a mathematical tipping model for the S-MMS 18 stored in memory and executed by the stability manager 525. The stability manager 525 also determines the suitability of upcoming terrain based on factors, such as topographic profile and/or surface composition as measured by one or more sensors 371-374 in relation to current S-MMS 18 operation characteristics, such as orientation and S-MMS kinematics (e.g. rate of travel, direction of travel, and S-MMS configuration settings). In an example, an S-MMS 18 may have known limits for pitch and roll where tilting beyond the known limits causes the S-MMS to tip. Based on the current orientation (e.g. pitch and/or roll) of the S-MMS, the stability manager 525 may use readings of the ground slope around the S-MMS to estimate the future pitch/roll of the S-MMS if it travels further forward. If the pitch/roll is below a threshold, the action is allowable. If not, then the action is not allowable. A list of stability conditions and their location relative to the S-MMS 18 are provided to the tactical manager 527 for integration into the master threat assessment map. The appropriate timeline for any necessary steering actions and any future coupled steering maneuvers to minimize instability accidents may be computed by the stability manager 525. System cutoffs, emergency braking, and/or motor controller disengagement functions may be performed by this stability manager 525. The stability manager 525 may further include crash event data recording and logging for use in S-MMS system diagnostics, in some embodiments.

A collision manager 526 computes the Time to Impact (TTI) function based on one or more inputs from threat assessor 528 and sensor fusion 500. The TTI function uses received sensor data associated with one or more objects located around the S-MMS 18 in combination with the current state of the S-MMS 18 (e.g. heading, velocity, and/or acceleration) to estimate the time until a collision with those objects is anticipated. The collision manager 526 then determines the appropriate timeline for any necessary steering actions and any future coupled steering maneuvers to minimize collision accidents. Any system cutoffs, emergency braking, and/or motor controller disengagement functions may be performed by the collision manager 526. The collision manager 526 may further include crash event data recording and logging for use in S-MMS system diagnostics, in some embodiments.

A tactical manager 527 uses inputs from one or more of a stability manager 525, collision manager 526, drive path manager 529, navigation 363, threat assessor 528, and/or sensor track fusion 500 to maintain a master, 360-degree map of known objects and conditions in relation to the S-MMS 18. The tactical manager 527 combines the outputs of the stability manager 525 (e.g. a map of the ground surrounding the S-MMS) and collision manager 526 into a single, integrated map of known tracks. Each track may be assigned a threat level by the threat assessor 528. The current direction and speed of travel (e.g. from navigation 363) and/or desired future direction and speed of travel (e.g. drive path manager 529) can then be overlaid on the threat assessment map maintained by the tactical manager 527.

A threat assessor 528 function evaluates the multiple tracks and/or objects detected by the SAC 302B processes, including the stability manager 525, collision manager 526, tactical manager 527, and feature extraction 530, and prioritizes them. Prioritization may be based on a rules engine. The rules engine executes one or more predefined rules as part of threat assessor 528. In one example, the rules engine uses a statistical assessment of the threat posed by each track and/or object based on the estimated time to impact to each track provided by the collision manager 526 in combination with the safe speed determined in the direction of travel provided by the stability manager 525 and/or drive path manager 529. If an identified track presents a statistical risk above a predefined threshold, the threat assessor 528 will prioritize that track above other tracks with lower calculated risk numbers. The prioritized list of tracks from the threat assessor 528 is sent to the sensor tasker 520 which may take additional readings or otherwise focus sensor resources on the highest threat tracks. Additionally, the prioritized list of tracks from the threat assessor 528 may be sent to the tactical manager 527 so that areas with a high concentration of high threat tracks may be flagged as keep-out zones.

A drive path manager (DM) 529 is responsible for route determination, interpretation of external map data (e.g. received from external sources such as a remote server or smart device via CNI 371) for future advanced routing functions, and generation of steering actions for autonomous by wire speed sensitive steering support. External map data, when received, must be oriented to match the S-MMS 18 reference frame by the DM 529 so that it can be used with the threat assessment map maintained by the tactical manager 527. The DM 529 combines one or more inputs from the tactical manager 527, sensor track fusion 500, threat assessor 528, and/or navigation 363 in order to determine where the S-MMS 18 should drive. The DM 529 contains a complex 6-DOF S-MMS 18 model that may be used in predictive applications to support stop and go functions, in some embodiments.

Feature extraction 530 performs angle resolution, object detection, edge detection, and bore sight correction for the S-MMS 18. Angle resolution is the process of determining the location and error of the orientation of a feature (e.g. object, edge, surface, or plane) around the S-MMS 18. Bore sight correction is the process of correcting downrange measurements for sensor misalignment. The sensor tasker 520 receives raw data of one or more image sensors via the image sensor reports 374, uses pixel masks from the sensor tasker 520, produces a detection report by applying one or more pixel masks to one or more image sensor reports, and assigns a unique identifier (identity) and kinematic data to each track identified in a detection report for sensor track fusion 500 consumption. Pixel masks are used to filter out or obscure areas of an image that are not of current concern to the SAC 302B process in order to decrease compute time and resources required for the process. In some embodiments, feature extraction 530 may be used in a similar way by the user health manager 510 to measure user health metrics.

In some embodiments, an alert manager 540 may be hosted on (e.g. executed by) the SAC 302B, one of the SAC processors (FIG. 2), and/or hosted in one or more of the application spaces 125 and/or 130 (FIG. 1).

In an embodiment, the alert manager 540 responds to inputs from stability manager 525, collision manager 526, drive path manager 529, and/or STF 500 to alert the user to possible dangers, enabling a warning, caution, or advisory to actually come from the direction of the problem. For example, the alert manager 540 of the SAC 302B generates one or more signals to one or more speakers on or around the S-MMS 18 causing the one or more speakers to produce one or more sounds that are either generic or particular to the particular speakers (e.g. one sound for a right lateral speaker to notify the user of an alert on the right lateral side of the S-MMS, another sound for a left lateral speaker to notify the user of an alert on the left lateral side of the S-MMS 18, another sound for a forward speaker to notify the user of an alert in front of the S-MMS, and another sound for a rear speaker to notify the user of an alert behind the S-MMS). This alert manager 540 may receive and process data from the collision manager 526, the stability manager 525, and/or the UHM 510, such as timing for predicted collision, instability, or user health issues, and coordinate one or more alerts with the time for the predicted collision, instability, or user health issue for crash mitigation or condition avoidance. This timing may be based on expected user reaction times and user health considerations. In some embodiments, an audio alerting function or 3D audio is implemented. When an obstacle or dangerous condition is detected, one or more sounds are produced from the direction of the threat by one or more speakers installed on or around an S-MMS 18.

In one embodiment, the necessary speakers are integrated as part of the HMI and controlled by the HMI processor 208 (FIG. 2). Other embodiments may alternatively or additionally include visual, haptic, or biofeedback mechanisms to provide a corresponding feedback.

The alert manager 540 may also alert the user to degraded systems that require maintenance to keep systems operational. One example of this is integration of LED lights on each sensor or associated with each sensor processor 214 (FIG. 2). In this example, the alert manager 540 monitors the status of the sensors (e.g. by receiving a status signal from each sensor) and transmits a signal to each sensor LED when that sensor fails causing the LED to turn on and notify users and technicians of a failed sensor. In one example, the sensor status signal is either an on state (positive voltage signal) or an off state (no voltage). The alert manager 540 may receive multiple types of status signals from the sensors and/or other devices of the S-MMS 18 and transmit one or more signals to one or more status indicators (e.g. single or multi colored LED or other visual, audio, or signal indicator) to cause to indicator to alert the user, technician, or other person as to the status of the sensor or other device. These "Clean Lights" or other indicators may also be clustered in a central display as part of the HMI 352.

Figure 6:
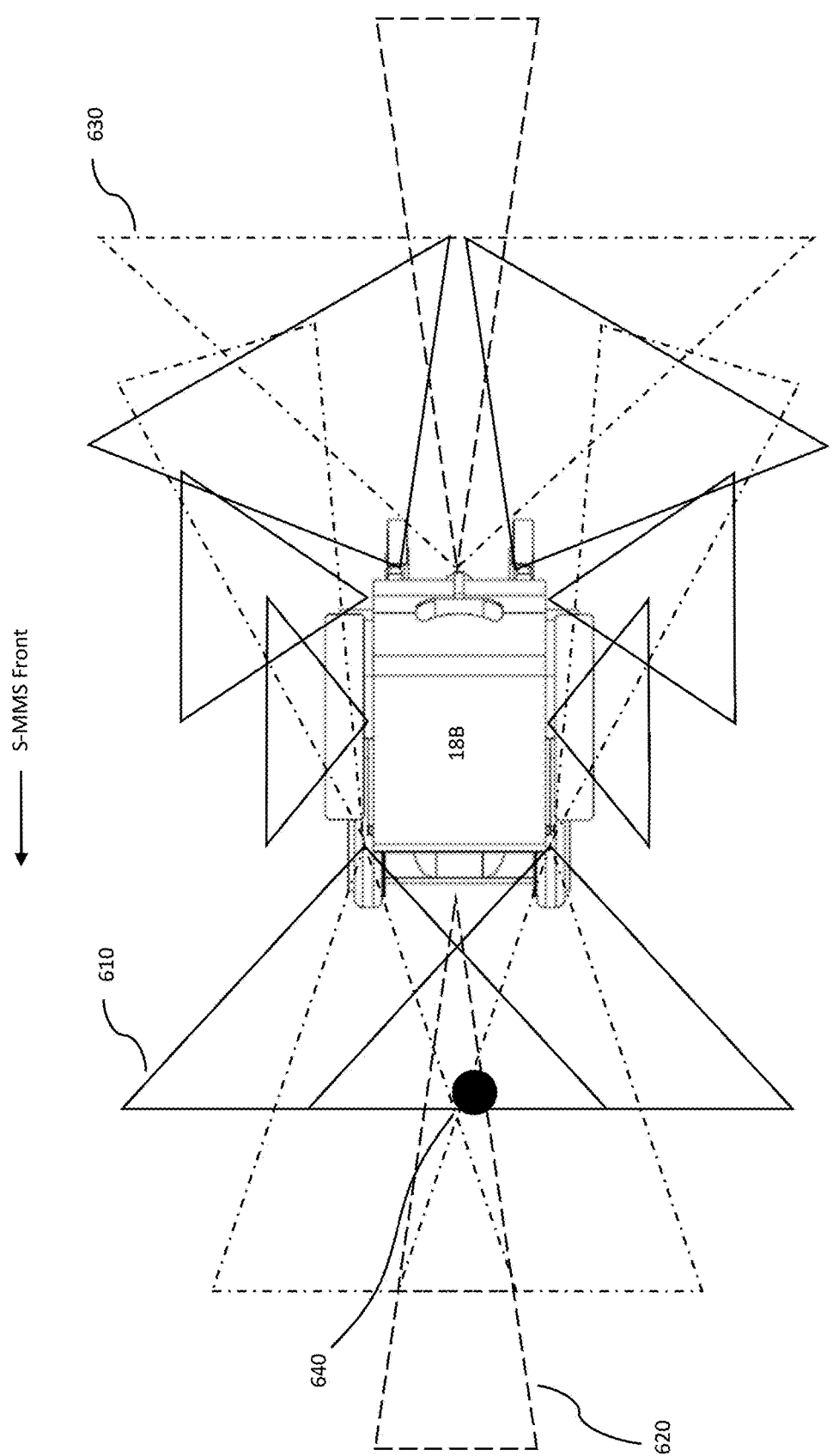
FIG. 6 depicts an embodiment of a sensor system.

FIG. 6 depicts a front-wheel drive S-MMS 18B equipped with an embodiment of sensor arrays to cover three main types of sensor coverage zones, including zones 610 (zones with solid lines), zones 620 (zones with dashed lines), and zones 630 (zones with dash-dot lines). The depicted sensor coverage zones 610, 620, 630 are covered using three main sensor arrays, including five forward sensors, five rearward sensors, and six side sensors (three for each side) generally aimed to cover the range of motion of the S-MMS 18B and toward the blind spots of a user. The sensors may be arranged to take readings on the area proximate to the S-MMS 18. Additionally or alternatively, the sensors may be arranged to take readings on the terrain (e.g. ground) proximate to the S-MMS 18. The depicted sensor arrays are composed of a mix of (a) short-range sensors such as short-range LIDAR, SONAR, and RADAR sensors for zones 610 with solid lines, (b) long-range sensors such as long-range LIDAR and RADAR sensors for zones 620 with dashed lines, and (c) image capturing sensors (including still images and/or video, referred to generally as imagers) such as cameras for zones 630 with dash-dot lines. Generally, short-range sensors have wider fields of view (FOV), while long-range sensors have narrower fields of view. The sensor array of FIG. 6 may be characterized as an overlapping, large FOV (with both narrow and wide FOVs), sensor array. The sensor placement, number of sensors used, and types of reports expected in the depicted embodiment are used as a non-limiting example. It should be clear that more or fewer sensors of varying types may be used.

One or more single sensor units may have the ability to act in both short and long-range modes. One or more single sensor units may have the ability to measure objects and measure or map the terrain proximate to the S-MMS 18. One or more sensors and sensor types may be selected for a desired S-MMS 18 architecture and user. As an example, if the user is a quadriplegic and spends most of their time indoors in a relatively slow-moving S-MMS, the sensor arrays may be comprised of all short-range sensors, with multiple overlapping FOVs, where the time to impact on a close-in maneuvering object is much more critical than a vehicle on the horizon. Alternatively or additionally, the sensor array would be adjusted if fitted to alternative drive configurations such as a center or rear-wheel drive S-MMS.

When working with an overlapping, large FOV, sensor array, Multiple Object Tracking (MOT), or Multiple Target Tracking (MTT), techniques may be used. For example, a threat assessor (TA) function 528 (FIG. 5) of the SAC 302B is responsible for locating multiple objects, maintaining their identities, and calculating their individual trajectories given sensor input data (e.g. sensor reports 372-374). Objects to track can be, for example, pedestrians on the street, vehicles in the road, sport players on the court, obstacles or features of the ground, surface conditions of upcoming terrain, or animals. Further, multiple "objects" could also be viewed as different parts of a single object. This is the situational awareness map or tactical awareness map (e.g. a map and/or an identification of the ground, conditions, surfaces, and/or objects surrounding the S-MMS) maintained by the tactical manager 527.

Figure 7:
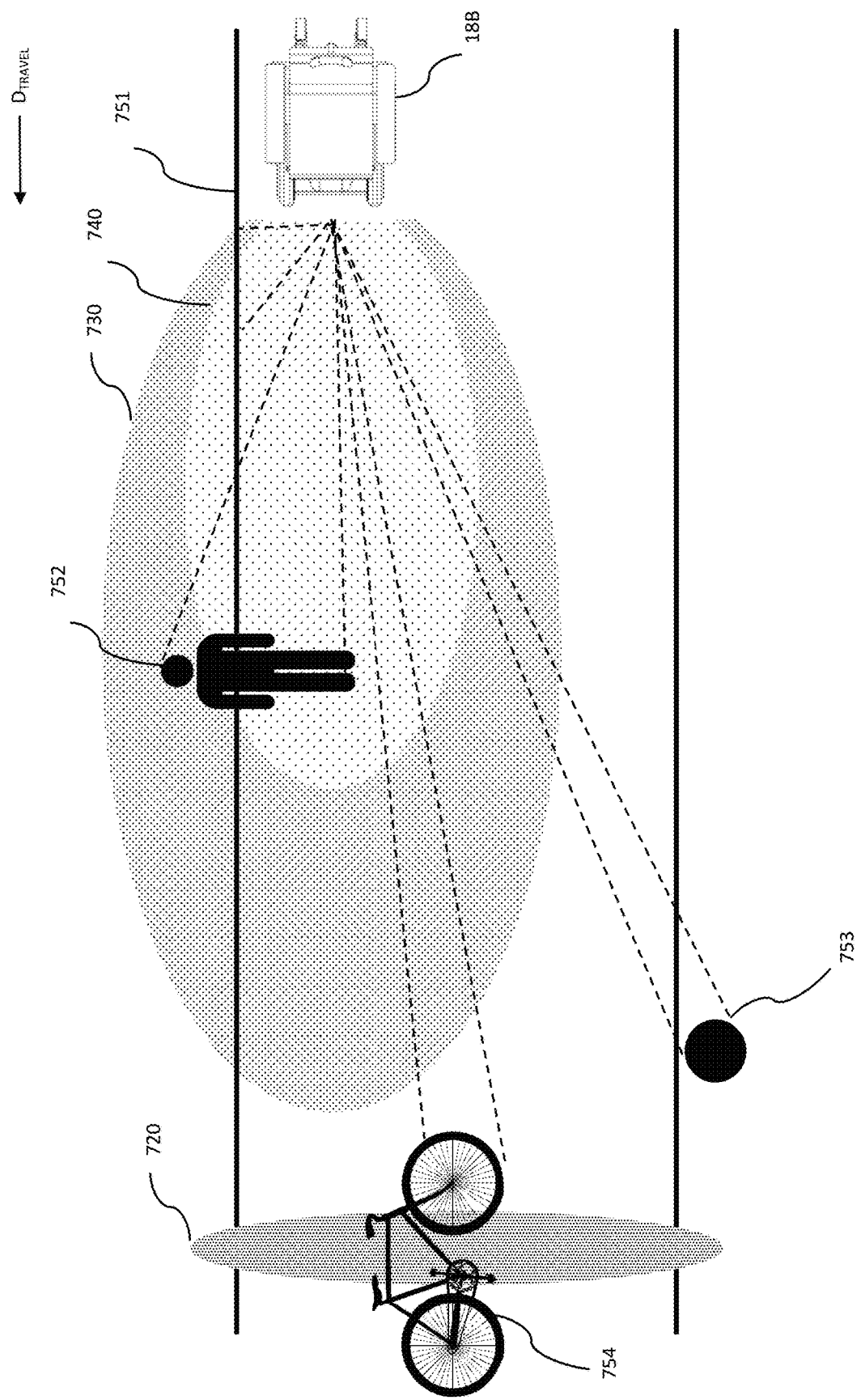
FIG. 7 depicts an example embodiment of 360-degree situational awareness.

FIG. 7 depicts an example of 360-degree situational awareness. Multiple objects may be present at any given time, arranged around the S-MMS 18B at varying distances from the user. These objects may include features such as a curb or drop 751 in the ground that could be dangerous to stability, moving objects such as a person 752 or bicycle 753, and stationary objects such as a lamp post 754. The S-MMS 18B may become aware of objects in the distance 720, yet not be able to confidently identify the objects until they are in range or more information can be gathered. For instance, the S-MMS 18B may not be able to confidently differentiate a bicycle 753 from a motorcycle when it is a long distance 720 away. Objects in midrange 730 may be more easily recognizable, and object identity may be qualified and quantified. "Quantify" refers to the determination of aspects such as range, bearing, location, velocity, and acceleration, i.e. the kinematic state of an object. In close proximity 740, the SAC 302 (FIG. 3) may generate threat/collision data/information. "Close" may be assessed in terms of time to impact, distance, and/or general threat.

In practice, the zones depicted in FIG. 7 extend 360-degrees around the S-MMS 18B. Each side may have varying degrees of need for the size and placement of the zones dependent on several factors, including S-MMS dynamics, which in turn may dictate the number and type of sensors required, in some embodiments. The depicted zones are for example purposes only and may vary between embodiments depending on sensor types, number of sensors, sensor ranges, characterization data, historical data, and other related systems, devices, and information/data.

Uniform Cartesian Grid

The SAC 302B, in some embodiments, is a tactical manager that operates in a uniform way at a systems level with all of the sensors, data, time, etc. coordinated into a unified system. Some difficulties in uniform operations include that target reports from the sensors are typically in polar coordinates (e.g. range and bearing) to a target from the center of the sensor aperture or receptor, that the sensors are mounted at distributed points on and around the S-MMS 18 to achieve the best fields of view, and that processing time, sweep rate, communications time, and other sensor operating parameters may vary with each sensor. The frames of reference for each sensor can be identified and described in terms of their relationship to each other and their functional roles. These difficulties may be overcome using the following methods.

There are five frames of reference in an S-MMS 18 sensor system, where the S-MMS 18 is designed to navigate the real world. These frames of reference are:

1. Sensor Frame.
2. MMS Frame.
3. Navigation Frame.
4. Earth Frame.
5. Geo Frame.

Figure 8:
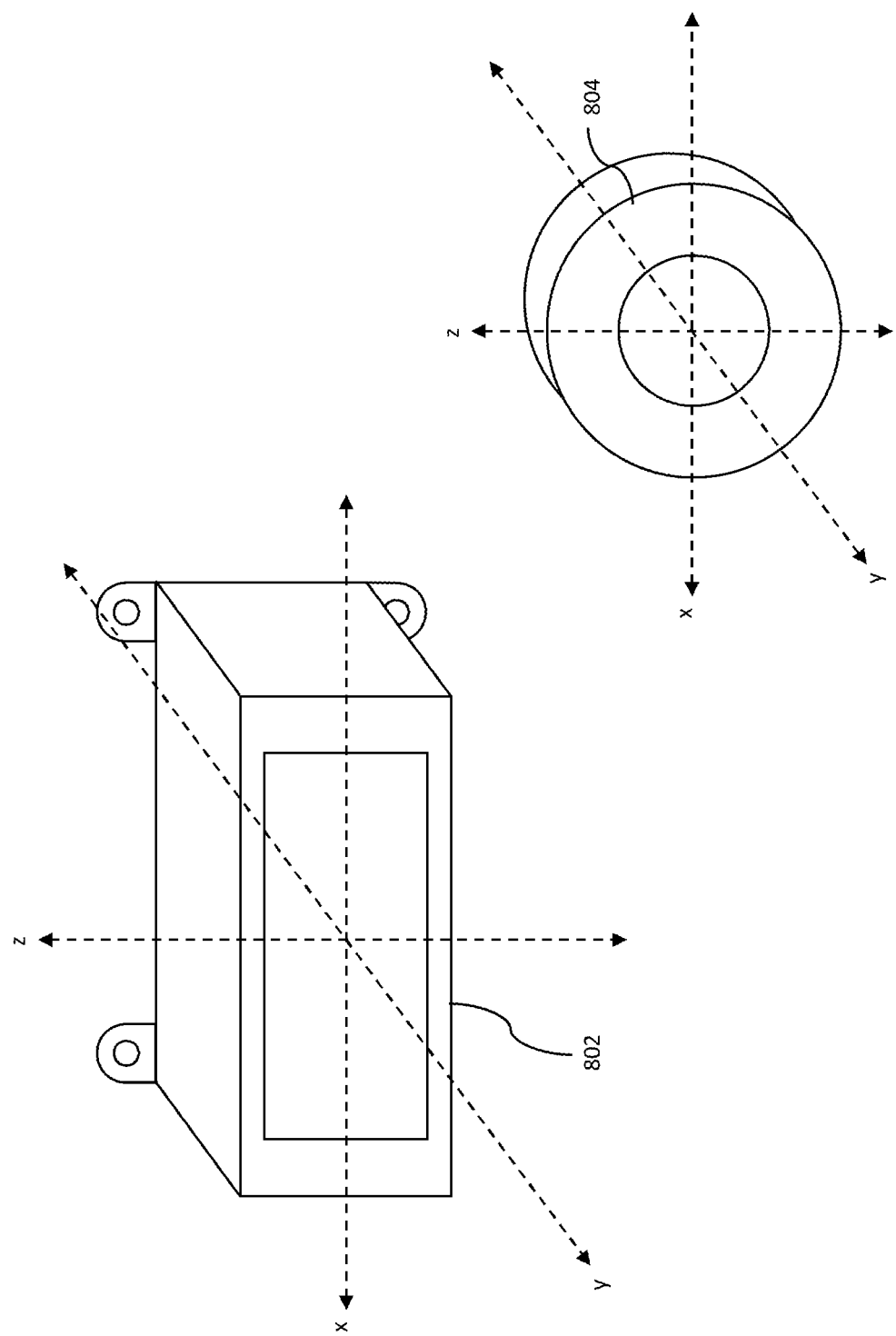
FIG. 8 depicts reference frames of typical sensors.

A sensor frame extends from the center of an aperture or receptor (e.g. lens, antenna, etc.) of the sensor. FIG. 8 depicts typical sensors 802, 804. In the depicted embodiment, the x-axis of each sensor extends orthogonal to the direction of travel and indicates roll attitude, the y-axis of the sensor extends in the direction of travel and indicates the pitch axis, and the z-axis of the sensor extends vertically through the center of the sensor and indicates the yaw.

Figure 9:
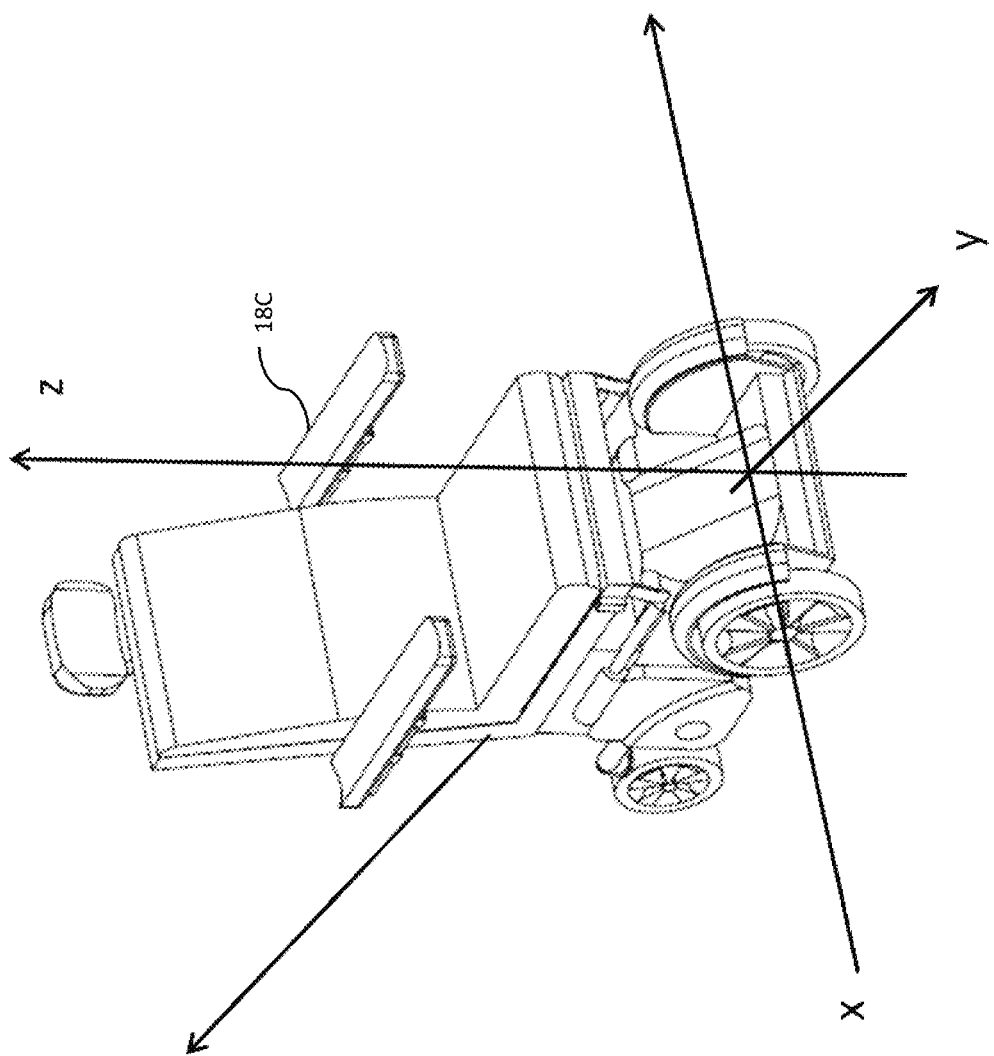
FIG. 9 depicts an S-MMS frame of reference.

FIG. 9 depicts an exemplary mobile chair S-MMS 18C frame of reference. In the depicted embodiment, the x-axis extends from left to right of the mobile chair S-MMS 18C and is parallel to the front of the mobile chair S-MMS, the y-axis is perpendicular to the x-axis extending forward in the direction of travel, and the z-axis is orthogonal to the x and y-axis and vertical through the intersection of the x and y axes. As with the sensor reference frames, x, y, and z-axes represent roll, pitch, and yaw measurements.

In some embodiments, an S-MMS 18C may have multiple frames of reference, one of which may be considered the master frame of reference. As an illustrative example, the S-MMS 18C may have suspended assemblies (such as wheel cowlings) that move relative to the S-MMS frame itself. If a sensor were mounted on a suspended assembly, then the motion of the suspension would need to be accounted for when translating a sensor frame of reference to the master frame of reference.

Figure 10A:
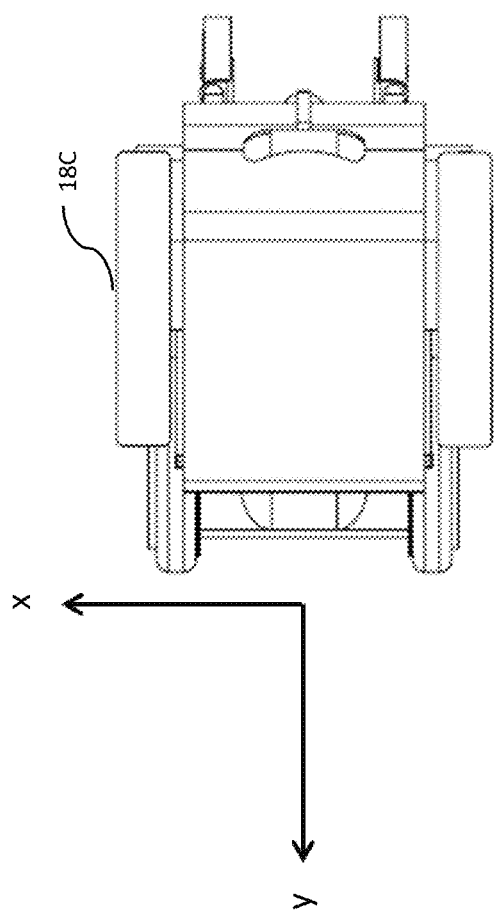
FIG. 10A depicts a navigation frame of reference.
Figure 10B:
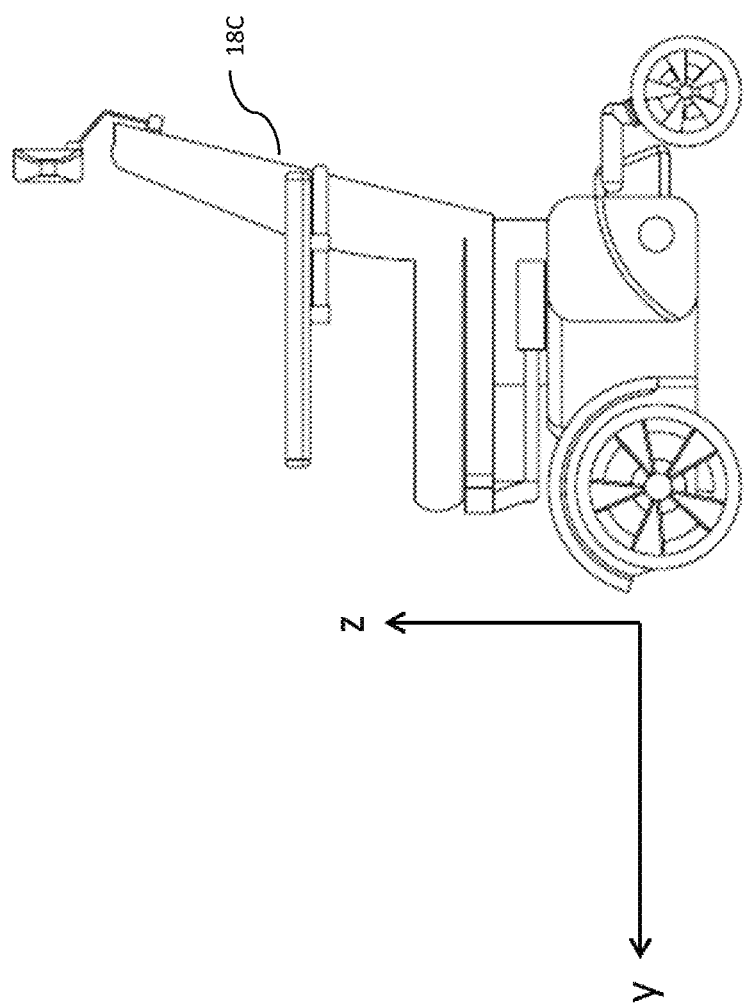
FIG. 10B depicts another view of the navigation frame of reference of FIG. 10A.
Figure 10C:
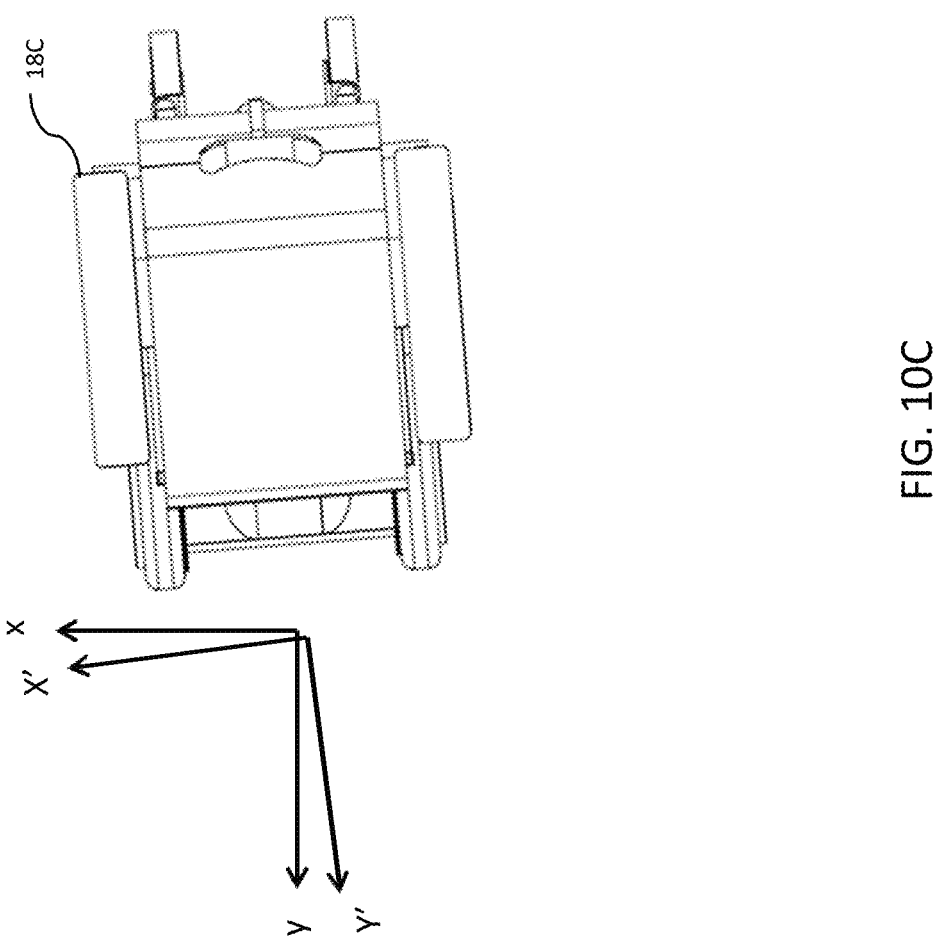
FIG. 10C depicts an actual navigation frame of reference and a perceived navigation frame of reference.
Figure 11:
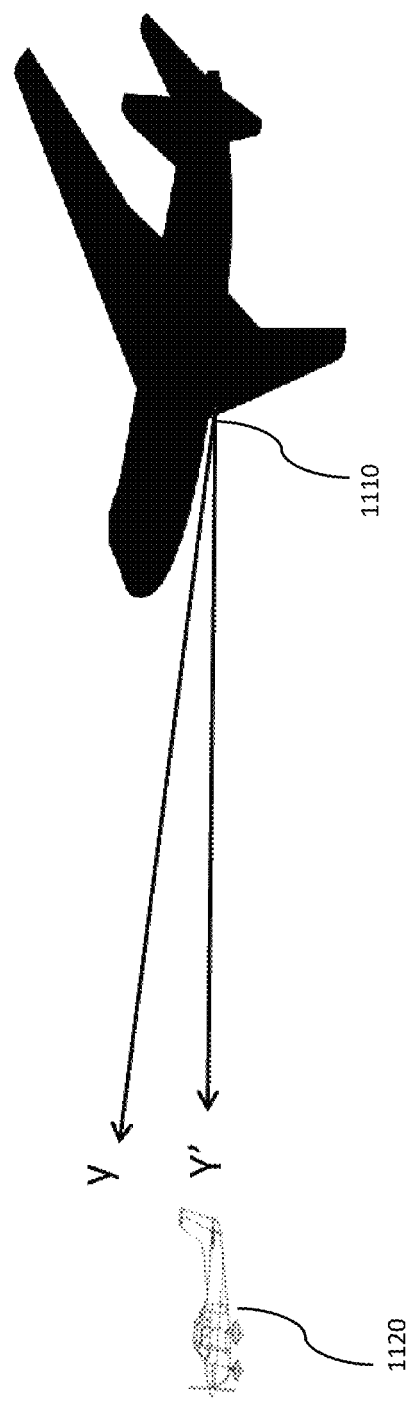
FIG. 11 depicts an embodiment of an actual navigation frame of reference that deviates from a perceived navigation frame of reference.

FIGS. 10A-10C depict an exemplary navigation frame of reference overlaid on a mobile chair S-MMS 18C. The navigation frame of reference relates to how an S-MMS 18C is traveling in its environment. FIGS. 10A and 10B depict an exemplary navigation frame of reference. FIG. 10C depicts a situation in which the actual navigation frame of reference and the sensor frame of reference do not align due to error. In this scenario, the S-MMS 18C sees the world as x' and y'-axes, but in reality, the S-MMS travels in x and y-axes. In this example, x and y-axes are the actual navigation frame, regardless of what the sensors detect. As an analogy, FIG. 11 depicts an airplane 1110 traveling through the air. The pilot of the airplane 1110 thinks it is traveling along a y-path when in reality it is traveling along a y'-path. Regardless of the sensor reports along the y-path, the plane 1110 is traveling along the y'-path. If an object like a small plane 1120 is in the true navigation frame of the plane 1110, there will be a collision. An understanding of this principle is important to safety and object avoidance. The reported data from sensors reporting along a y-axis of an S-MMS 18C frame, and/or other sensor frames, will be different in the navigation frame as described. The SAC 302B tactical manager 527 properly associates objects and conditions reported by sensors (371-376) with the true navigation frame of the S-MMS 18C. Below, further systems and methods are disclosed for detecting and managing these frames.

The next two frames of reference are the earth frame and geo frame. The earth frame is in terms of latitude, longitude, and altitude as represented on a map. The geo frame is earth centered and earth fixed in terms of direction cosines. The intersection of these curved lines from the center of the earth represent where an object is located three dimensionally above or below the surface of the earth, as when traveling in an airplane or submarine. These two terms are sometimes referred to as the geoid and spheroid. Use of the geo frame and earth frame may be useful for navigating between floors on a multi-story building.

Altitude changes of the surface of the earth frame (e.g. terrain) are particularly important for safe and effective navigation of S-MMSs to avoid tipping and/or instability. The need of an S-MMS 18C to map and characterize terrain at a high accuracy is unique to S-MMSs compared to other types of vehicles.

Establishing the UCG

With focus on the first four frames of reference, a uniform way of receiving, using, and sharing information needs to be established. Sensor reports (372-375, FIG. 3) and external data (371, FIG. 3) may be received by the situational awareness controller 302B relative to different frames of reference. A method for managing this is to establish a uniform Cartesian coordinate system extending from the S-MMS 18C reference frame depicted in FIG. 9. All data received by the SAC 302B may be translated to the S-MMS 18C reference frame, where the earth reference frame is also referenced to the S-MMS 18C reference frame by navigation 363. Sensor reports received in polar coordinates (i.e. range and bearing to objects) are first translated into Cartesian coordinates by the SAC 302B through what is called a standard conversion, disclosed below. Then, those converted sensor reports may be translated by the SAC 302B into the S-MMS 18C reference frame and related to the earth frame.

Motorized mobile systems enable their users to navigate the world. They navigate and move in a distinct way, at a different speed, and occupy a very different footprint from the people or animals walking around them. This unique behavior, combined with the power and weight of the MMS, make awareness and avoidance of people, animals, and other things that move important to the safety of both the MMS user and those moving around it. As opposed to simply avoiding collisions like an autonomous vehicle, these systems need to watch for and avoid toes and tails. S-MMS 18 collision avoidance and navigation systems must be much more accurate than existing automobile systems and must take into consideration unique situations.

The uniform Cartesian grid (UCG) lays the foundation for creating a virtual situational awareness (SA), or tactical, map. The situational awareness map comprises objects, the kinematic states of these objects, and state propagation with respect to the user's S-MMS 18 and the objects in their environment. The threat map is constantly updating with data reported by onboard sensors (see FIG. 6), data reported by remote sensors via CNI 371, and data received via the internet or other external sources using one or more onboard communication processors 216, FIG. 2. The SA map may be maintained by the tactical manager 527 of the SAC 302B and allows the S-MMS 18 to calculate time to impact on proximate objects. The UCG becomes the single corrected frame of reference for all calculations on the SAC 302.

The S-MMS 18, as disclosed, uses sensors capable of making measurements with the lowest possible amount of error, or variance. Variance may be defined in terms of plus or minus in seconds, milliseconds, feet, inches, yards, degrees, radians, etc. Sensor measurements are used in support of a logic based S-MMS controller 110B system that may be inferenced by some form of adaptive learning that operates like intuition, as discussed further below. Two or more sensor reports on the same object that are different and can be associated in time may be combined to generate a better report, with the goal of improving confidence in the tactical map.

Referring back to FIG. 6, object 640, is covered by four sensors: two short-range LIDAR as designated by zone 610, one forward imager as designated by zone 630 and one long-range radar as designated by zone 620. A process is necessary for reconciling these multiple sensor reports (372, 373, and 374) on the single object 640 received by the SAC 302B. Preferably, this method would materially improve confidence in the accuracy of the system tactical map maintained by the tactical manager 527, thus improving situational awareness. As discussed above, the SAC 302B may implement a probability based system with an estimator.

Dual Mode Variance

Figure 12:
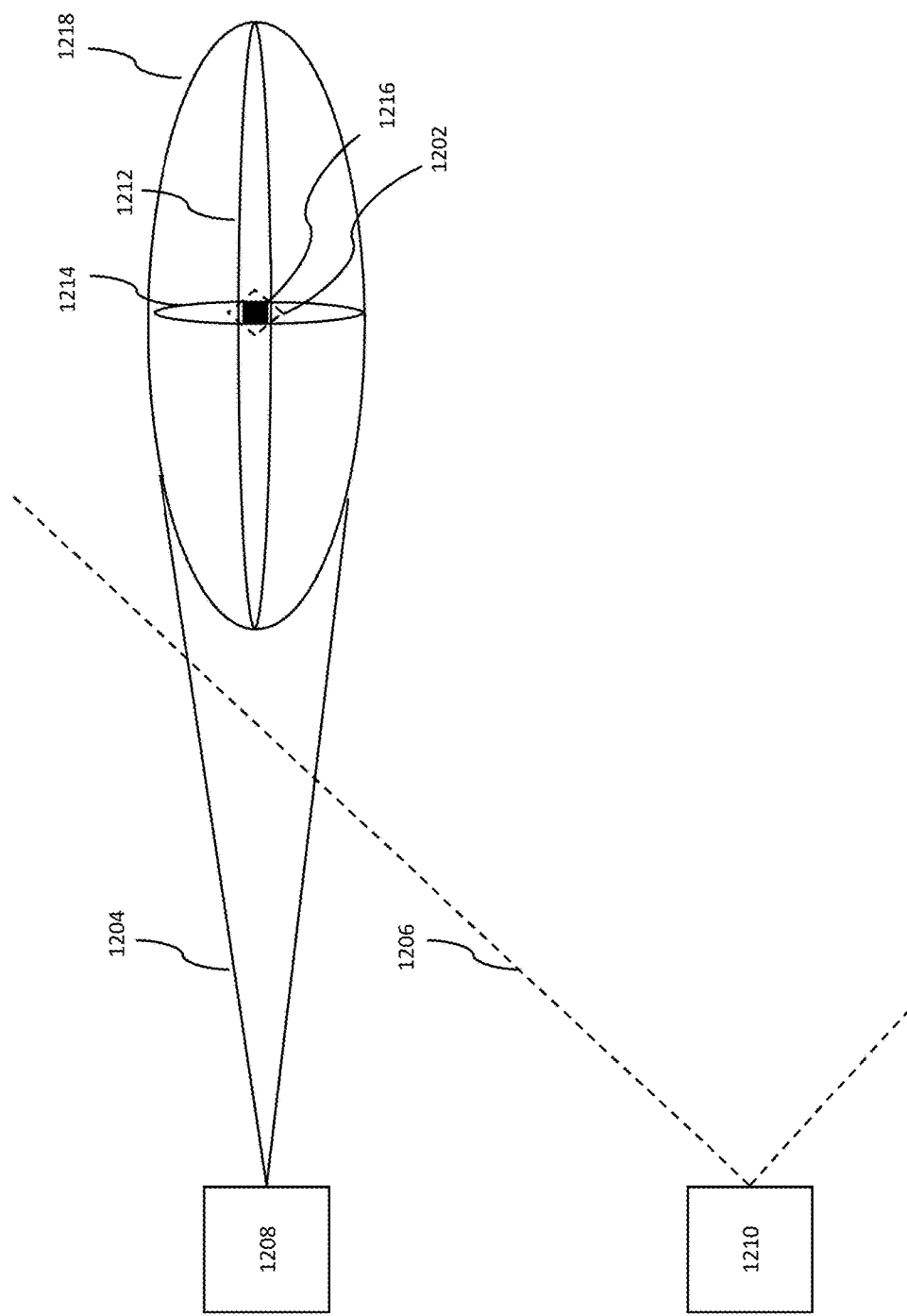
FIG. 12 depicts two sensors operating with different fields of view.

Dual mode variance is a method for improving confidence in the situational awareness map of the SAC 302. Dual-mode variance may be used to decrease uncertainty of any S-MMS 18 functions disclosed wherein two or more sensor reports (371-376), or readings from multiple modes on a single sensor, can be combined to decrease uncertainty. An approach is depicted in FIG. 12 and comprises a first object 1202, located proximate to a motorized mobile system 18, wherein the first object 1202 is in the field of view 1204, 1206 of at least two sensors 1208, 1210 associated with the motorized mobile system 18. In some embodiments, a first sensor 1208 generates data about the first object 1202, wherein the first object data is represented by one or more of a first range measurement and a first bearing measurement to the first object. A range, or down range, measurement is the distance of something to be located from some point of operation, typically defined by the sensor frame of reference. A cross range or bearing measurement is a direction expressed in degrees offset from an arbitrary true baseline direction, typically defined by the sensor frame of reference. The first range measurement may have an associated first uncertainty with the first range measurement, and wherein the first bearing measurement has an associated second uncertainty with the first bearing measurement. As a non-limiting example, the first sensor 1208, an imager for example, may provide good cross range or bearing measurements but poor down range measurements such that the first uncertainty is larger than the second uncertainty as depicted by zone 1212. A second sensor 1210 may generate data about the first object 1202, wherein the first object data is represented by one or more of a second range measurement and a second bearing measurement to the first object. The second sensor 1210, a radar for example, may provide good down range measurements but poor cross range measurements such that the second range measurement has an associated third uncertainty with the second range measurement, and wherein the second bearing measurement has an associated fourth uncertainty with the second bearing measurement, wherein the fourth uncertainty is larger than the third uncertainty as depicted by zone 1214.

These overlapping sensor reports may be coordinated in time and associated with a single object (a.k.a. track) by sensor track fusion 520 on the SAC 302B. The most accurate measurement from each sensor report (cross range from the imager and down range from the radar, in the example) may be combined to make the situational awareness map more accurate. This use of more than one sensor is referred to as dual mode variance. In order to accomplish this, a processor (e.g. S-MMS processor 202), may host one or more programs such as the SAC 302B of the S-MMS controller 110B to:

receive from the first sensor data about the first object 1202,
receive from the second sensor data about the first object 1202,
retrieve from memory 120 the range and bearing uncertainties associated with the data generated from the first sensor,
retrieve from memory 120 the range and bearing uncertainties associated with the data generated from the second sensor,
identify the lower bearing uncertainty from the second and fourth bearing uncertainty,
identify the lower range uncertainty from the first and third range uncertainty,
combine the measurements associated with the lower bearing uncertainty and lower range uncertainty to generate a new reduced area of uncertainty (e.g. 1216 as compared to 1218), wherein uncertainty refers to errors in physical measurements that are already made.

As an example, FIG. 12 depicts an embodiment comprising two sensors 1208, 1210 operating with different fields of view. Imager 1210 has a field of view of 120-degrees 1206, and is based on a 1920×1080 resolution camera. This equates to an accuracy of 16 pixels per degree (1920–pixels/120-degrees=16 pixels per degree). If the detection software (e.g. running on the sensor processor 214) has a cross range resolution of ±2 pixels for object detection, there is a cross range error of ±0.125-degrees on the image sensor reports 374 from the imager 1210 received by the SAC 302B. The down range error for the imager 1210 is reported by the camera manufacturer as half the distance to the target. If the detection software on the imager 1210 estimated the target at 100-meters, the down range error is ±50-meters. This results in a variance, or error envelope, that looks like 1212. If the second sensor is a radar 1208 with an associated field of view 1204 of 30-degrees and that is reported to have down range errors in the ±10-cm range, but cross range errors of ±3-degrees its error envelope is depicted as 1214.

If, for example, these two sensor reports 374 and 372 are received by the SAC 302B, associated with a single object (a.k.a. track) by sensor track fusion 520, and unchanging over the last 30-seconds, the confidence is high that both sensors 1208, 1210 are targeting the same object. In one embodiment, the tactical manager 527 places the reports on the situational awareness map, and the object's location is marked as somewhere in the field of uncertainty depicted by 1218. Alternatively, if dual mode variance is employed, the best (e.g. lowest variance) elements of each sensor 1208, 1210 readings are combined, and the object's location is marked as somewhere in the field of uncertainty depicted by 1216. This is a significant reduction in uncertainty of object parameters. Without application of the disclosed approach, the uncertainty of object parameters would be the combination of the maximum errors or variances 1218. This improvement is termed dual-mode variance, and any single sensor reports are termed single-mode variance (e.g. 1212 or 1214).

As another non-limiting example, a single radar using a dual-mode synthetic aperture may be used, where the fields of view have two operating modes, a short range wide mode and a long-range narrow mode. The sensor report in short range wide mode may have similar characteristics to the imager 1210 discussed in the first example (i.e. good cross range accuracy, but poor down range accuracy). The sensor report in long range narrow mode may have similar characteristics to the traditional radar 1208 discussed in the first example (i.e. poor cross range accuracy, but good down range accuracy). If two measurements are taken from the single dual-mode synthetic aperture sensor, one in each mode, the measurements can be combined by the SAC 302B using dual-mode variance to increase confidence in the properties of a given object.

The previous examples are presented for clarity and are not intended to limit the types of objects, sensors, or scenarios where dual mode variance may be utilized. The first and second sensors may be one or more of an optical sensor, a sound sensor, a hall effect sensor, a proximity sensor, and a time of flight sensor, including radar, sonar, ultrasonic, LIDAR, or a distance camera. An object may include one or more of a thing, person, animal, ground feature, and surface condition. Additionally or alternatively, applications may include combinations of bio-medical sensors to track user health 375, ground or terrain tracking sensors to monitor system stability 372-374, and/or S-MMS status sensors included as part of the motor controller 351 or HMI 352, among others. Additionally or alternatively, one or more of the sensors generating data about an object may be received from a second S-MMS 18 or remote sensor associated with the S-MMS 18.

Polar to Cartesian Conversion

Another method of improving situational awareness and increasing confidence in the situational awareness map is application of polar to Cartesian conversion techniques. An inertial measurement unit (IMU) may be attached to the frame of an S-MMS 18 so that it reports the absolute orientation, attitude, and heading of the S-MMS 18 to the S-MMS controller 110B via the GPS and inertial manager 376. These reports may then be used to support the navigation 363 function of the S-MMS controller 110B. Additionally, the IMU sensor reports may also be used by the S-MMS controller 110B and SAC 302B to establish a vehicle reference frame extending along the S-MMS axes, as illustrated in FIG. 9.

Having a vehicle reference frame is necessary in the move to smart sensors that generate target sensor reports in a polar coordinate system, where the sensor reports are not in terms of x, y, and z, but in terms of range and bearing. Moreover, these sensor reports are received based on one or more sensor reference frames (FIG. 8). Navigation 363 (FIG. 3) is responsible for maintaining the vehicle reference frame. The SAC 302B then translates data from sensor reports representing targets in the environment and other data into a uniform Cartesian coordinate system allowing a higher confidence in the determination of threats.

Figure 13:
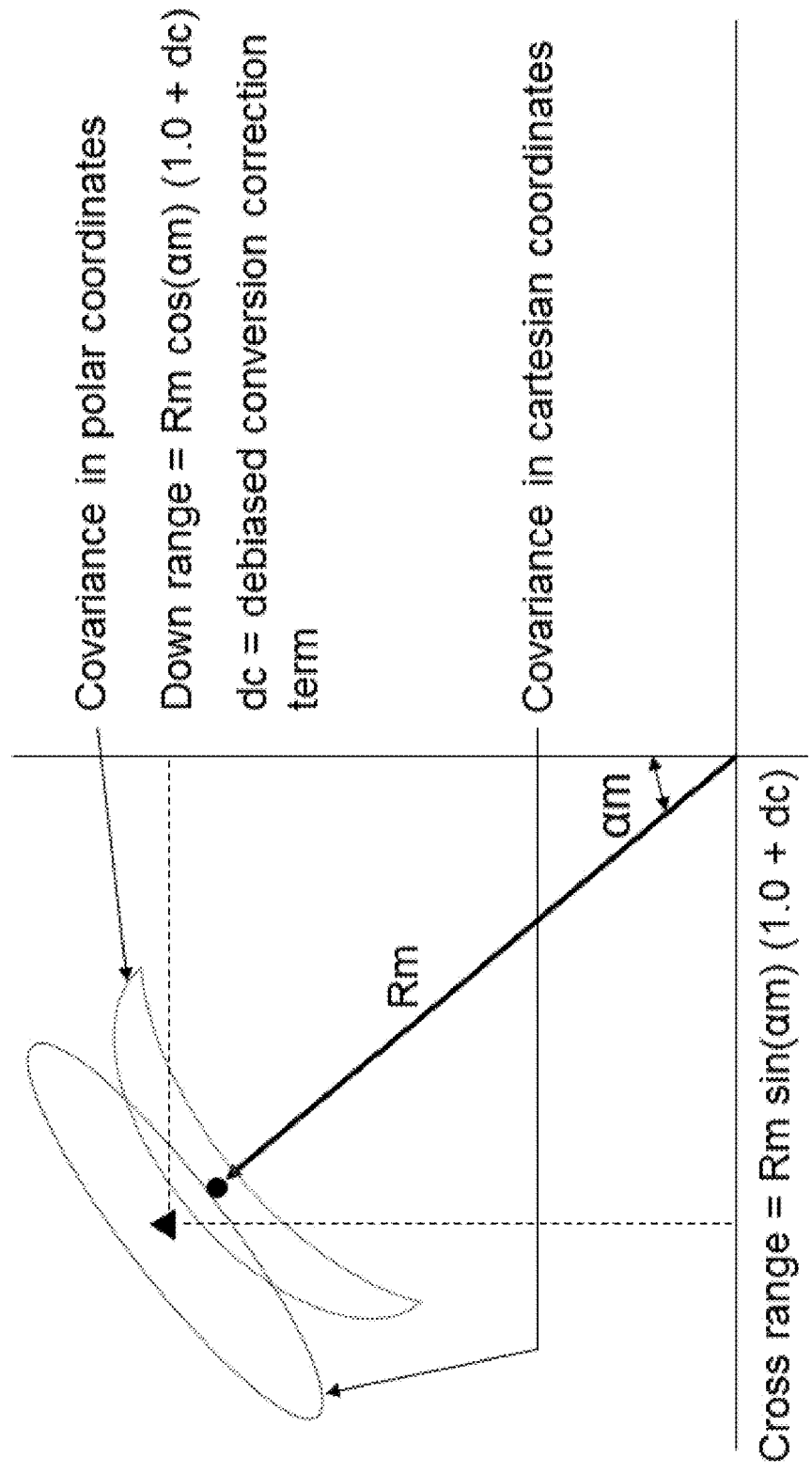
FIG. 13 depicts a standard conversion of error (variance).

As the sensor system evolves from single sensor reports to an integrated system of sensors, new issues arise, such as the capture and management of system error. In the example of axis translation as sited above, the polar translation may be completed in a standard conversion, as described in Equation 1:

$$x_m = r_m \cos \theta_m \text{ and } y_m = r_m \sin \theta_m, \quad \text{Eq. 1}$$

where $r_m$ and $\theta_m$ are the range and bearing, respectively, of the sensor target in the polar reference frame, and $x_m$ and $y_m$ are the down range and cross range coordinates, respectively, in the converted Cartesian reference frame. As an example, for a target at 10-meters, with a bearing of 1-degree, Equation 1 yields a Cartesian location of (9.99-meters, 0.17-meter) for (x,y). This conversion leads to some error. However, for the scenarios disclosed, the errors induced will be negligible. Additionally or alternatively, the SAC 302B may de-bias the variances of the polar reports when they are translated to Cartesian coordinates. A debiasing term may be used in the case that the standard Equation 1 cannot be used because they induce significant error. FIG. 13 depicts the standard conversion as well as the use of a debiased conversion correction term.

Cooperative Targeting

Cooperative targeting is another way of improving the situational awareness of the S-MMS 18. As stated earlier, the communication, navigation, identification (CNI) 371 (FIG. 3) function of the arbitration IAM 370 manages off-board communication for the S-MMS 18 through system links and off-board links to enable S-MMS 18 coordination. CNI 371 is also responsible for system wide time and processor time synchronization across the system in conjunction with the operating system of the S-MMS controller 110B.

Communication standards have been developed to support and enhance automobile communications known as vehicle-to-vehicle (V2V) or vehicle-to-infrastructure (V2I). The standards define an architecture and a complementary set of services and interfaces that collectively enable V2V and V2I wireless communications. Together, these standards provide the foundation for a broad range of applications in the automobile transportation environment, including automobile safety, automated tolling, enhanced navigation, traffic management, and many others. One standard was adopted as IEEE 1609 for Wireless Access in Vehicular Environments (WAVE) in the United States. The European Telecommunications Standards Institute (ETSI) Technical Committee Intelligent Transport System (ITS) developed and adopted a related set of standards, collectively called the ITS-G5. The WAVE and ITS-G5 standards are herein incorporated by reference in their entirety.

V2X communication is based on WLAN technology and works directly between vehicles or infrastructure, which form a vehicular ad-hoc network, as two V2X transceivers come within each other's range. Hence, V2X communication does not require any infrastructure to communicate, which helps to increase safety in remote or little developed areas. V2X is particularly well-suited for S-MMS 18 communication, due to its low latency and the ability to communicate instantly with no surrounding infrastructure. V2X transmits messages known as Common Awareness Messages (CAM), Decentralized Notification Messages (DENM), or Basic Safety Messages (BSM). Messages may contain a range of content, including the identity, type, and kinematic states of the entity containing each V2X transceiver.

Figure 14:
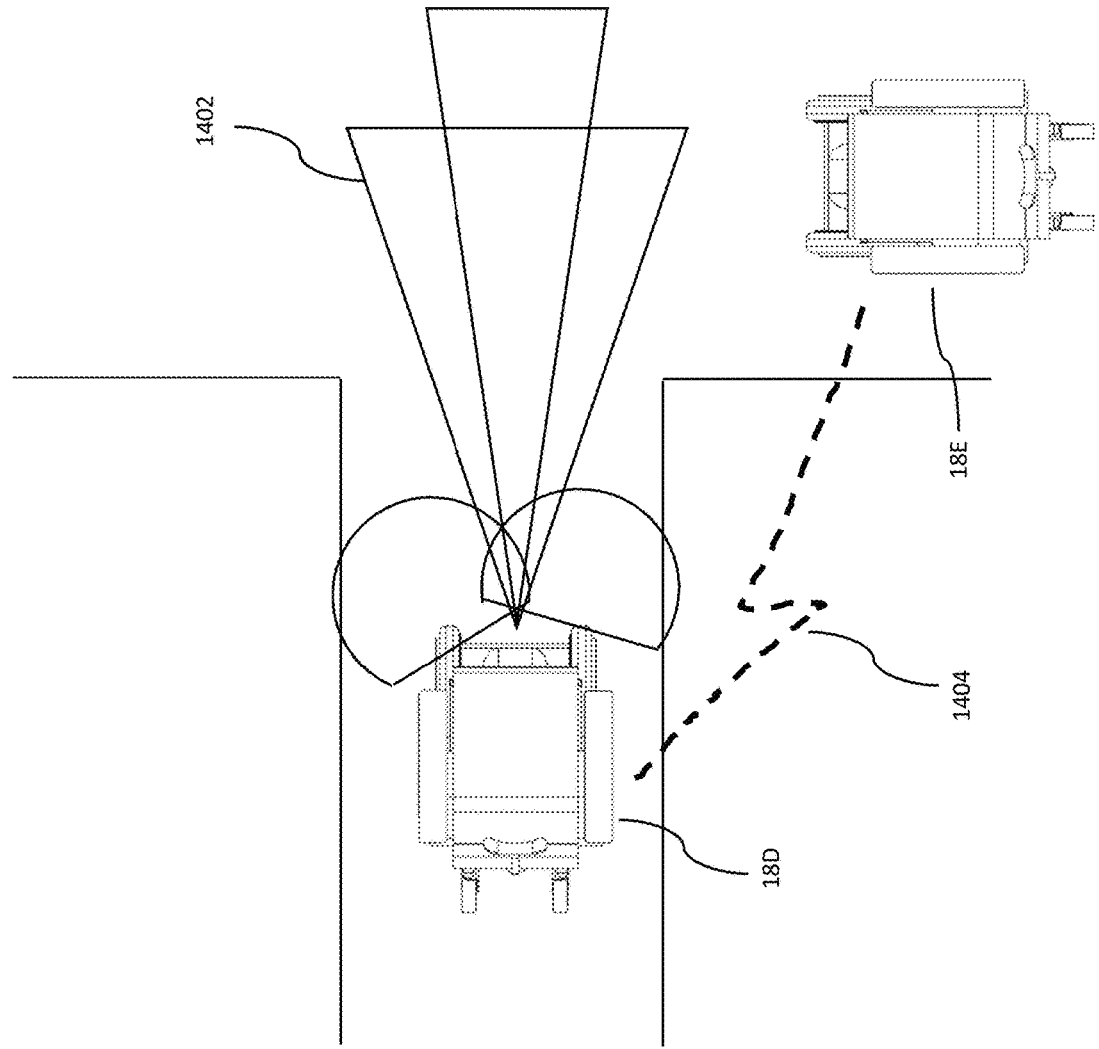
FIG. 14 depicts two S-MMS users approaching a blind intersection of two pathways.

FIG. 14 depicts two mobile chair S-MMSs 18D and 18E in communication with each other via an ad hoc network 1404. In an embodiment, the two S-MMS 18D and 18E may be configured to communicate with each other over a V2X network connection. The S-MMS 18D, 18E may be equipped with an 802.11P transceiver of the S-MMS 18 in communication with the communications processor 216 and the CNI 371 configured to manage 802.11P communications. In this way, the two S-MMSs 18D, 18E form a communication system comprising a vehicular ad hoc network for exchanging messages. The vehicular ad hoc system comprises a first security manager located in a portable first transceiver, wherein the portable first transceiver is one or more of proximate to the S-MMS 18D and physically coupled to the S-MMS 18D, linking data for transmission off-board to a second processor and second security manager associated with a second S-MMS 18E connected to the vehicular ad hoc network.

As a non-limiting example of improving situational awareness using cooperative targeting, FIG. 14 depicts a first S-MMS 18D and a second S-MMS 18E approaching a blind intersection of two pathways. The onboard sensors 1402 of the first S-MMS 18D do not detect the second S-MMS 18E, nor do the onboard sensors of the second S-MMS detect the first S-MMS. However, both S-MMSs 18D, 18E are equipped with an 802.11p architecture (including software and hardware as described above, including an 802.11P transceiver, to effect the 802.11p architecture), transmit their kinematic states, and receive signals from the other S-MMS containing information on the kinematic states of the other S-MMS via a vehicular ad hoc network 1404. In this example, the 802.11P transceiver on the first S-MMS 18D picks up the signals from the second S-MMS 18E. The CNI 371 of the first S-MMS 18D receives the signals from the second S-MMS 18E via the 802.11P transceiver of the first S-MMS and transmits the contents of the received signals (including the kinematic state information therein) to the S-MMS controller 110B of the first S-MMS via the arbitration IAM 370. Additionally or alternatively, the signal contents may be stored in one or more onboard memory locations 120 of the first S-MMS 18D for consumption by the S-MMS controller 110B of the first S-MMS. The signal contents from the second S-MMS 18E may include the identification information, kinematic state information (e.g. current location, heading, and velocity of the S-MMS 18E), and estimated error in the kinematic state information.

The SAC 302B on the S-MMS controller 110B of the first S-MMS 18D may use the information from the signals received from the second S-MMS 18E in one of many ways. In one embodiment, the SAC 302B of the first S-MMS 18D may identify a track for the second S-MMS 18E based on the information from the signals and directly place the newly identified track for the second S-MMS on the situational awareness map via the tactical manager 527. The threat assessor 528 of the first S-MMS 18D may then assign a perceived threat level to the second S-MMS 18E based on the newly identified track or based directly on the information from the signals. Other SAC 302B functions of the first S-MMS 18D may then act on the information from the signals of the second S-MMS 18E as if the onboard sensors of the first S-MMS had detected the second S-MMS, when in reality the second S-MMS was not in view. At the same time that these actions are occurring on first S-MMS 18D, the second S-MMS 18E may also be taking these actions. This is referred to as cooperative targeting.

In some embodiments, data provided by the second S-MMS 18E to the first S-MMS 18D over the ad-hoc 1404 network may be combined with sensor reports 1402 received by the first S-MMS 18D in such a way that the confidence of additional tracks on the situational awareness map maintained by the tactical manager 527 may be improved. For example, the confidence of a location of a particular object as determined by the SAC 302B of the first S-MMS 18D may be enhanced by combining information (e.g. using dual mode variance for example) from one or more sensor reports 1402 from the first S-MMS 18D with data about the same object (e.g. track data) provided by one or more sensors onboard the second S-MMS 18E via one or more signals from the second S-MMS that include sensor data from the second S-MMS.

In some embodiments, the S-MMS controllers 110B on each S-MMS 18D, 18E may automatically coordinate the right of way or other behavior when they meet (e.g. at the intersection depicted in FIG. 14). Each S-MMS 18D, 18E may process one or more received signals and determine a message should be sent over the ad-hoc network 1404 indicating the direction the S-MMS is traveling and the anticipated crossing time of the two S-MMSs. In each S-MMS 18D, 18E, the CNI 371 receives a message from its S-MMS controller 110B and transmits the message via its 802.11P transceiver. Based on this message, the S-MMS controller 110B on one of the two S-MMSs may request permission from the S-MMS controller on the other S-MMS for right-of-way. If the request is approved by the S-MMS controller 110B of the other S-MMS, then the SAC 302B of the other S-MMS determines it is to stop and may alert its drive path manager 529 via its threat assessor 528 to block its forward motion at a specific location and/or time. Additionally or alternatively, the two S-MMS 18D, 18E may simply coordinate a slight increase or decrease in velocity or direction that ensures the two S-MMSs 18D, 18E do not collide at the intersection. In other embodiments, a second message will be transmitted by the S-MMSs 18D, 18E (via their respective components described above) when the intersection has been successfully traversed.

Cloud Integration

Figure 15:
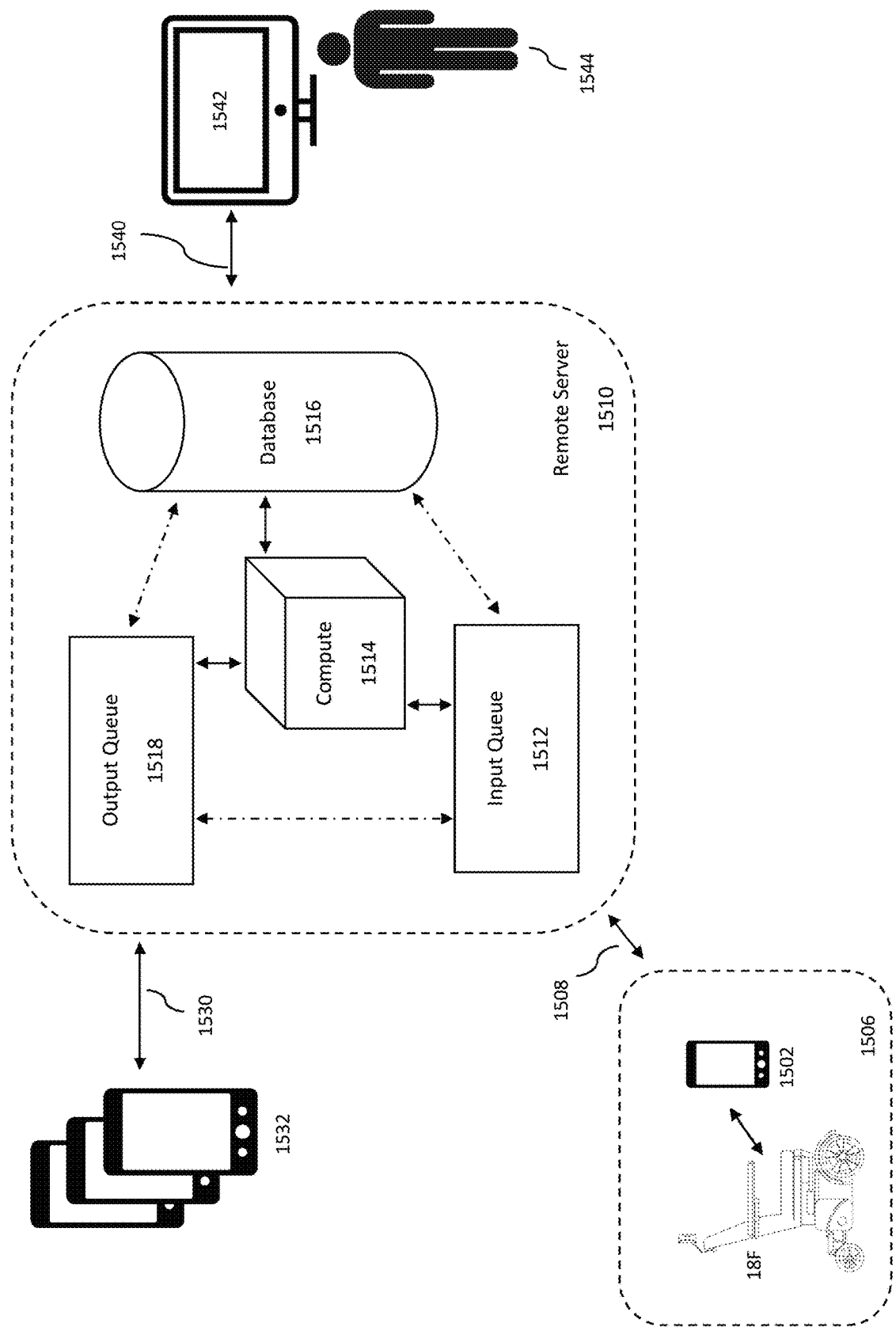
FIG. 15 depicts an embodiment of an S-MMS system securely connected to a remote server.

FIG. 15 depicts an embodiment of an S-MMS system 1506 securely connected to a remote server 1510. In the depicted embodiment, a wireless processor either onboard the S-MMS 18F or associated with the S-MMS as a paired or connected wireless smart device 1502 is operably coupled to a second wireless processor (e.g. via a secure wireless connection), wherein the second wireless processor is configured to operate on a public packet network. The connection 1508 to the public packet network from the S-MMS system 1506 allows access to one or more servers, or remote services, 1510 configured to receive data from a secure memory on the S-MMS 18F and/or the secure memory on the associated smart device 1502 of the S-MMS system 1506. The received data may then be stored in a secure memory on the remote server 1510 wherein the secured, stored data is accessible to pre-authorized systems or pre-authorized persons.

In an embodiment, a pre-authorized system may be a web interface 1542 accessed through an internet connected device, wherein a pre-authorized user 1544 logs in using security credentials and may view a history of events or other data associated with a particular S-MMS user or the S-MMS of that user. In another embodiment, the web interface 1542 may be used to communicate with the S-MMS user or modify or add data to the S-MMS users' unique data file. Data transmitted to the web interface 1540 may be delivered via a secure connection, such as a secure sockets layer (SSL) connection.

In one embodiment, the remote server 1510 may be configured to accept, process, store, and complete specific actions based on messages from an S-MMS system 1506. FIG. 15 depicts a remote server 1510 configured to receive incoming messages from an S-MMS system 1506 via a secure connection 1508. Messages may be sent from the S-MMS system 1506 when a particular event takes place (e.g. on a tipping event), at state events (e.g. at startup of the device), and/or at pre-scheduled times (e.g. at midnight each night). These incoming messages are received by an input queue 1512 hosted on the remote server 1510. Messages from the input queue may then be sent to one or more of a compute engine 1514, a database or data storage system 1516, and an output queue 1518. The compute engine 1514 may compare data included in incoming messages from the input queue 1512 to predefined rules. Additionally or alternatively, the compute engine 1514 may work as a filter to associate individual messages with unique user accounts prior to storing data in a database 1516. The compute engine 1514 may also, based on the content of a received message, push alerts or action requests to an output queue 1518. The output queue 1518 may be a subscription/publication service that, when activated, sends alerts to internet connected devices 1532, such as an S-MMS users' caregiver's smart device. Alerts may be sent as text messages, voice messages, voice calls, or video over a cellular and/or Internet Protocol (IP) network 1530, including the internet. Additionally or alternatively, outbound messages may be sent via the cellular and/or Internet Protocol (IP) network 1530. In some embodiments, the services 1512-1518 on the remote server 1510 may be executed on one or many individual server instances that work together to complete tasks as a single unit on one or more hardware processors. Additionally or alternatively, multiple other remote server architectures are possible to accomplish the intended functionality. As a non-limiting example dashed-dot lines have been included to show alternative connections that may be enabled in some embodiments. Additionally, the compute engine 1514 may include more advanced machine learning logic, such as a neural network, in some embodiments. Diagnostics and other basic server components have been left off of the diagram for the purpose of clarity.

Each of the exemplary embodiments disclosed illustrate how the combined features of the S-MMS system enable various capabilities for S-MMSs. While each exemplary embodiment is discussed separately it should be clear that any one or more aspect of each exemplary embodiment may be combined with any one or more aspects of one or more of the other exemplary embodiments.

Precision Navigation

Figure 16B:
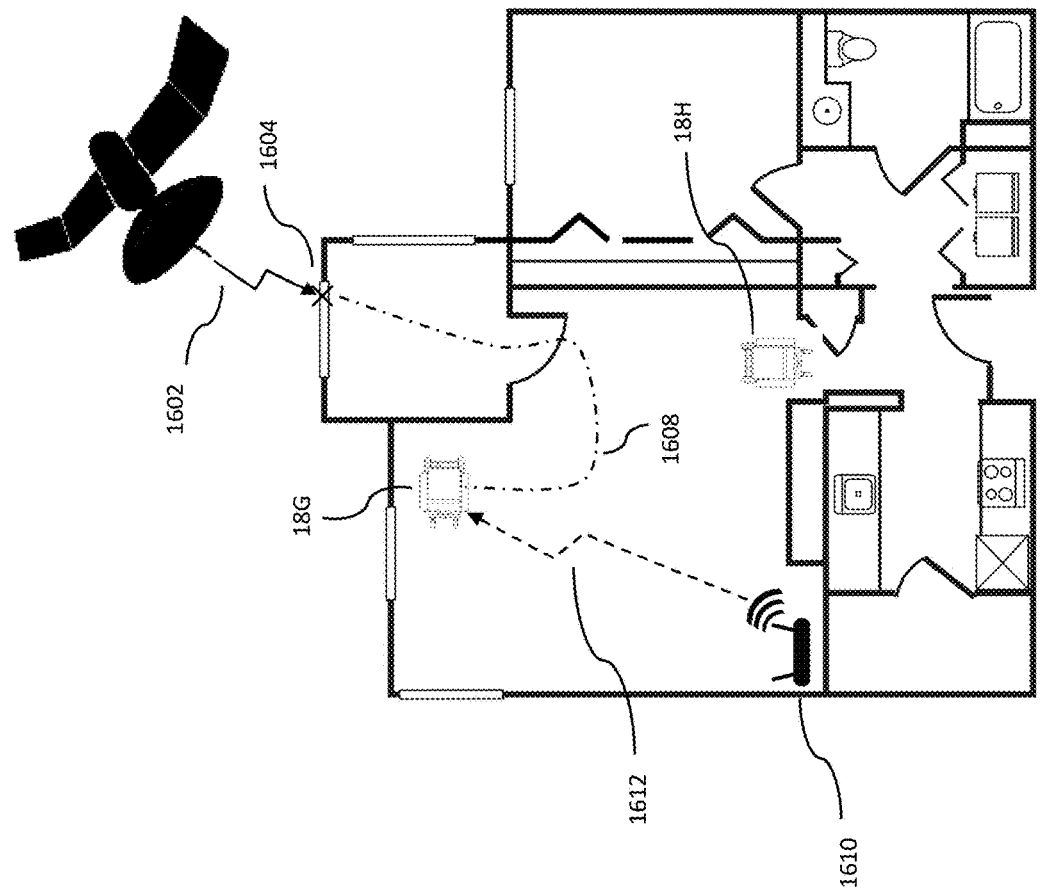
FIG. 16B depicts an embodiment of an S-MMS navigating an indoor environment based on one or more sensors without GPS information.
Figure 16A:
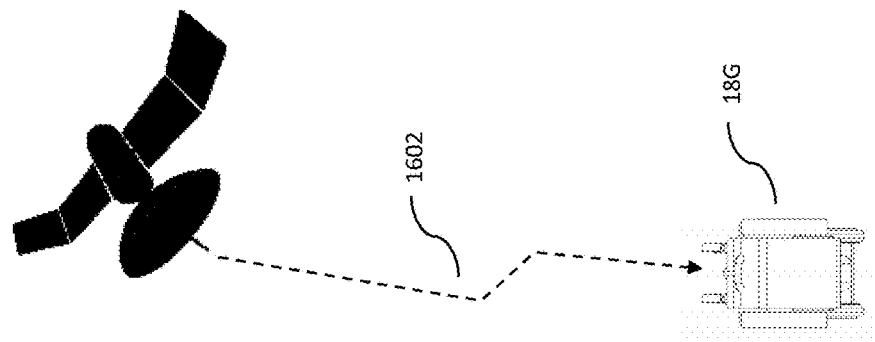
FIG. 16A depicts an embodiment of an S-MMS communicating with GPS satellites.

S-MMS navigation requires accuracy and a unique set of technologies. Navigation for automobile use relies primarily on GPS for location. FIG. 16A depicts an S-MMS 18G configured with one or more communication processors 216 which provide data to the S-MMS controller 110B based on data received from Global Positioning System (GPS) signals 1602. However, unlike automobiles, S-MMS users may spend much of their time indoors and in other locations where GPS does not work. GPS-assisted devices require signal strength for accuracy. When signals weaken (in areas like downtowns or the interiors of buildings), the accuracy lags, potentially causing inaccuracies in navigation that can have a detrimental impact on those who rely on driver assistance or autonomous operation with high accuracy. FIG. 16B depicts an S-MMS 18G in an indoor environment where GPS signals 1602 are weakened or completely blocked.

Moreover, currently available GPS technologies struggle to provide the positional accuracy required for S-MMS navigation along sidewalks, paths, and other rights of way which are typically much narrower than roadways. Indoor navigation of multi-story buildings is another challenge that is not currently addressed by vehicle navigation systems for obvious reasons. These issues mean that S-MMS 18 navigation requires a unique set of technologies and methods. The S-MMS 18 situational awareness controller 302B with tactical manager 527 (FIG. 5), and drive path manager 529 lay the foundation for precision navigation. The tactical manager 527 maintains a situational awareness map of the surroundings (e.g. a map and/or an identification of the ground, conditions, surfaces, and/or objects surrounding the S-MMS) based on data provided to the SAC 302B. The drive path manager 529 references the situational awareness map when assisting a user or for autonomous navigation. The combination of sensors available to the S-MMS controller 110B via the arbitration IAM 370 includes GPS and inertial manager 376, multiple onboard sensors previously disclosed 372-374, information available from remote services 1510 and third-party information available via the CNI 371 which, together, may support creation of a precise S-MMS situational awareness map at a level of detail not otherwise available.

Navigation 363, in an embodiment, may rely at least partially on an inertial reference system (IRS), including an inertial navigation system (INS) for navigating using dead reckoning (DR). Dead reckoning is the process of calculating the S-MMS 18G (FIG. 16) current position by using a previously determined position, or fix, and advancing that position based upon known or estimated speeds and/or steering over elapsed time and heading. In one embodiment, depicted in FIG. 16B, an S-MMS 18G enters a building and loses a GPS signal 1602. The DR function in navigation 363 uses location data from the GPS and inertial manager 376 to update the INS DR fix 1604 by setting a stable earth frame of reference. Speed, heading, and elapsed time data is then provided by GPS and inertial manager 376. Navigation 363 uses this information to track the movements 1608 of the S-MMS 18G (or more precisely it's vehicle frame of reference) relative to the fix 1604 and estimate its location. This allows the S-MMS 18G to navigate inside a building with GPS or otherwise (e.g. otherwise outside of GPS coverage) to a similar degree of accuracy as navigating outside of buildings with continuous GPS data or otherwise. The approach may also be utilized when GPS coverage is available to increase locational accuracy by cross-checking the DR value with GPS data.

Navigation assistance and autonomy may be strengthened further and smoothed by combining DR, as previously disclosed, with the SAC 302B situational awareness map maintained by the tactical manager 527 (FIG. 5). This map is maintained with information from the collision manager 526 and stability manager 525 and their associated sensors. While GPS and DR provide an estimate of absolute location, the situational awareness map provides information on safe directions of travel and distances to surrounding objects. For example, when traveling down a hallway, navigation 363 may know the current location and target end location of the S-MMS 18G, and the SAC 302B is aware that the S-MMS must stay between the two walls to get to that location. The drive path manager 529 of the SAC 302B references the situational awareness map when assisting user or autonomous navigation. This added awareness allows navigation of tight spaces that would not otherwise be possible with DR alone. Increased accuracy of the situational awareness map improves navigation capabilities and, therefore, use of dual mode variance improves S-MMS 18G precision navigation capabilities.

With reference to FIG. 16, in an embodiment, the CNI function 371 (FIG. 5) is provisioned such that at least one wireless system is available to transmit and receive (transceive) data relevant to navigation of an S-MMS 18G. In some embodiments, the S-MMS 18G may be compatible with cellular, Bluetooth, Bluetooth Low Power, Wi-Fi, and other signals which can be used for navigation assistance. These signals may be used in addition to, or as an alternative to, GPS signals. Additionally or alternatively, the S-MMS 18G may use Bluetooth, Bluetooth Low Power, Wi-Fi, and other signals, such as light frequency navigation as sensed by a paired smart device, for instance, being deployed for indoor tracking and navigation by several companies. In one embodiment, a wireless beacon 1610, communicates 1612 with the S-MMS 18G via a communication processor 216 (FIG. 2) of the S-MMS 18G through one of 802.11, Bluetooth, Bluetooth Low Energy (BLE), Near Field Communication (NFC), and/or Zigbee™ among others. These communications 1612 are typically predicated on a "just works" model, one that requires little interface with the device 1610, 18G and the underlying technology. As beacon and indoor navigation systems grow in use, S-MMS 18G precision navigation may take advantage of them to more accurately determine the location of the S-MMS 18G with respect to the earth reference frame. Additionally or alternatively, the S-MMS 18G SAC 302B may use this information to improve mapping of objects and conditions on the situational awareness map as maintained by the tactical manager 527.

As previously disclosed (FIG. 14), two S-MMSs 18G, 18H may communicate with each other via an ad hoc network. In an embodiment, the S-MMSs 18G, 18H may be equipped with an 802.11P transceiver in communication with their respective communications processors 216, and their CNIs 371 are configured to manage 802.11P communications. In this way, the two S-MMSs 18G, 18H form a communication system comprising an ad hoc network for exchanging messages. The contents of messages transmitted from the two S-MMSs 18G, 18H may include information relevant to navigation. In one implementation, the messages may contain information on the current location and kinematic state of the respective S-MMS 18G, 18H. Additionally or alternatively, the messages transmitted from the two S-MMS 18G, 18H may share location and kinematic state of tracks each S-MMS is tracking. These tracks may then be translated by the receiving S-MMS 18G, 18H from a vehicle frame of reference to an earth frame of reference and added to or combined with existing tracks on the SAC 302B situational awareness map maintained by the tactical manager 527. In this way, two S-MMSs 18G, 18H can benefit from enhanced situational awareness though cooperative targeting of objects, conditions, and events proximate to each.

In some embodiments, the S-MMS 18G may be equipped with one or more sensors intended to determine the altitude (earth reference frame) or one or more earth centered direction cosines (geoid reference frame). These sensors may include an onboard barometer or altimeter. In one embodiment, an onboard altimeter reports earth-referenced altitude to the SAC 302B via GPS and inertial manager 376 and/or navigation 363. This information may allow the S-MMS 18G to determine its location in a multistory building for improved navigation and coordinate with the S-MMS 18H by transmitting that information to the s-MMS 18H in one or more messages, thereby working cooperatively in the same multi-story building. Additionally or alternatively, altitude data may be received by an S-MMS 18G or 18H from one or more messages transmitted from a paired smart device 1502 and/or off board beacon 1610, in either case based on sensor readings from one or more sensors on the smart device and/or off board beacon that are included in the one or more transmitted messages.

Best Route

Precision navigation capabilities are strengthened when combined with the availability of high quality maps. Moving through new environments in an MMS can often be very challenging. Often ramps and elevators are out of the way, and if MMS users don't know which direction to go, they may end up getting lost or having to backtrack. For power chair MMS systems, oftentimes the handicap parking space is located across the parking lot from an accessible ramp. New buildings, let alone new cities, may be a daunting challenge in the unknown for an MMS user. Lack of familiarity makes navigation in new areas difficult, and often is very time-consuming. Without pre-existing knowledge of a route and accessibility in an area, an MMS user could easily be overwhelmed and ultimately lost or stranded. When an MMS user is moving through an outdoor environment, something as common as a gap in the sidewalk may be a complete roadblock, as some MMSs may tip if they encounter drop-offs as little as two-inches. Currently available maps do not provide the level of detail or information required for MMS users to plot accessible routes.

The same sensors and advanced navigation and safety systems in the S-MMS 18 that allow it to avoid dangerous drop-offs and collisions may be additionally used to capture valuable data regarding accessibility, terrain, and preferred paths as users navigate through the environment. This data may be used both to create maps of areas that have not yet been mapped with the level of detail required for MMS users and to update areas that have already been mapped. Sensor data on sidewalks, interiors of public spaces, and parking lot hazards may be collected and stored by the S-MMS 18 and associated with one or more maps. The increased accuracy of dual mode variance readings, as previously disclosed (FIG. 12), may aid in producing high quality maps. In some embodiments, the combination of camera data (e.g. via image sensor reports 374) and distance data (e.g. via non-contact sensor and S&T sensor reports 372 or 373) may allow the SAC 302B to create extremely detailed 3D digital re-creations of locations and features based on the S-MMS 18 situational awareness map. The completeness and detail of these maps may vary based on the sensors available on the S-MMS 18, the path of the S-MMS through the location, the amount of processing power assigned to the SAC 302B, and the amount of memory 120 partitioned for use by the tactical manager 527. Additionally or alternatively, a separate mapping function may be added to the S-MMS controller 110B to manage mapping of locations. This may be incorporated as part of the SAC 302B or separate from the SAC.

In some embodiments, data associated with one or more S-MMS 18 sensors and part or all of the situational awareness map maintained by the SAC 302B may be shared with remote services and servers 1510 (FIG. 15). Additionally or alternatively, the data may be shared with a paired smart device 1502 as previously disclosed.

Figure 17:
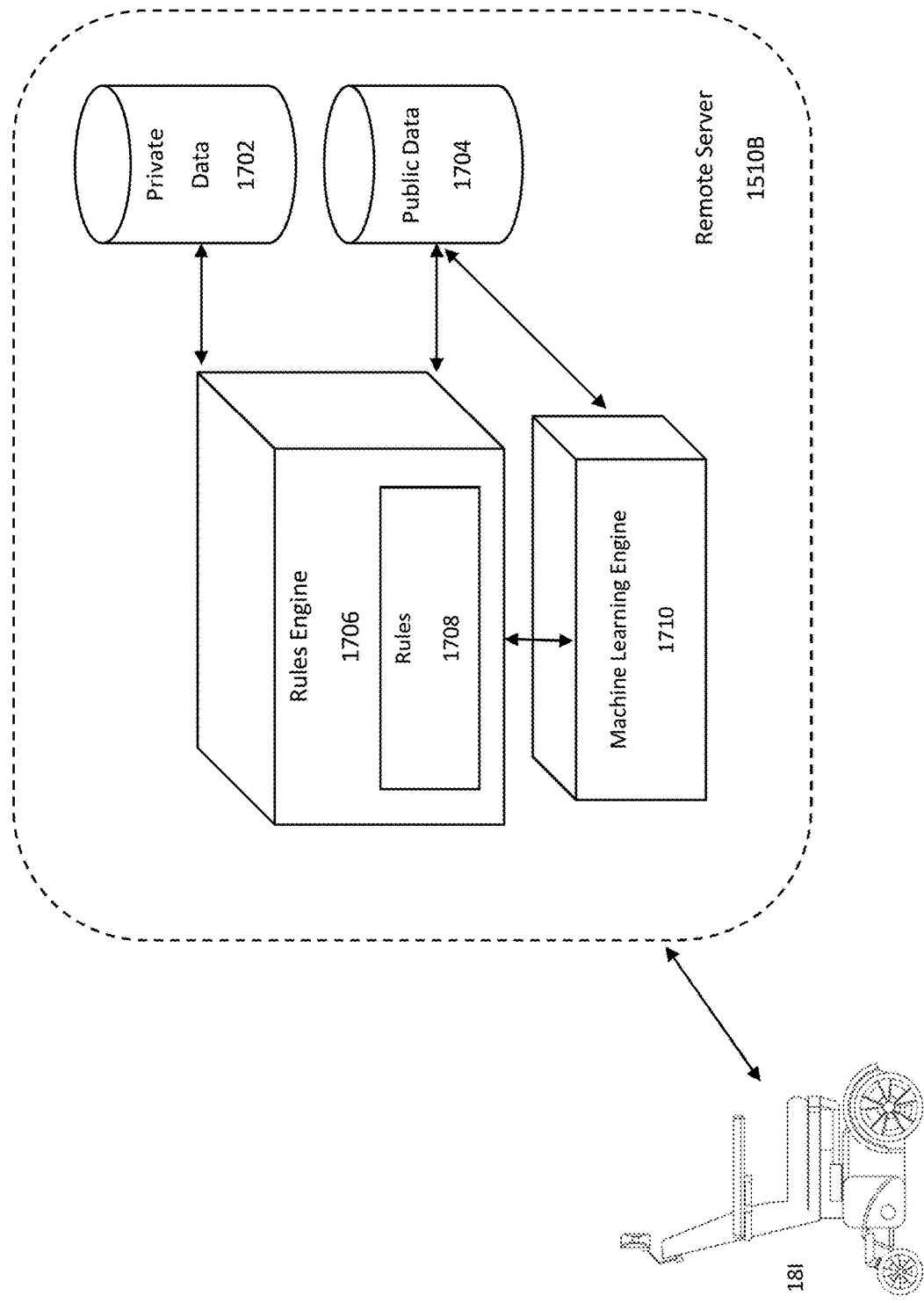
FIG. 17 depicts one or more S-MMSs connected to a remote server.

FIG. 17 depicts an embodiment of an S-MMS 18I wirelessly connected with a remote server 1510B. The remote server 1510B may be configured to accept information related to mapping and navigation from the S-MMS 18I over a public packet network, such as the internet. Additionally or alternatively, the information related to mapping and navigation may be separated by a rules engine 1706 so that any personally identifiable information is stored as private data 1702, and non-identifiable information is added to or merged with public mapping data 1704. In an embodiment, received data may be further anonymized using published best practices for data anonymization by scrubbing data based on predefined rules 1708 or a program that modifies or mixes information (1514, FIG. 15) prior to being placed in public data 1704. In an alternative embodiment, data may be sorted and/or anonymized onboard the S-MMS 18I prior to being transmitted to the remote server 1510B. In some embodiments, public data relevant to navigation can be overlaid on, or included in, existing map programs, such as Google® maps or WAZE™, adding significantly to the resolution of the data available for a given location. In this embodiment, the S-MMS 18I may connect directly to a service over a public packet network, or public data 1704 from a remote server 1510B may be fed to a service or location for use by a 3$^{rd}$ party.

Figure 18:
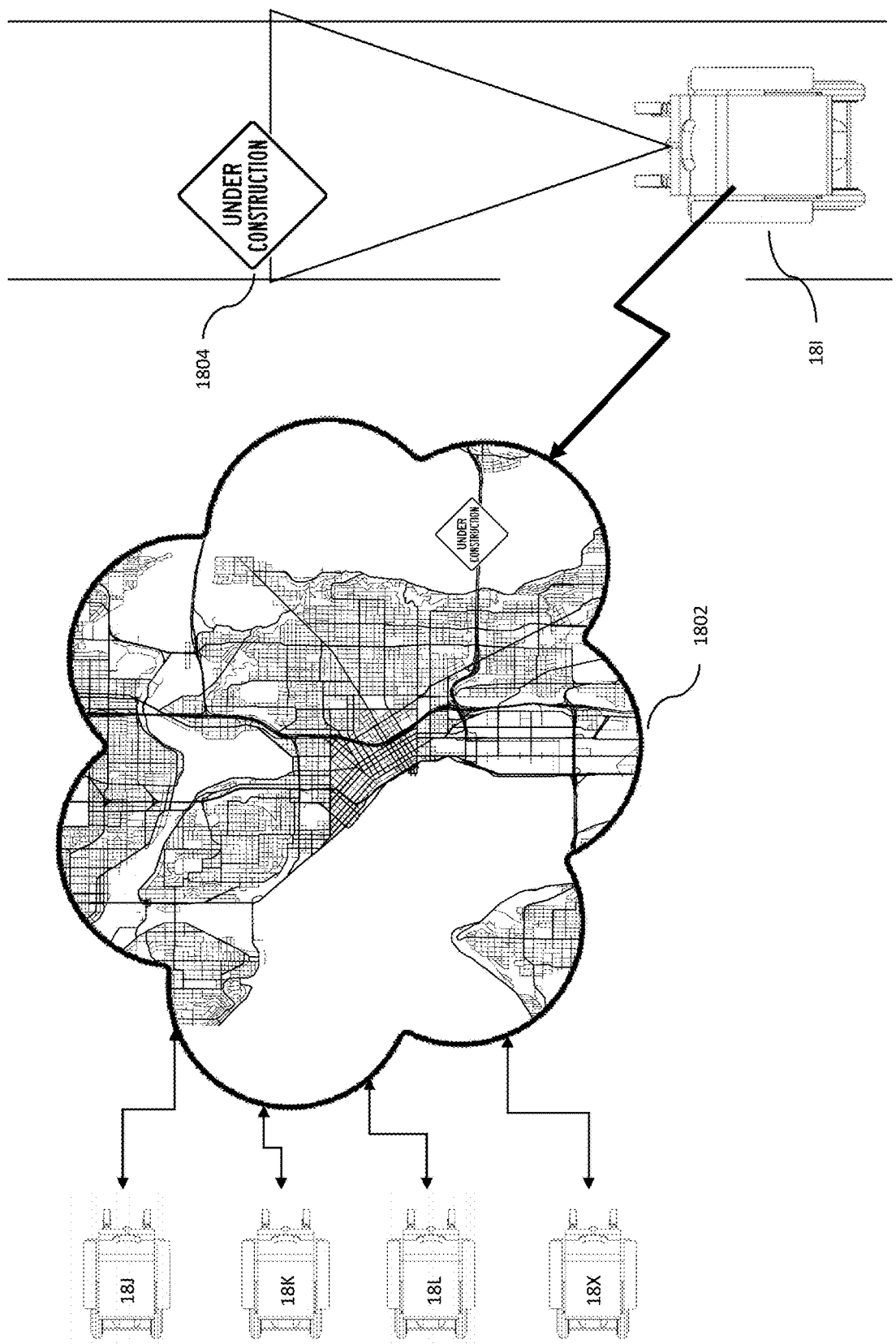
FIG. 18 depicts multiple S-MMS users combining map data.

As illustrated in FIG. 18, as more S-MMSs 18I-X navigate an area and upload their data, map(s) 1802 become more accurate and stay up to date. In some embodiments, users, S-MMSs 18I, 18X, and others may insert pins 1804, much like on the current WAZE™ application, to alert others of new construction and other potential hazards that may affect accessibility of MMS users in an area (i.e. broken power-assist doors or elevators, cracks in the sidewalk, closed ramps, closed trails etc.). In some embodiments, the S-MMSs 18I, 18X may add such pins 1804 to a map automatically by detecting areas that S-MMS users must consistently avoid, areas that S-MMS users must consistently travel through, and/or by using feature recognition. In one embodiment, a machine learning engine 1710 on the remote server 1510B by be configured to recognize and mark these features based on public data 1704 compiled from many users. Rules 1708, such as a confidence level, may be established and enforced by a rules engine 1706 before public data 1704 is modified to include these new features. Whether an S-MMS 18I automatically uploads map data and/or adds pins to map data (including uploaded data) or requires user input may be dependent on user preferences and/or settings. In some embodiments, an S-MMS 18I may automatically and upload (optionally anonymously) map data to a remote server or service with or without added pins or alternately only upload pinned locations to the remote server or service.

Smart MMSs 18I may allow a user to find the most accessible route to their destination based on a combination of the onboard situational awareness map maintained by the situational awareness controller (302B, FIG. 5), paired sensors or beacons 1610 (FIG. 16B), and cloud based map data 1802 (FIG. 18) as previously disclosed. In some embodiments, map data 1802 from one or more sources may be loaded in the S-MMS 18 system memory 120 and/or into the memory of a paired device 1502 such that a user may navigate an area using local map data even when they have no internet connection. In some embodiments, the S-MMS 18I may utilize map information 1802 as an input to the drive path manager 529 (FIG. 5) of the SAC 302B to automatically direct an S-MMS 18 user to a location using the most accessible route. In some embodiments, the best route may be determined by the SAC 302B (by the drive path manager 529 or otherwise) using one or more of time, accessibility confidence, elevation change, and safety as weighting factors. In some embodiments, users may adjust preferences and/or settings affecting how a best route may be determined. In some embodiments, an S-MMS may be capable of learning from trial and error and/or user input/data to shift weighting factors to provide better best route suggestions. The machine learning or rules engine required for this task may reside on the S-MMS controller 110B or may be hosted on a remote server 1510.

S-MMS Mapping

Whether an S-MMS 18 is connected to the cloud or not, it is capable of gathering data relevant to mapping and navigation. Many of the disclosed sensors used to avoid collisions and manage the stability of the S-MMS 18 (e.g. via reports 372-376, FIG. 3) create detailed profiles of the surroundings and ground around an S-MMS 18. In some embodiments, other sensors may be incorporated to specifically improve mapping data acquisition. If the remote server 1510 is offline, mapping data may be saved to secure local memory 120 until such time as the S-MMS 18 reestablishes a network connection 1508 with the remote server. When mapping areas offline, the data gathered by the S-MMS 18 may be mapped with respect to the nearest or most recently known location to improve accuracy when the information is uploaded. While the mapping system is described as essentially cloud-based in some embodiments, it should be clear that the same principles may be applied to mapping applications that may never, or rarely, share information via the Internet.

Figure 19:
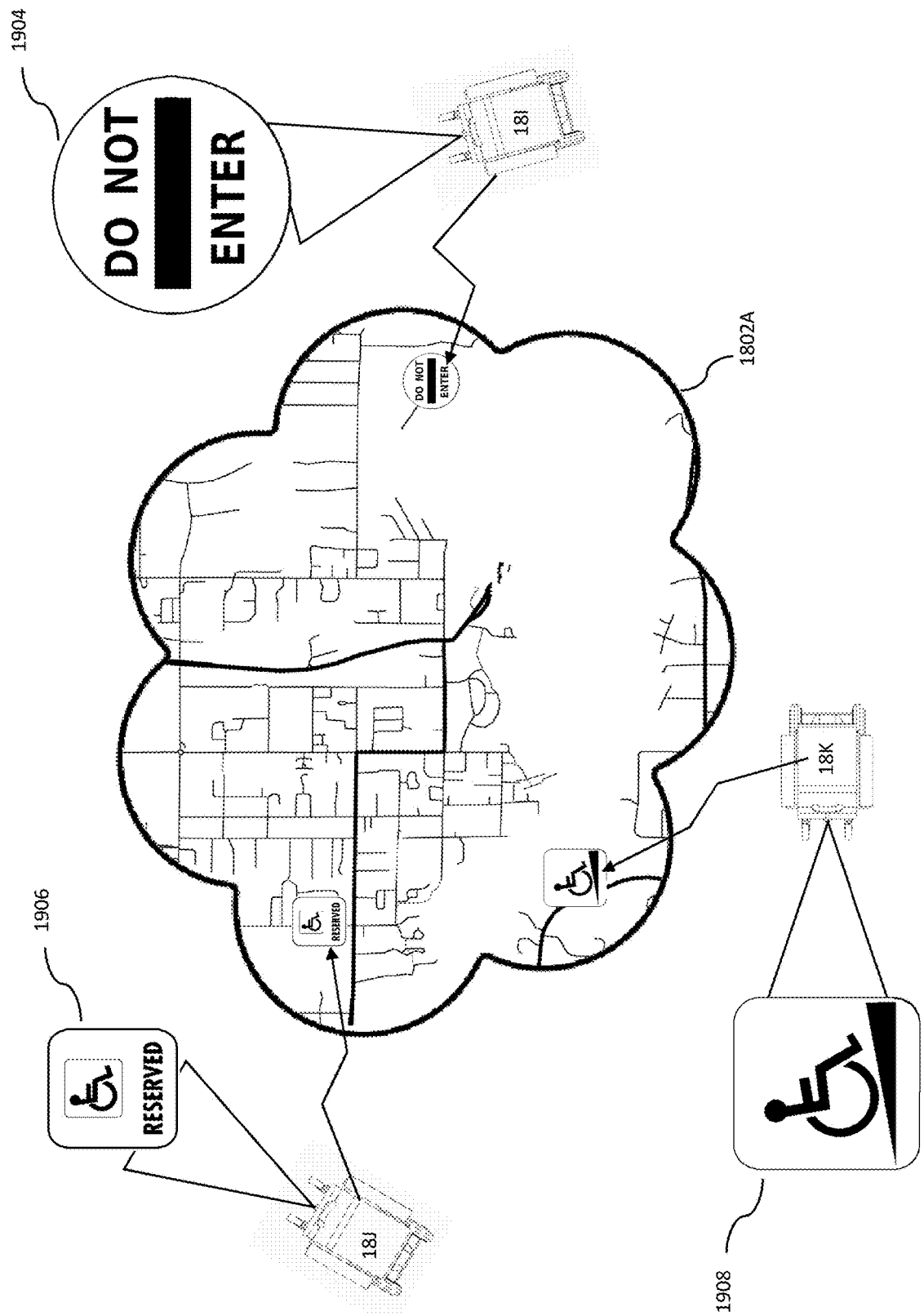
FIG. 19 depicts multiple users uploading accessibility information to a shared map repository.

S-MMSs 18 equipped to continuously measure and evaluate their surroundings can create highly accurate maps of the accessibility of each location they traverse, as illustrated in FIG. 19. As multiple S-MMSs 18I-K upload information, often mapped with respect to different known locations, a remote mapping system (e.g. hosted on a remote server 1510) is able to receive the multiple streams of data (e.g. 1512), overlay and fuse the information to eliminate outliers (e.g. via a computation engine 1514 and/or rules engine 1706), and create a unified publicly available map 1902, stored in a public data repository 1704, for use by S-MMS systems 1506, general caregivers 1544, or smart devices 1532. The map 1802B then provides accurate up-to-date navigation information to users using the S-MMS 18 accurate frame of reference tracking previously disclosed.

As a non-limiting example, mobile chair S-MMS 18 users navigate the world in a way that requires a wholly unique set of accommodations which can vary greatly between locations. In addition, each accommodation is likely used in sequence (e.g. from an accessible parking spot, to a sidewalk ramp, to a different ramp, to a power-assisted door). As mobile chair S-MMS users navigate the world, each link in each sequence is a potential roadblock, unknown to them until they or an assistant arrives at the next step. Detailed, continuous mapping and logging of these accommodations is important to relieving this uncertainty. In some embodiments, S-MMSs 18I-K may be configured to automatically detect and catalogue any accessibility features 1904, 1906, and 1908 encountered while they are traveling. Automatic detection of accessibility features may be accomplished using one or more techniques currently used for facial recognition, including geometric, photometric, or 3D recognition. In some embodiments, feature extraction 530 on the SAC 302B may utilize algorithms, including principal component analysis using eigenfaces, linear discriminant analysis, elastic bunch graph matching using the Fisherface algorithm, and the hidden Markov model to identify accessibility features. In an embodiment, sensor track fusion 500 may combine feature extraction 530 outputs with information from one or more non-contact sensor reports 372 and S&T sensor reports 373 for 3D recognition of accessibility features. In an embodiment, one or more machine learning engines (e.g. 1710, FIG. 17) may be used to identify accessibility features using published approaches, such as multilinear subspace learning or dynamic link matching. The totality of these measurements from S-MMSs 18I-K, when combined as previously disclosed, creates a detailed map of not only the accessibility of a specific location, but of the sequence of locations through which a user must pass to their destination, which may be used by other S-MMSs 18I-K navigating the same location. As an analogy, the sequence of these events to enter a building may be equivalent to road information provided for automobile navigation. In some embodiments, other systems and devices, such as wearable devices (wearables) or smart device applications, either associated with an S-MMS 18 or not, may contribute information to mapping 1802B by transmitting their data to one or more S-MMSs or the remote server 1510, and processed and/or stored as described above, and/or may host the mapping application(s).

Indoor locations are a challenge to accurately map because they often change, are often densely populated with objects, and may require repeated scans in order to be mapped and kept up-to-date. S-MMSs 18 equipped to continuously sense and document their surroundings, as previously disclosed, can overcome these issues to create highly accurate and regularly updated maps of indoor locations. Not only can these maps be used to enable accessible S-MMS 18 indoor navigation, they can also be used by services like Apple's MapKit™ to create very accurate indoor navigation and wayfinding for everyone.

Figure 20:
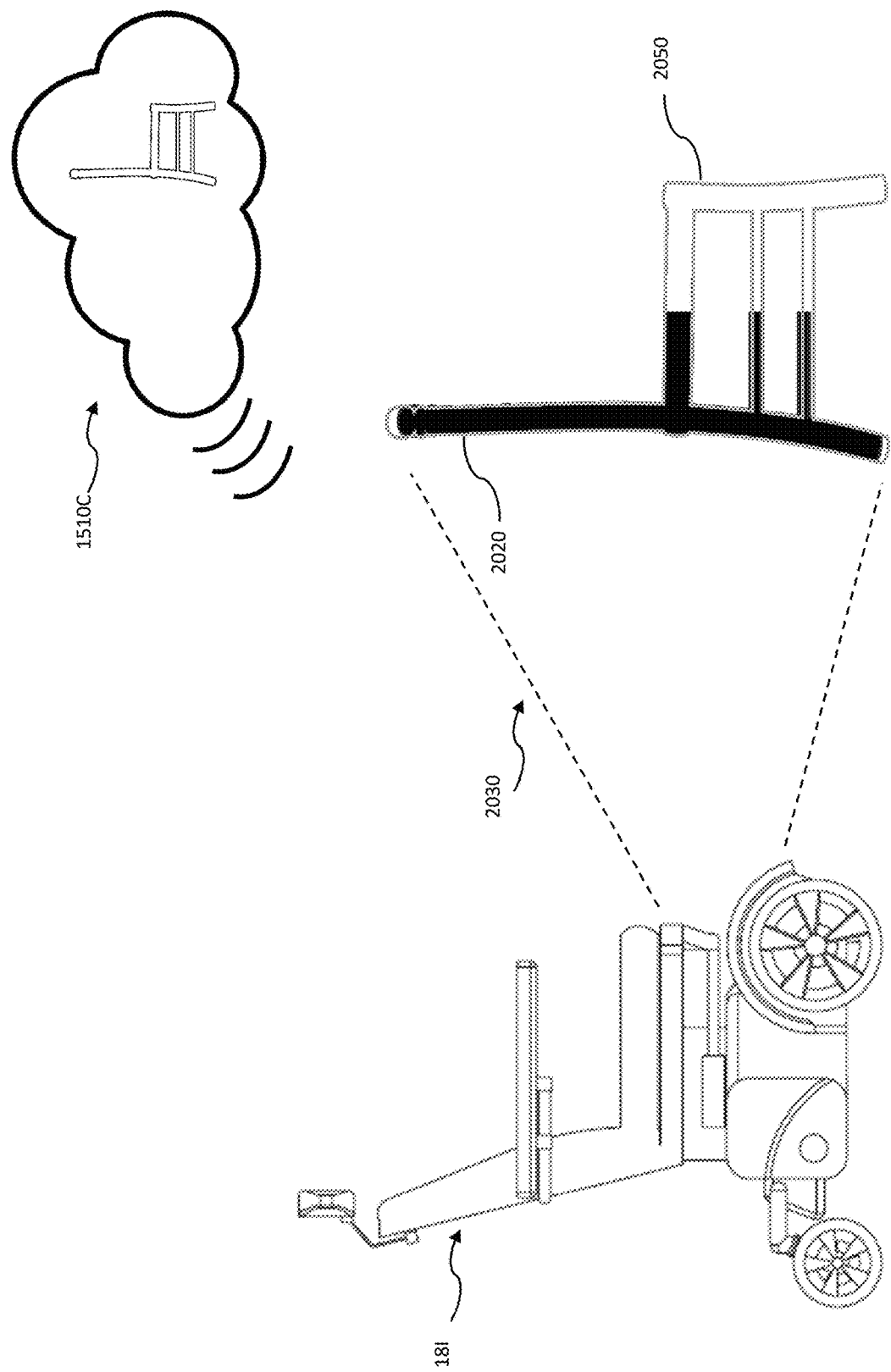
FIG. 20 depicts an embodiment wherein an S-MMS uses onboard sensors to sense and model an object.

In some embodiments, this mapping process may also be linked to 3D models of common objects such as chairs, tables, and doors that can be placed and associated on a map by either an S-MMS 18 user, a third party, or in an automated fashion to further refine indoor maps. Objects may be automatically created based on S-MMS 18 sensor data, custom modeled using a tool such as SketchUp™, or they may be retrieved from model databases such as Grab-CAD™ FIG. 20 depicts an embodiment wherein the S-MMS controller 110B of S-MMS 18I uses one or more sensor reports (e.g. sensor reports 373 from a LIDAR and sensor reports 374 from a camera) to sense an object 2050. The object 2050 is assigned a track by the SAC 302B, and may be characterized as a chair by sensor track fusion 500 or by a machine learning engine 1710 (either onboard the S-MMS 18I or on a remote server 1510B) configured for object detection. Based on the characterization, the S-MMS 18I then downloads a 3D chair model from a remote service or server 1510C. The tactical manager may then associate this new data with the chair track, scale 2030 the 3D chair model to match the proportions of the measured object 2020 so that it takes up the same space as the physical object, and then place the object on the situational awareness map of the SAC 302B. This process may result in the 3D chair model, scaled and placed on the situational awareness map, effectively filling in gaps 2050 in the S-MMSs 18I awareness. In some embodiments, these objects may then be treated by an S-MMS 18I as if they were physically present in the world and properly handled by the situational awareness control 302B of an S-MMS 18I. This data may be stored in local memory 120 and shared with the previously disclosed remote server or service used for public mapping 1510.

Socialization can be a challenge for MMS users, regardless of abilities or impairments. The act of mapping locations could be gamified to achieve both the complete mapping of locations more quickly and to encourage social interaction for S-MMS 18I users. Most locations have high- and low-trafficked areas, and, motivated by gameplay, the completeness of mapping could be encouraged and rewarded. In one embodiment, a remote server 1510B configured to generate public map data 1704 may enact rules 1708 in a rules engine 1706 which flag areas of low map 1802 quality. These areas may then be displayed to S-MMS 18 users via a paired smart device 1502, to users or caregivers via a web interface 1542, and to others via smart devices 1532 in order to encourage mapping of those areas. In an embodiment, players may earn points/experience/status/achievements/rewards based on where they map, how much total area they map, if they are the first to map an area, if they identify a new obstacle or accessibility feature, etc. Additionally or alternatively, the areas flagged by the remote server 1510B may be communicated to S-MMSs 18I proximate to the area of the flag. This information may be received via one or more wireless transceiver 216 onboard the S-MMS 18I, and communicated to the S-MMS controller 110B via CNI 371. In some embodiments, this may cause the S-MMS 18I to alert the user via the HMI 352 or a paired smart device 1502 that a mapping opportunity is nearby. Additionally or alternatively, the sensor tasker 520 function of the SAC 302B may cause the S-MMS 18I to take additional sensor readings when passing through a flagged area and communicate that data back to the remote server 1510.

A remote server 1502 may be configured to transmit messages/data and receive messages/data to cause the games to be played on a receiving smart device 1502, including for a user interface to be displayed on the smart device to display data for the game and allow inputs to the smart device for the game (such as the inputs described above) that are transmitted to the remote server for processing and response so the game can be played. Alternately, the games may be hosted in the hosted 125 or complex application space 130 of the S-MMS 18 (FIG. 1), and the S-MMS controller 110B then would be configured to transmit messages/data and receive messages/data to cause the games to be played on a receiving smart device 1502, including for a user interface to be displayed on the smart device to display data for the game and allow inputs to the smart device for the game (such as the inputs described above) that are transmitted to the remote server for processing and response so the game can be played.

Augmented reality (AR) may enhance gameplay to offer 3D games, such as Pacman, chasing aliens, or playing hide-and-seek with animals, in locations that need to be mapped. This ability may encourage movement into certain flagged areas for mapping, or may just enhance the enjoyment of the activity itself. FIG. 21 depicts an S-MMS 18M paired to an AR device 2102 via a wireless link 2104. In one embodiment, the CNI function 371 (FIG. 3) is provisioned such that at least one wireless system is available to transmit and receive (transceive) data relevant to a desired operation of a mobile chair S-MMS 18M. In one embodiment, an AR device 2102, such as a smart device running an AR application or a wearable such as MicroSoft HoloLens, communicates 2104 with the S-MMS 18M via a communication processor 216 (FIG. 2) of the S-MMS 18M through one of 802.11, Bluetooth, Bluetooth Low Energy (BLE), Near Field Communication (NFC), and/or Zigbee™, among others. These communications 2104 are typically predicated on a "just works" model, one that requires little interface with the device 2102 and S-MMS 18M and the underlying technology. The levels of security and privacy are device 2102, OS, and wireless service dependent. In some embodiments, the AR device 2102 may communicate 2104 with the S-MMS 18M via a wired interface. In some embodiments, the communications 2104 may be wireless and accomplished via a secure Bluetooth connection based on the HDP and MCAP standards included in the Bluetooth Core Specification herein incorporated by reference.

Other activities may also, or alternatively, be gamified. For instance, completing regular exercises/physical therapy sessions or improvements in such activities could be rewarded in a game or game-like fashion. These game applications may be hosted in the hosted 125 or complex application space 130 of the S-MMS 18 (FIG. 1) and communicate with the S-MMS controller 110B via an API 135. Activities that may normally be tedious or monotonous may be gamified to encourage the users to perform and to motivate them to excel with various points/experience/status/achievements/rewards. In some embodiments, the rewards may be one or more of based on the particular gaming environment (for the activity or chosen by the user), picked by the user from an assortment of different rewards, and personalized to motivate a particular user. Feedback, prompts, and input for the games may be provided via the HMI 352 or via a paired smart device 1502.

S-MMS user data may be characterized as HIPAA medical data or may be characterized as non-medical data. By default, all user data associated with a user account may be characterized as private and secure, including gaming and mapping data. However, this data may be shared in multiple ways. In some embodiments, a user may elect to share collected map data with a third party such as a mapping service or S-MMS manufacturer. This data may be disassociated from the user when shared. In some embodiments, the user may choose to share only certain mapping data on a transactional basis with third parties. For conditional or transactional data sharing, technologies such as block chain may allow for secure sharing and/or payment for data services provided. In some embodiments, the user and/or caregiver may set privacy settings and preferences globally in the system and/or per use, per application or application type. In these embodiments, the S-MMS controller 110B and/or smart device 1502, as the case may be, would implement the above-referenced technology in the messages/signals/communications/data it sends.

Location Memory and Auto Return

MMS users often frequent the same locations inside and outside the home. The effort and time of navigation to these frequent locations increases greatly for mobile chair MMS users and can increase more for those with cognitive or mobility impairments that impact the motor functions needed for steering. Simple navigation to frequent locations in one's own home can become both time-consuming and taxing for some MMS users, which directly impacts quality of life.

The best route system, previously discussed, can assist users with autonomous navigation to frequent locations within a home, facility, or other frequently visited place. In some embodiments, the S-MMS 18 situational awareness controller 302B has an awareness of predetermined locations or a history of recently visited locations. The S-MMS controller 110B uses the SAC 302B and navigation 363 to assist the user and speed their travel to a selected location. Users may select a destination using the S-MMS HMI 352 and/or the HMI of an associated smart device 1502. HMI selection mechanisms may include a control button or input on the HMI, a voice command, or the selection of a destination from a list of predetermined locations. Additionally or alternatively, the S-MMS navigation 363 or drive path manager 529 of the S-MMS controller 110B may make a rules based determination based on current location, direction, and possible destinations of possible locations to offer the user. Once a selection is made, the S-MMS 18 assists safe navigation to the selected destination, helping speed up the trip and lowering the burden of driving on the user. Autonomous navigation is managed by the drive path manager 529 of the SAC 302B based on information received from navigation 363 and other S-MMS systems previously disclosed. The motor controller 351 responds to commands from the SAC 302B to drive motors and actuators.

The S-MMS 18I may learn from the user's behavioral history and may begin to anticipate the user. In some embodiments, S-MMS 18I navigation history may be sent to a remote server 1510B where one or more of a rules engine 1706 or machine learning engine 1710 may identify and flag frequently visited locations. This information may be stored as private data 1702 on the remote server, or it may be transferred to S-MMS 18I onboard memory 120. In an embodiment, the rules engine 1706 or machine learning engine 1710 may be hosted on the S-MMS controller 110B. In an embodiment, the drive-path-manager may look for flagged locations in the private data 1702 proximate to the current path. Those locations may then be offered to the user for selection via the HMI 352 or a paired smart device 1502. In some embodiments, the rules engine 1706 may look for correlations between locations and other factors, such as time of day. For instance, if a user regularly travels to the kitchen for lunch at 12 PM, the S-MMS controller 110B may guide them there when the user turns in that direction around that time period. In some embodiments, the user may be presented with the suggestion by the S-MMS controller 110B and choose yes or no to activate the automatic guidance or not. Based on the previously disclosed approach, the S-MMS controller 110B may be capable of determining when the user is differing from their usual behavior, such as if the S-MMS controller detects the location as other than home at 12 PM, and the S-MMS controller will not suggest travel to the kitchen at that time.

Motion Memory and Parking Assistant

Motorized mobile systems can be difficult to repeatably navigate due to the imprecision of the steering mechanism (e.g. a joystick or steering bar) and the lack of an ability (for some systems) to move directly sideways. In addition, frequent locations for parking often have a relationship to another object and/or activity, including parking next to a toilet to allow toileting, parking in a van or truck in order to be tethered to anchor points, and parking next to a bed, among others. These frequent parking locations can require precise position and maneuvering to provide the appropriate proximity for access or the exact location for tethering in the vehicle scenario. Precision is required for access for the desired location, but the proximity often requires careful maneuvering. This precision movement and alignment is important and time-consuming.

An S-MMS 18 may aid with parking at common locations by assisting with speed and alignment. Assistance, in some embodiments, may include full autonomous positioning and in other embodiments may simply constrain user inputs to within a predefined error term of an ideal track established by the drive path manager 529 of the SAC 302B. In an embodiment, an S-MMS controller 110B may utilize an SAC 302B (FIG. 5) along with one or more of the previously disclosed precision navigation techniques, location memory and precision map data to navigate to a predefined parking location. This embodiment requires that the S-MMS controller 110B stores the required parking orientation at that location. This data may be stored either onboard S-MMS 18 memory 120 or on a remote server 1510. By combining the previously disclosed techniques, a parking assistant implemented by the S-MMS controller 110B may eliminate the need for the user to precisely maneuver by automating tasks. The S-MMS 18 prevents misalignment through its understanding of the correct positioning at that destination, and speeds parking by recognizing the safe path to, and any obstacles near, the desired parking location. In some cases, the S S-MMS controller 110B may enter an automated parking mode where the S-MMS controller takes over and controls the S-MMS 18 to park more quickly and precisely and reduce strain on the user. The automated parking mode may store information about common parking areas and/or it may be able to perform common actions in known and/or new locations using sensor data.

Figure 22:
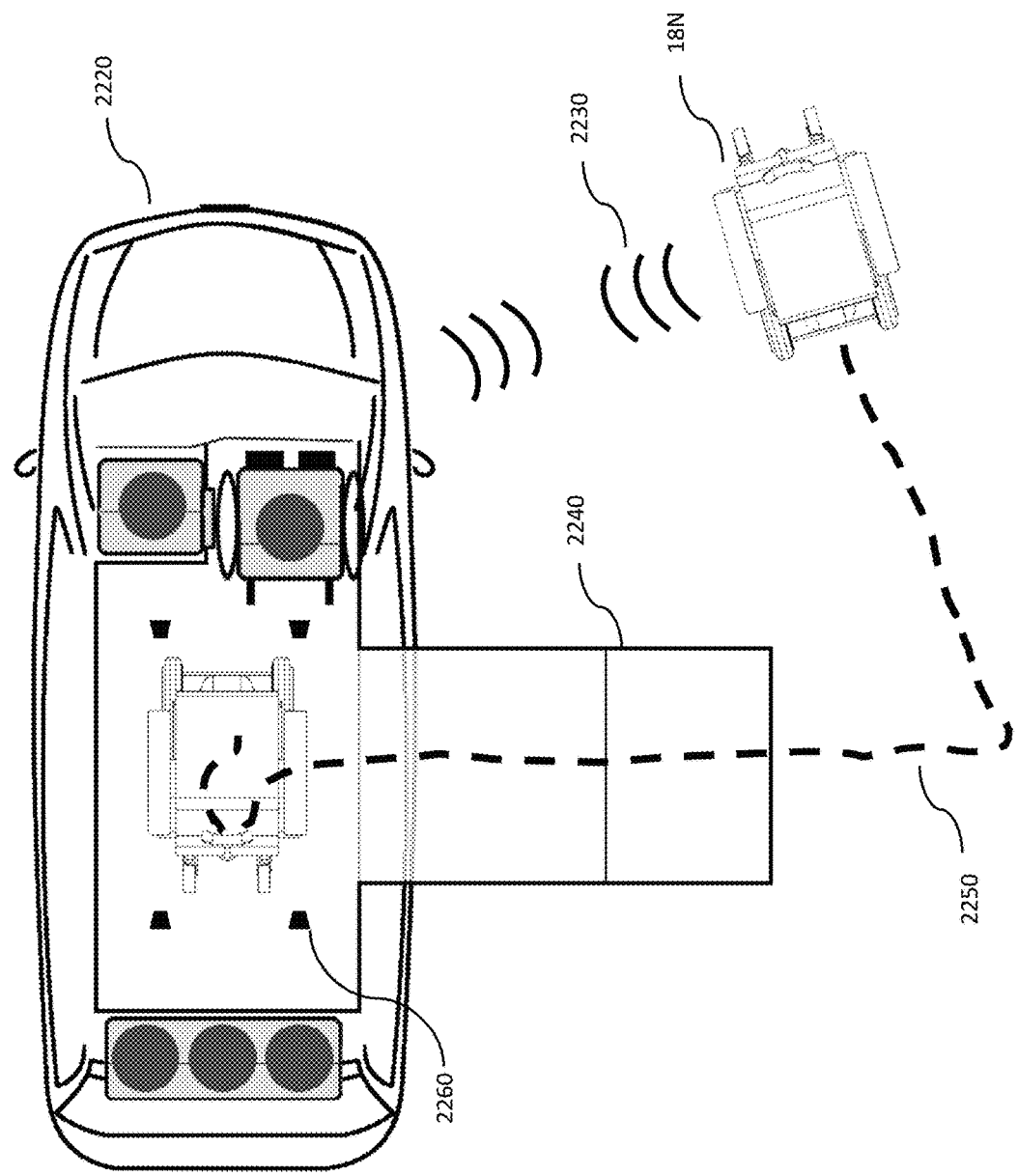
FIG. 22 depicts a typical path and motions required to successfully park a mobile chair MMS inside an accessible van.

FIG. 22 illustrates a typical path and the motions required to successfully park a mobile chair S-MMS 18N inside an accessible van 2220. In an embodiment, a parking assistant implemented by the S-MMS controller 110B may respond to external, wireless signals and may transmit one or more wireless signals via one or more communications processors or transceivers 216. Using the parking assistant, a user may take advantage of many of the capabilities of the disclosed S-MMS 18 in a fluid process. As the user approaches the van 2220 they may be prompted via the HMI 352 or a paired smart device 1502 to confirm that they are heading to the van 2220. The SAC 302B of the S-MMS controller 110B may recognize the van 2220 based on user input, image recognition, location, patterns of use, and/or wireless ad hoc communication (e.g. such as WAVE™ as previously disclosed). If parking mode is confirmed, the S-MMS controller 110B may transmit one or more wireless communications 2230 to a control system of the van 2220 to cause one or more of automatically unlock the van if the user is authorized, open the door, and lower the automatic ramp 2240. Wireless communication may include an ad hoc network or RF signals. As the ramp 2240 touches down, the S-MMS 18N user may confirm that they wish to use the parking assistant and the S-MMS controller 110B may cause the S-MMS 18N to automatically drive up the ramp 2240 and follow the path and motions 2250 depicted to position itself relative to attachment point(s) 2260 in the vehicle. The path and motions may be calculated and executed uniquely each time by the drive path manager 529 of the SAC 302B to position the S-MMS 18N relative to one or more objects or references available at the location. As a non-limiting example, one or more of the image sensors may be tasked by the sensor tasker to monitor for the attachment point(s) 2260 (e.g. tie down straps) using feature extraction 530. These "landmarks" may then be used to develop the drive path 2250 to be used by the –MMS controller 110B. Additionally or alternatively, the SAC 302B may be configured so that once the S-MM 18N is positioned in a location proximate to the target, the S-MMS controller 110B, in coordination with the motor controller 351, executes a predefined series of motions retrieved from memory 120.

Figure 23:
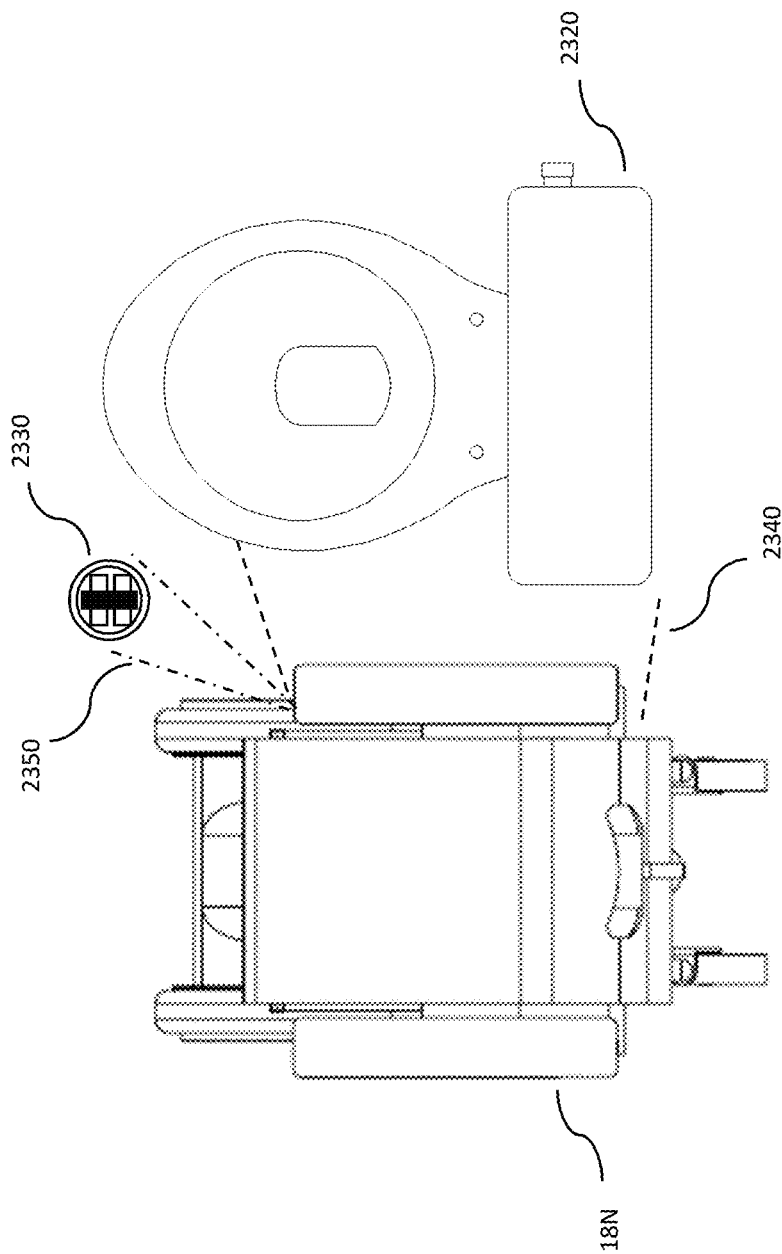
FIG. 23 depicts use of targets to assist in S-MMS positioning.

FIG. 23 illustrates the use of one or more optical or retro-reflective targets 2330 to assist in S-MMS 18N positioning. Placing targets 2330 allows the S-MMS 18N to position itself quickly and with high precision in a wide variety of settings. As an added benefit, targets 2330 may be used as an approximate reference point for positioning for non-MMS users. As a non-limiting example, a vinyl sticker 2330 with a predefined pattern may be placed at particular coordinates relative to a handicap accessible toilet 2320. Data may be associated with the particular pattern or pattern and location combination. The unique pattern may be associated with a location, a function, a message, or set of desired S-MMS 18N actions that may assist in positioning the S-MMS 18N in relation to the target 2330. This information may be stored onboard S-MMS memory 120, may be uniquely associated to an individual user and stored as private data 1702, or may be accessible public data 1704 retrieved by the SAC 302B from a remote server 1510.

The –MMS controller 110B is capable of recognizing the positioning target 2330. In one embodiment, one or more onboard image sensor reports 374, received by the SAC 302B, are processed in feature extraction 530, and the target pattern is recognized by one or more of the pattern recognition processes previously disclosed (FIG. 19). Positioning may still be assisted by use of other onboard sensor reports 372-376 (FIG. 4) as well as data referenced or provided by the target 2330. In an embodiment, SAC 302B sensor fusion 500 associates the target 2330 identified by feature extraction 530 as part of the object track, in this case a toilet 2320. This association of the target and the object data serves as an alternative approach to dual mode variance, wherein a positioning target proximate to the object is used as an extension of the object to provide information on the location or a track to the SAC 302B and increase the accuracy of the situational awareness map maintained by the tactical manager 527.

Targets 2330 may take many forms and include standardized targets that are used in public settings to increase accessibility for S-MMS 18N users. Additionally or alternatively, custom targets 2330 may be used that users may purchase or print and place at locations of their choosing to assist with positioning tasks of their choosing. In some embodiments, the targets 2330 may be recognized objects in the surroundings, such as a particular piece of furniture or decoration in a home rather than a sticker. In some embodiments, targets 2330 may take any form that is recognizable by the S-MMS controller 110B of the S-MMS 18N, including certain objects, artwork, stickers, decals, and patterns such that the targets may blend with the overall aesthetic of the location they are in.

In some embodiments, targets 2330 may incorporate or be replaced by RFID chips, Bluetooth beacons, or other computer readable chips, such that they may be recognized by, and transmit their coordinates to, the S-MMS controller 110B wirelessly as previously disclosed for general, precision indoor navigation.

Transfer Assistance

Transfers to and from an MMS are common and critical for users. As a non-limiting example, therapists spend months with new mobile chair MMS users breaking down transfers, moving into a car, moving to a toilet, and/or switching to a couch or chair. Each piece of that journey becomes part of a routine that, when improperly done, can lead to serious injury. If an MMS user's seat is positioned slightly wrong for a transfer, it changes distances and balance points that they have practiced and rely on. These changes often lead to falls. But even if the user doesn't fall, they may strain or pull muscles in the attempt to correct for an initial positioning error.

Figure 24:
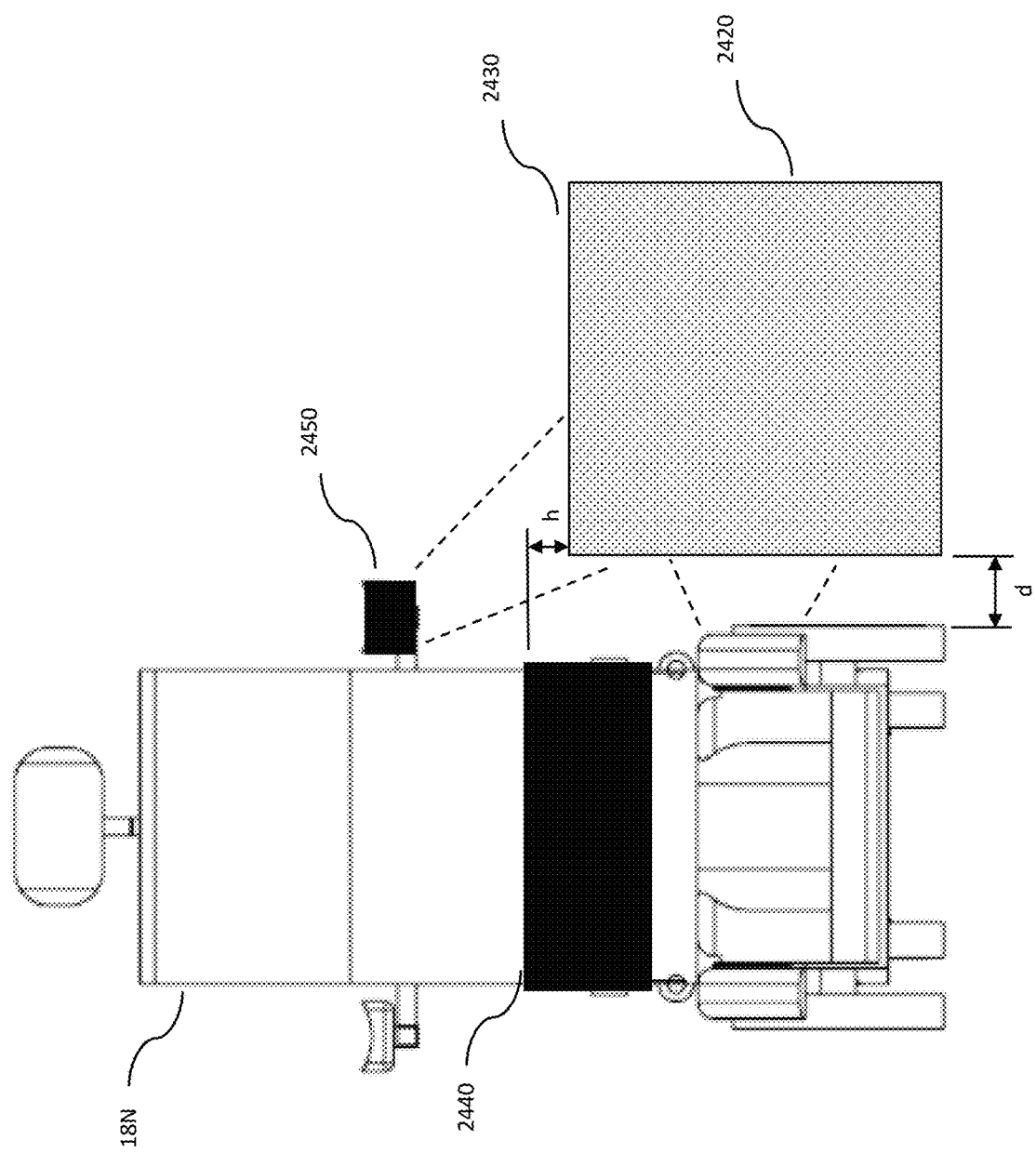
FIG. 24 depicts a common S-MMS transfer situation.

A transfer mode allows S-MMS 18N users to have more control and confidence when transferring to and from their S-MMS. FIG. 24 illustrates a common transfer situation. As a non-limiting example, consider a user positioning their S-MMS 18N next to a chair 2420 that they plan to transfer to. This situation is unique from tables and desks, because rather than pulling forward, toward the interface, users often approach from the side and then transfer sideways to the chair 2420. The user must position the S-MMS 18N seat 2440 both vertically (h) and horizontally (d) in relation to the target chair 2420 with high accuracy. The parking assistant, as previously disclosed, may assist the S-MMS 18N user in accurately achieving the desired horizontal distance (d). Using the transfer mode, the S-MMS controller 110B may automatically adjust the seat position (e.g. by sending control signals to the motor controller 351 after determining the height from sensor reports 371-374) to match the vertical height of the adjacent seating surface 2430 or maintain a predefined vertical height difference (h) per the user's settings for easier transfer. Seat height of the adjacent seating surface may be determined using one or more onboard, non-contact sensors 372.

In an embodiment, as the S-MMS 18N approaches the chair 2420, or other target transfer surface, the user may select transfer mode via the S-MMS HMI 352 or a paired smart device 1502 and indicate the transfer target 2420. With this information, the S-MMS controller 110B SAC 320B may send control signals/commands to the motor controller 351 causing the S-MMS 18N to autonomously pull within a maximum preferred transfer gap (d) of the transfer target 2420. This gap (d) may be unique to each user and stored in memory 120 as part of a unique user profile. In addition, the S-MMS controller 110B may position the S-MMS 18N per settings in relation to the transfer target 2420 front to back. The S-MMS controller 110B may then adjust the seat 2440 height in relation to the height of the adjacent seating surface 2430 for easier transfer. In one example, the S-MMS controller 110B repeatedly receives and processes sensor reports to determine a current distance away from the transfer target 2420 and transmit control signals/commands to the motor controller 351 causing the S-MMS 18N to autonomously pull within the maximum preferred transfer gap (d) of the transfer target 2420. Similarly, the S-MMS controller 110B repeatedly receives and processes sensor reports to determine a current height of the seating surface 2430 of the transfer target 2420 and transmit control signals/commands to the motor controller 351 causing the seat 2440 height to be moved to the correct height relative to the adjacent seating surface 2430. In one embodiment, additional non-contact sensors 2450, such as an infrared or ultrasonic sensor, is mounted in a location such as the armrest of the chair so that the height of a transfer seating surface 2430 may be measured relative to the S-MMS 18N seat 2440. Most S-MMS users prefer to transfer from a higher to a lower seating surface, so the user may preprogram a preferred height differential (h) so that the S-MMS controller 110B of the S-MMS 18N provides a personalized optimal transfer when the mode is activated Similar to the previously disclosed approach mode, the S-MMS controller 110B of the S-MMS 18E may also be programmed and the settings for common transfer locations can be saved in local 120 or remote 1510 memory, in some embodiments.

Additionally or alternatively, the transfer mode may be configured to automatically modify other seat settings and/or deploy transfer aides. In order to ease the transfer process, transfer mode on the S-MMS controller 110B may be configured to automatically control any powered systems available on the S-MMS or via the motor controller 351. For example, for S-MMSs 18 that have powered, self-lifting arm rests, activation of the transfer mode may automatically raise the armrest that is directly adjacent to the selected transfer target. S-MMS 18 with active suspension systems may be configured to have the S-MMS controller 110B automatically lower or stiffen the suspension of the S-MMS 18 to assist in stability during the transfer. In some embodiments, S-MMSs 18 may include transfer assistance devices, such as extra grab bars or sliding support rails. When available, use of such features may be linked to the transfer mode being engaged, and their activation may be controlled by control signals sent from the S-MMS controller 110B.

Once a transfer is complete, the transfer mode may automatically reconfigure the seat to settings selected for transfer back into the S-MMS 18N. The S-MMS controller 110B may confirm that the transfer is complete by ensuring there is no user present. This may be accomplished by confirming that no weight or force is sensed on the S-MMS 18N based on user sensor reports 375 received by the SAC 302B, by tracking proximity of a paired wearable sensor in communication with the CNI 371, or any other means. A user may set the S-MMS 18N via the S-MMS controller 110B to lower the height of the seat to just below the height of the surface they are transferring from for ease of transferring back to the S-MMS 18N at a later time.

Approaching Objects and Furniture

For many MMS users, collision is a way of life. Tables, desks, chairs, and most of the objects in their daily life have been designed without them in mind. Even good drivers run into things, often damaging their MMS and their surroundings. What isn't often considered is the toll that this takes on users physically as they smash toes, knees, and fingers on the objects they run into.

It is not always enough for an S-MMS 18 safety system to behave in accordance with the spatial requirements of the S-MMS 18 itself and avoid hard collisions. In some embodiments, the S-MMS 18 may also take the user into consideration. As an example, positioning a mobile chair S-MMS 18 in front of a table requires the user to pull up to the right location (front-back) with high precision. This is often difficult with existing steering HMIs 352 like joysticks. In addition, since table heights differ, the user may have to position the S-MMS 18 seat vertically (up-down) to the right level as they approach the table. Often switching between positional control (front-back, left-right) and seat height control (up-down) requires multiple user button presses and actions via the HMI 352. If any of these directions are inaccurate, then the user's hands, fingers, or knees may run into the table. Even worse, often times they will get pinched between the table and the S-MMS 18. This is a simple example of existing conditions for many MMS users, and it ignores other user preference settings like seat back positioning which may be different for setting at a desk versus at a dinner table.

Figure 25:
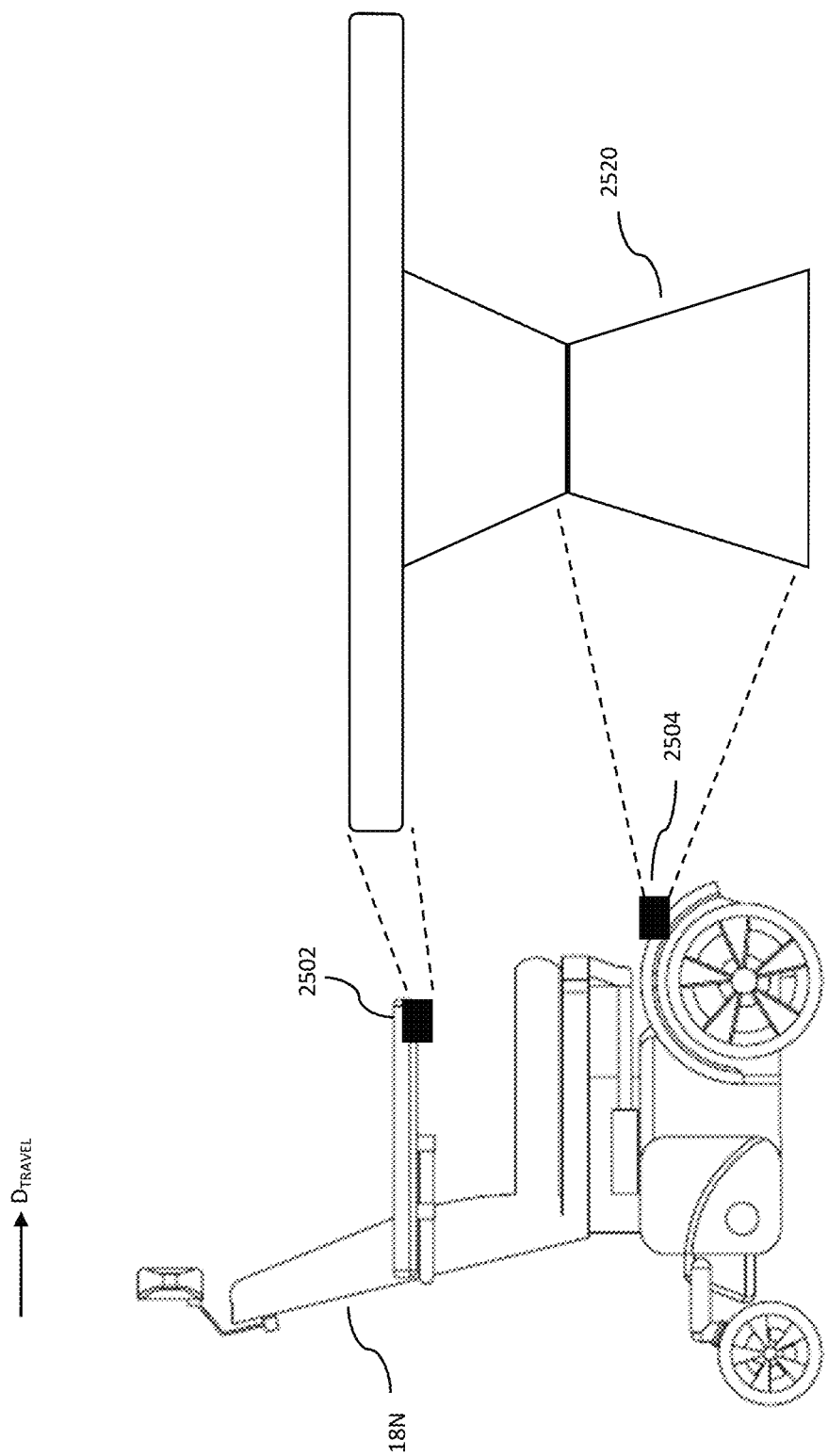
FIG. 25 depicts an embodiment of approach mode on an S-MMS.

An approach mode on an S-MMS 18 allows the user to get close enough to use or interact with common objects (e.g. desks, tables) as needed, but prevents injury of the user or damage to the object by preventing contact on both approach and exit of the S-MMS. This feature is illustrated in FIG. 25. As the mobile chair S-MMS 18N approaches a table, desk, bar, or other object with an overhang 2520, the situational awareness controller 302B of the S-MMS controller 110B detects the object 2520 based on one or more sensor reports 371-374 and positions the seat height to match the object height (generally per user history, general recommendations, and/or user preferences associated with a user profile stored in memory 120). This is unique from a typical collision avoidance system that would simply stop the S-MMS 18N user from approaching the table or other object 2520. For this reason, the user may need to activate the approach mode behavior either as an always on feature or per event via a voice command, gesture, or other HMI 352 input. This feature frees the user to focus on positioning the mobile chair S-MMS 18N close enough to the table or desk 2520 without worrying about injury.

For convenience, and because users will tend to use the same tables and desks or other objects 2520 often, the positioning system can be set to remember specific locations or types of objects as previously disclosed. As the S-MMS 18N approaches a known location or object type, the S-MMS controller 110B may auto adjust based on memory 120 without user intervention. The S-MMS controller 110B can remember both preferred seat settings and preferred front-back position to the object 2520 so that the S-MMS controller may automatically stop at the preferred spacing and adjust for comfort of the user. Approach mode may rely on a combination of sensors previously disclosed. Additionally or alternatively, additional sensors 2502 or 2504 may be utilized. In some embodiments, one or more sensor reports (e.g. 2502) may be provided to the S-MMS controller 110B by one or more sensors embedded in a pair smart device 1502.

In some embodiments, the S-MMS controller 110B may take into consideration both the extents of the S-MMS 18N and the location of the driver's knees, fingers, elbows, and other leading features (e.g. via data of those locations stored in memory and retrieved by the S-MMS controller, by sensors on the S-MMS placed at or focused on those locations as described herein and transmitting sensor reports of those locations to be used as inputs in the processes of the S-MMS controller, or otherwise). If a problem is detected by the user at any point, they can take over control of the S-MMS 18N. In some embodiments, a verbal command such as "stop" may halt the automated activity at any point in the process. To further safeguard the user, additional safety checks may be activated during approach maneuvers that are intended to sense and avoid soft impacts. Sensors on the seating system, or other locations, may sense if a force is detected in a place where force is not expected during a maneuver and pause the maneuver.

FIGS. 26A and 26B illustrate a non-limiting example placement of such sensors 2630 and 2660 to measure forces on the arm rest 2610 and foot rest 2640 of a mobile chair S-MMS 18N. In the event that a soft impact force F is detected, the S-MMS 18N may halt or slowly back away from the object being approached, which may impact one or more of those areas, and await further instructions from the user. Users may set preferences for how the S-MMS 18N should react in such situations. This functionality can also be linked to user health systems, such as electrodermal activity tracking devices or heart rate devices capable of sensing user pain if available and paired with the S-MMS 18N.

The approach mode may be further enhanced on S-MMSs 18 equipped with motorized accessories. As a non-limiting example, FIGS. 27A and 27B depict a self-retracting control unit 2710. The depicted example self-retracting unit 2710 moves out of the way automatically when the approach mode is engaged. In this example, a sensor on the self-retracting unit 2710 or a device attached to the self-retracting unit transmits one or more sensor reports to the S-MMS controller 110B. The S-MMS controller receives and processes the sensor reports from the self-retracting control unit 2710 to determine the self-retracting control unit will impact an object 2720 and transmits a control signal/command to the self-retracting control unit instructing the self-retracting control unit to retract. The self-retracting unit 2710 receives and processes the control signal/command from the S-MMS controller 110B and, in response thereto, retracts an arm or other member of the self-retracting unit. This keeps the user from having to manually reposition the unit in order to pull in close to a table or desk 2720. It also provides a clear indicator that the autonomous approach mode has been engaged. As a further benefit, the actuators used to move the unit may also be used to sense any unexpected forces that might indicate pinching or soft impacts enhancing the previously disclosed safety checks for approach mode.

Call and Send to Charge

An S-MMS 18 may be its user's access point for their entire world, both inside and outside the home. As a non-limiting example, a user of a mobile chair S-MMS requires their S-MMS to be within a certain proximity to transfer off and onto the S-MMS. Whenever the user is not on their S-MMS, it must be close by when the user wants to change locations, or the S-MMS must be brought to them by someone else. Not being in proximity to their S-MMS puts the user at risk if mobility is needed for safety reasons and degrades the quality of life and independence of the user if they cannot attend to their personal needs or desires because the location of the S-MMS does not allow transfer.

Due to the importance and frequency of transfers, a mobile chair S-MMS 18N may be programmed with the needed proximity to the user for a successful transfer (e.g. using the previously disclosed transfer mode functionality), which would allow the S-MMS to safely gain this proximity to a previously visited or preprogrammed location based on the previously disclosed auto-return functionality combined with precision navigation capabilities of the S-MMS controller 110B. Combining these functions, a user currently not in their S-MMS 18 may command their S-MMS to come to their location and park within the proximity required for transfer. These commands may come in many different ways, including voice, direct input, hand signal, or other methods of input through the HMI 352 or a paired smart device 1502.

The location of the user may be determined by the S-MMS 18 in a number of manners. The simplest manner being data stored in a memory 120 of the last time that the user was detected on the S-MMS 18 by the SAC 302B, e.g. based on user sensor reports 375. As a non-limiting example, weight sensors embedded in the seating system may add a waypoint to the S-MMS situational awareness map at the location that user weight is no longer detected in the seat. Additionally or alternatively, a location of the user may be determined based on the location of a wearable device or other device configured to transmit a beacon signal for detection by one or more communication processors 216 on the S-MMS 18. In an embodiment, the S-MMS controller 110 may use signal strength of the beacon to detect the user.

Managing the charge of battery powered S-MMSs 18 is critically important. The safety of the user relies on a fully functional S-MMS 18, which must be sufficiently charged to function as designed. FIG. 28A depicts a charging station 2802 located across a room from a bed 2804. In this example, the location of a charging station 2802 may not be within a safe proximity for the user to transfer to another location (e.g. the bed 2804) while the S-MMS 18N charges. In one embodiment, the location of the charge station 2802 has been marked by the user on their private map data 1702 stored on a remote server 1510 or onboard 120. Based on one or more of the navigation and location determination techniques previously disclosed, the S-MMS controller 110B navigation 363 function is aware of the S-MMS 18N current location and its proximity to the charging station 2802 and may control the S-MMS to travel to the charging station from the bed 2402 and/or to the bed from the charging station at a preset speed or an optional speed determined by input to the HMI 352 (e.g. by causing one or more commands to be sent from the S-MMS controller to the motor controller 351).

Figure 28B:
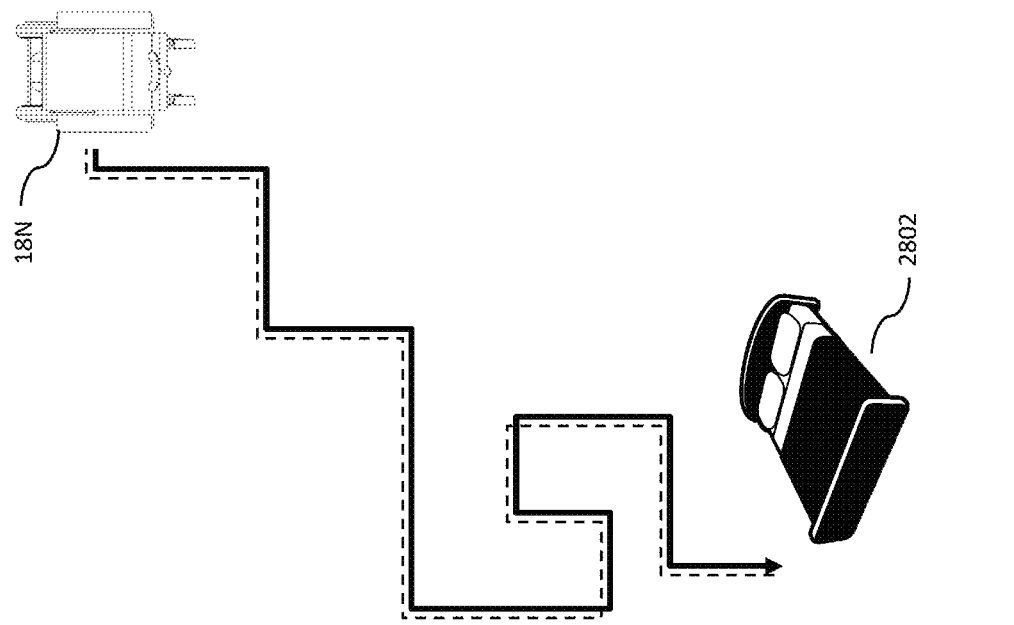
FIG. 28B depicts an S-MMS returning to the user.
Figure 28A:
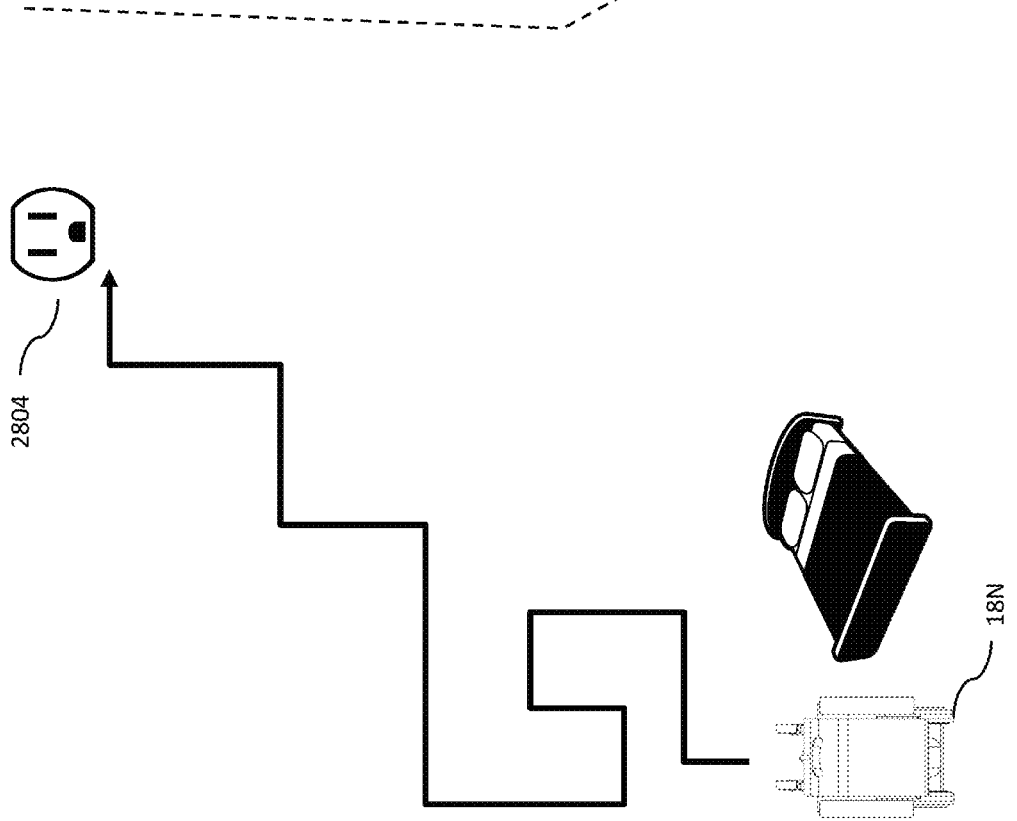
FIG. 28A depicts an S-MMS traveling to its charging station.

As illustrated in FIGS. 28A and 28B, the user may transfer to their bed 2804 at the end of the day and then command the S-MMS 18N to go to its charging station 2802 from its current location. In the morning, the user may command the S-MMS 18N to return to the bed 2804 within a proximity required to transfer back onto the S-MMS 18N. When paired with a wireless or robotic charging system, this functionality allows significant freedom and confidence for the user. These commands may be input using any one or more different methods, including voice, hand signal, or other methods of input through the HMI 352, paired smart device, wearable, and/or application 1502.

Avoiding People and Animals

The disclosed systems and methods allow an S-MMS 18 to avoid people and animals. Consider that motorized mobile systems often navigate and move in a distinct way, at a different speed, and occupy a very different footprint from the people or animals around them. This unique behavior, combined with the power and weight of a typical MMS, make awareness and avoidance of people, animals, and other things that move on their own important to the safety of both the S-MMS 18O user and those moving around it. As opposed to simply avoiding collisions with other automobiles in generally open environments like an automobile, the S-MMS 18O needs to watch for and avoid toes and tails, sometimes in tightly constrained spaces. S-MMS collision avoidance systems may be much more accurate than existing automobile systems. The disclosed SAC 302B (FIG. 5) combined with the dual mode variance techniques disclosed (FIG. 12) and careful attention to frames of reference and conversion error (FIG. 13) lay the foundation for collision avoidance with the required accuracy for an S-MMS 18.

S-MMSs 18 are often used in environments where people are in extremely close proximity. People can walk erratically and, when moving around an S-MMS, can be positioned where the user cannot see them or their toes. Depending on the abilities of the user, they may not have an awareness of those around them as they navigate their S-MMS 18 because of many factors, like a person who is moving quickly to pass them, is sitting, is short, is a child, or has moved from one side of the S-MMS to another. The disclosed SAC 302B with tactical manager 527 and threat assessor processes 528 (FIG. 5) enhance situational awareness of the user by creating and maintaining a situational awareness map that can then be used by the drive path manager 529 and alert manager 540.

In some embodiments, the S-MMS controller 110B is aware of people and animals (unique tracks) positioned or moving close by. The SAC 302B on the S-MMS controller 110B may recognize movement, and cause the motor controller 351 to react to that movement in the safest way possible, including slowing, stopping, or changing direction of the S-MMS 18. Additionally or alternatively, the user may be alerted via the HMI 352 of the location of people, animals, and objects positioned close by. As a non-limiting example, the SAC 302B on the S-MMS controller 110B may slow down the S-MMS 18 to protect individuals in the vicinity. Additionally or alternatively, the alert manager 540 of the SAC 302B may emit audible or visual warnings, using HMI 352 provisions such as lights and speakers, to those around the S-MMS 18 to make them aware that the device is within close proximity.

Wireless Identification

Figure 29:
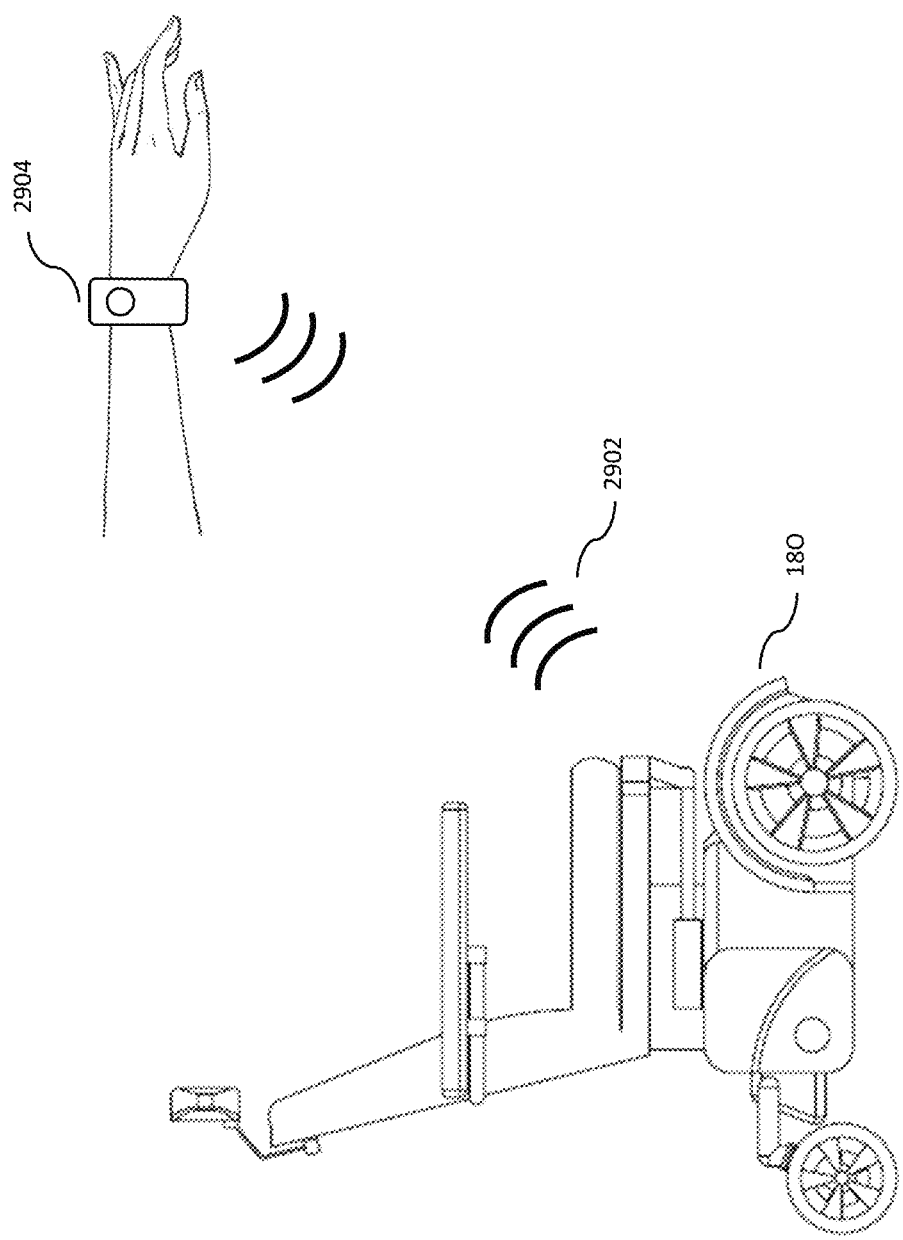
FIG. 29 depicts an embodiment in which a wearable device with an embedded transceiver communicates with an S-MMS.

FIG. 29 illustrates an embodiment of an S-MMS 18O in which a non-user (e.g. caregiver, service animal, technician, or other partner) may wear a wearable device 2904, such as a wrist band, necklace, ring or other accessory, with an embedded transceiver configured to communicate wirelessly 2902 with the S-MMS controller 110B. Additionally or alternatively, a caregiver or other individual may use their smart device (e.g. watch or smart phone) as the "accessory" if equipped with the proper transceiver and application. The wearable device 2904 transceiver may be configured to use one or more of the following means of communication 2902:

Active or passive RF,
Bluetooth,
IEEE 802.11 based Wi-Fi communication,
multiple low-rate wireless personal area networks (LR-WPANS) based on IEEE 802.15.4 including ZigBee, MiWi, and Wireless HART, or,
near field communications (NFC) protocol based on ISO/IEC 18092.

The applicable standards are herein incorporated by reference in their entirety.

As a non-limiting example, a caregiver, may wear a wrist band wearable 2904 with an embedded RF transceiver. The transceiver may be passive or active, with active transceivers allowing longer-range communication but requiring a power source, such as a battery. When the wrist band wearable 2904 comes within range of the S-MMS 18O, the signals 2902 from the wrist band are received by a communications processor 216 onboard the S-MMS 18O and the contents of the signal may be routed to the S-MMS controller 110B via a security processor or arbitrator 212. The detected presence of the wrist band wearable 2904 may cause the SAC 302B to operate uniquely.

Animal Partner Example

An S-MMS 18O may respond uniquely to individual people or animals and at a level of refinement not typically needed by existing autonomous systems. This may be accomplished by marking their tracks on the situational awareness map maintained by the SAC 302B and associating their track with unique threat assessor 528, drive path manager 529, or collision manager 526 behaviors on the SAC 302B (FIG. 5). As a non-limiting example, service animals are common companions to S-MMS 18 users. Socialization, interaction, and finding community can be challenging for those with limited mobility, and service animals many times provide companionship to those who use an S-MMSs. There are special training programs to prepare service animals to safely work around mobile chair MMSs. However, an S-MMS 18O may also be trained to work as a team with a service animal. In some embodiments, the S-MMS 18O recognizes its service animal partner and treats them differently than other animals or people. One example of this behavior may include the ability to for the S-MMS 18O to follow the service animal on command.

Figure 30:
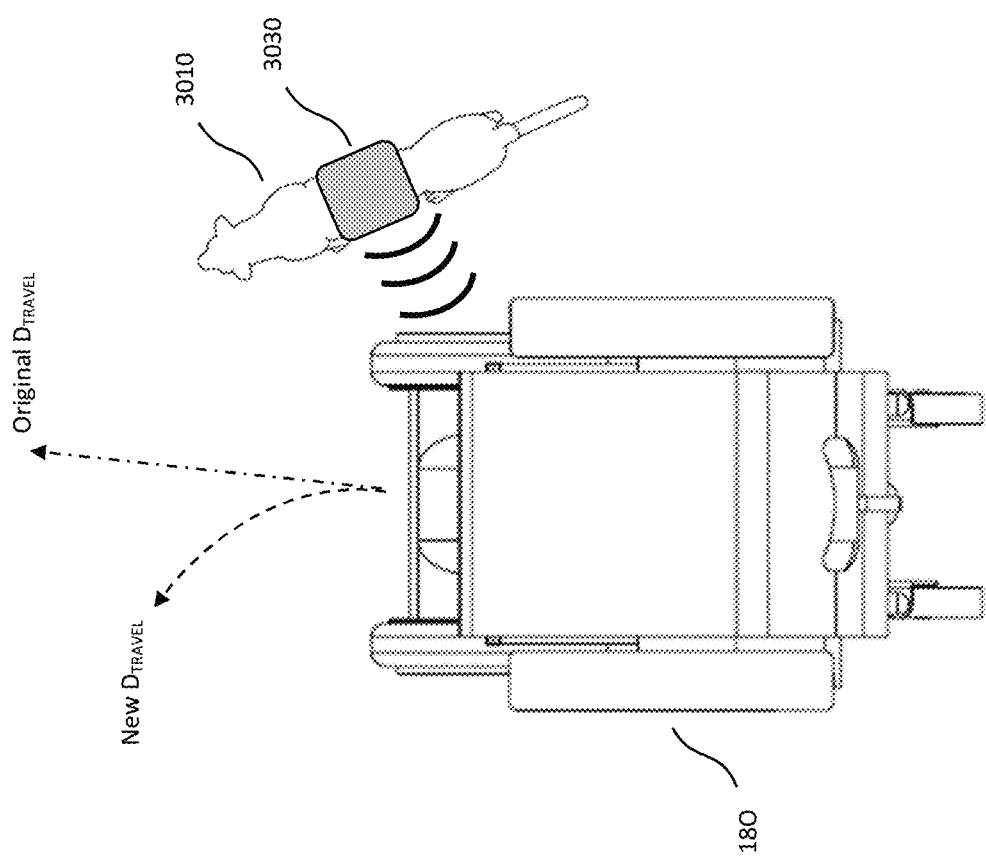
FIG. 30 depicts an example of a service animal "nudging" an S-MMS and redirecting it.

An example, illustrated in FIG. 30, is for the service animal 3010 to have the ability to "nudge" the mobile chair S-MMS 18O and redirect it by taking specific positions (say getting close to one side of the S-MMS 18O) while the user is driving. This behavior is unique and may only be engaged when a known service animal is recognized. Service animal control mode may be turned on or off by the user via the HMI 352, in some embodiments. In some embodiments, it is engaged automatically when the animal 3010 is in range. The S-MMS 18O may recognize the service animal by a special smart collar or addition to the service animals' vest 3030. The collar or vest 3030 may include a transponder or transceiver which uses one or more of the wireless protocols previously disclosed to transmit a signal to the S-MMS 18O. S-The MMS controller 110B receives and processes the signal to determine one or more actions are to be taken (e.g. move the S-MMS forward, backward, left, or right, or generate an alert for example) and transmits one or more control signals/commands to the motor controller 351, HMI 352, and/or other S-MMS 18O component as described herein to cause the one or more actions to be taken. Additionally or alternatively, the S-MMS controller 110B may use onboard cameras to recognize people and animals visually using on or more of the previously disclosed feature recognition approaches including use of badges or tags 2330 worn by the animal or individual 3010. In one embodiment, an S-MMS 18O receives a signal from an active RF transmitter embedded in a dog vest 3030 worn by the service animal 3010 via one or more communication processors 216 on the S-MMS 18O. The presence of the service animal signal is communicated to the SAC 302B via CNI 371 which causes the SAC 302B to task image sensors 520 on the S-MMS 18O to take 360-degree data. Feature extraction 530 is used to recognize a unique pattern (e.g. a QR code) on the animal's vest which has been pre-associated with that animal. When recognized, sensor track fusion 500 may associate the bearing location of the animal 3010 with range data received from other sensors (e.g. 371-373) and associate the track with the animal's unique identity code or flag. The tactical manager 527 may then place the identified track on the situational awareness map and the unique identity code may notify other functions (e.g. collision manager 536, drive path manager 529, threat assessor 528) to react to the individual track of the service animal 3010 using a unique, preconfigured, set of control instructions or rules. This same concept of unique behavior for unique individuals may extend to the way the S-MMS controller 110B reacts to specific caregivers, coworkers, trainers service animals, or other individuals. Unique behaviors may include, but are not limited to, allowing individuals to get closer to the S-MMS 18O before taking evasive action, following the individual, allowing the individual to nudge the direction of travel of the S-MMS 18O, or modification of any behavior of the motor controller 351 or HMI 352.

Turn and Look

Figure 31B:
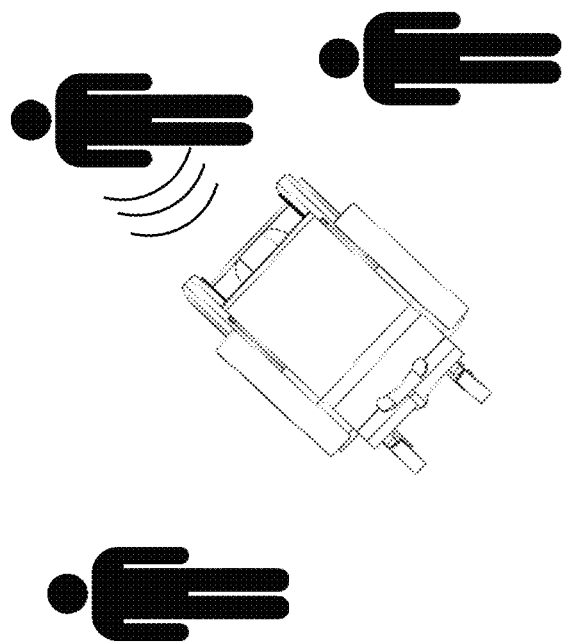
FIG. 31B depicts an S-MMS orienting a user to face individuals with whom the user is engaged.
Figure 31A:
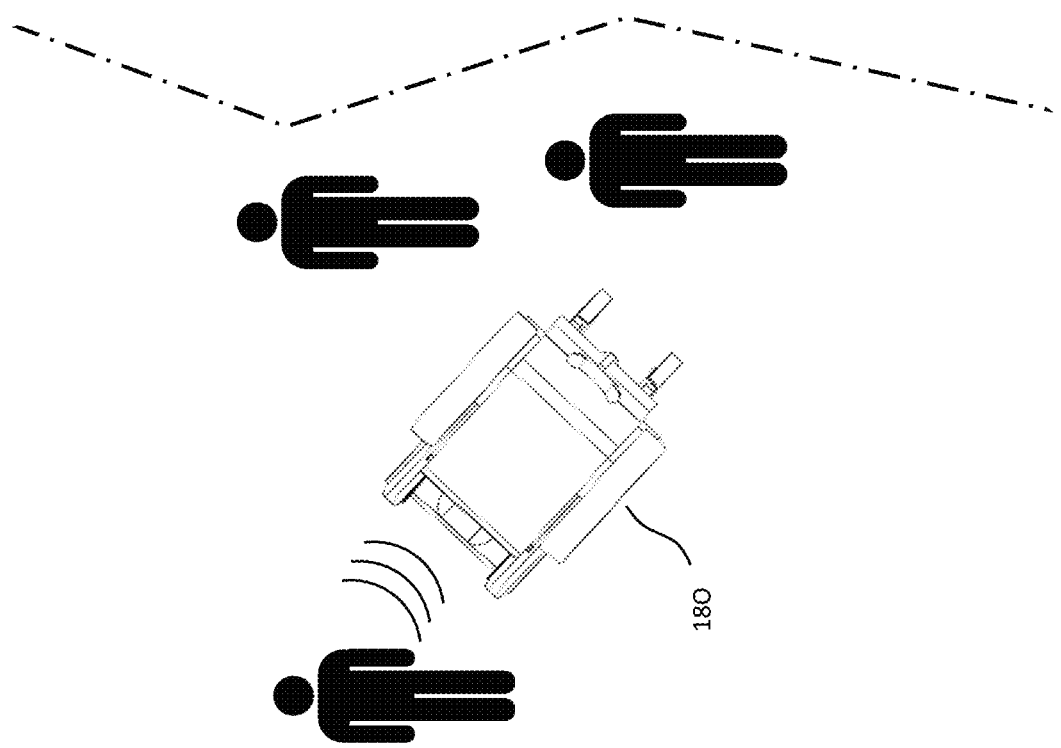
FIG. 31A depicts an S-MMS orienting a user to face individuals with whom the user is engaged.

For MMS users, social norms like maintaining eye contact and facing the speaker during conversations may not currently be possible without assistance or manually maneuvering their MMS. This not only distracts from engagement in the conversation, but may be a challenge for users who have diminished motor function or cognitive impairments that delay reactions. As illustrated in FIGS. 31A and 31B, the S-MMS controller 110B of an S-MMS 18O may assist user engagement when conversing and interacting by automatically orienting the user to face individuals with whom the user is engaged. The drive path manager 529 of the SAC 302B allows the S-MMS 18O to safely orient itself when in close proximity to people or objects. Moreover, in some embodiments (FIG. 5) the SAC 302B may have an accurate situational awareness map of those in the immediate vicinity, their location, and their relative position to where the S-MMS 18O (i.e. user) is facing. Turn and look functionality allows the S-MMS 18O to be directed to face different individuals with minimal or no effort on the part of the user.

When turn and look is enabled on the S-MMS controller 110B, the SAC 302B may use onboard cameras (e.g. image sensor reports 374) and microphones (e.g. non-contact sensor reports 373) to add information to the tracks of individual people, determining whether they are speaking, if they say any key words, and to locate their faces. In an embodiment, microphones associated with one or more onboard sonic sensors may be temporarily retasked to sample ambient noise. Additionally or alternatively, one or more dedicated microphone sensors may be added to the S-MMS 18O for use with this system. For example, the MMS controller 110B may receive and process a sensor report from a microphone to determine one or more actions are to be taken (e.g. move the S-MMS in a direction to face the front of the S-MMS toward the detected sound, for example) and transmit one or more control signals/commands to the motor controller 351 as described herein to cause the one or more actions to be taken. When combined with proximity and location information already identified with each individual's track on the situational awareness map maintained by the tactical manager 527, this allows enhancement of the existing situational awareness map of nearby individuals with information on their direction of interaction (which way they are facing).

In some embodiments, in its most basic form, the user may simply flick their HMI 352 input device (for example, a joystick) in the direction of an individual they wish to speak with and the S-MMS controller 110B will receive and process a signal from the HMI indicating the direction and reorient the S-MMS 18O to face the nearest individual in the chosen direction. HMI 352 input devices may include a series of buttons or a joystick that is used to select individuals to direct the user towards. Another type of user interface is a map of the recognized individuals to be displayed on the screen of a paired smart device 1502 so that the user can simply select the person they would like to speak with.

Turn to look mode may alternatively or additionally have an automatic setting, which with minimal or no input from the user automatically faces the S-MMS 18O towards an individual based on one or more predetermined criteria stored in memory 120. The S-MMS 18O may allow the use of onboard microphones to detect a person's name and automatically turn the user to face that person, in some embodiments. For example, the MMS controller 110B may receive and process a sensor report from a microphone to determine one or more actions are to be taken (e.g. move the S-MMS in a direction toward the detected name, for example) and transmit one or more control signals/commands to the motor controller 351 as described herein to cause the one or more actions to be taken. This behavior may be filtered by voice code so that, for example, the S-MMS controller 110B will react when a mother or father calls the name of a child in an S-MMS 18O but will not react similarly for anyone else.

Additionally or alternatively, the turn of turn and look functionality may be triggered by other signal sources such as light, sound, or wireless signals received from a certain direction. For any of these signal sources the signal may be recognized based on one or more of presence of the signal, signal frequency, sequence or pattern, or intensity.

Crowd Navigation

Navigating in a crowd is often particularly difficult in an MMS. Driving an MMS effectively lowers a user's field of view, making it difficult to see a destination past the crowd. This works both ways, so that the crowd perceives the MMS location as a hole in the crowd. Adding to the challenge of visibility as the crowd presses in, it can become extremely difficult to maneuver the MMS without colliding with or injuring nearby individuals. For MMS users, crowds can be both dangerous and intimidating. What is needed are novel methods to allow MMS users to confidently and safely visit crowded environments like sporting events, community events, and amusement parks.

The situational awareness controller 302B of the S-MMS controller 110B may assist in crowd navigation. The increased confidence in situational awareness provided by dual mode variance accuracy (FIG. 12) and the other navigation approaches disclosed herein are critical to the ability to operate and avoid collisions (e.g. collision manager 526) in a tightly constrained crowd situation. By providing real-time ground mapping and dynamic anti-tip features, the stability manager 525 allows S-MMS 18 users to focus on avoiding and following the crowd rather than worrying about safety. This somewhat reduces the cognitive load on the user. Furthermore, the stability manager 525 of the SAC 302B may allow users of S-MMSs 18 with significant seat lift or stand capability to drive confidently within bounds defined by the drive path manager 529 and enforced by the S-MMS controller 110B while elevated.

These things significantly aid the user, but do not fully solve the problem. At a certain crowd density, the S-MMS tactical manager 527 and or threat assessor 528 processes may become overwhelmed by the number of objects, or tracks, in the environment or the number of unique objects identified may be so close together as to effectively form one object. Additionally or alternatively, even in less dense crowds, an S-MMS user may want to simply follow along with the general flow of the crowd. For those reasons, a crowd following mode may be included in the S-MMS controller 110B. While this and other modes or functions disclosed are embodied as included on the S-MMS controller 110B, it is clear that these modes and functions may alternatively or additionally be deployed via an API 135 which communicates with the S-MMS controller and is hosted in one or more application spaces 125, 130.

Figure 32B:
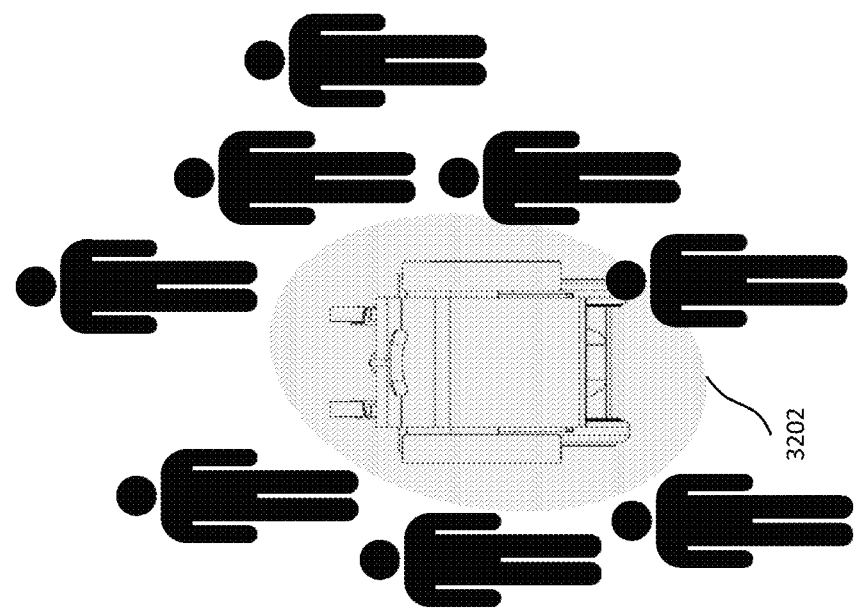
FIG. 32B depicts an example of crowd interaction with an S-MMS sensor system.
Figure 32A:
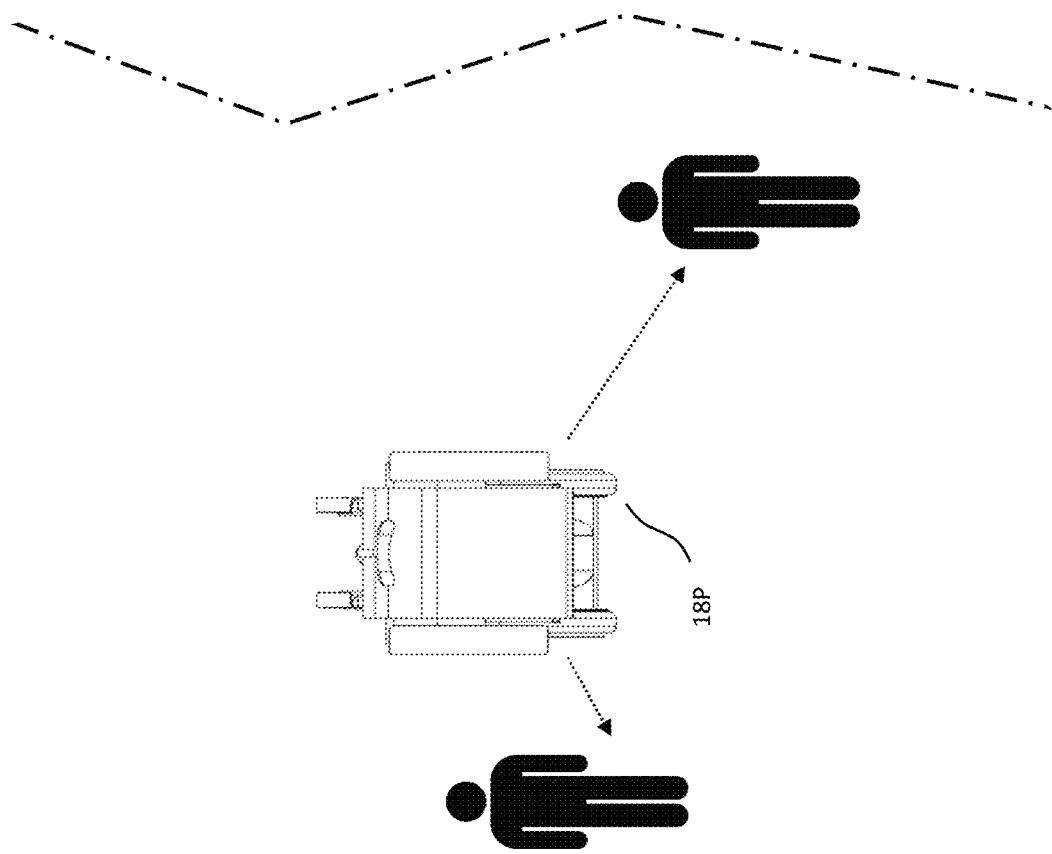
FIG. 32A depicts an example of crowd interaction with an S-MMS sensor system.

FIGS. 32A and 32B illustrate an example of crowd interaction with an S-MMS 18P. Crowd following mode, when enabled, may cause the tactical manager 527 of the SAC 302B to group multiple detected threats, or tracks, into zone reports with associated kinematic properties on the situational awareness map and create a map of "free space" 3202 around the S-MMS 18P. This map of free space 3202 may be incorporated as part of the situational awareness map or may be maintained as a separate entity. Crowd following mode may then cause the drive path manager 529 to engage an alternative set of flock based rules stored in memory 120. These rules may include one or more published flocking algorithms. Rather than trying to navigate to a specific location, the S-MMS controller 110B may use onboard sensors to follow the flow of people and keep the S-MMS 18P moving.

In one embodiment of flock based rules, the SAC 302B may establish and hold some basic rules. These may include matching the speed of the zone movement in front of the S-MMS 18P, maximize/equalize space between the S-MMS 18P and the free space on either side, or other published flocking algorithms. This mode may be triggered manually via the HMI 352 or a paired smart device 1502 or offered to the user when the tactical manager 527 or threat assessor 528 has determined that a significant number of tracks are being detected. An operator may choose to manually override the autonomous operations by the S-MMS controller 110B at any time, in some embodiments.

Figure 33:
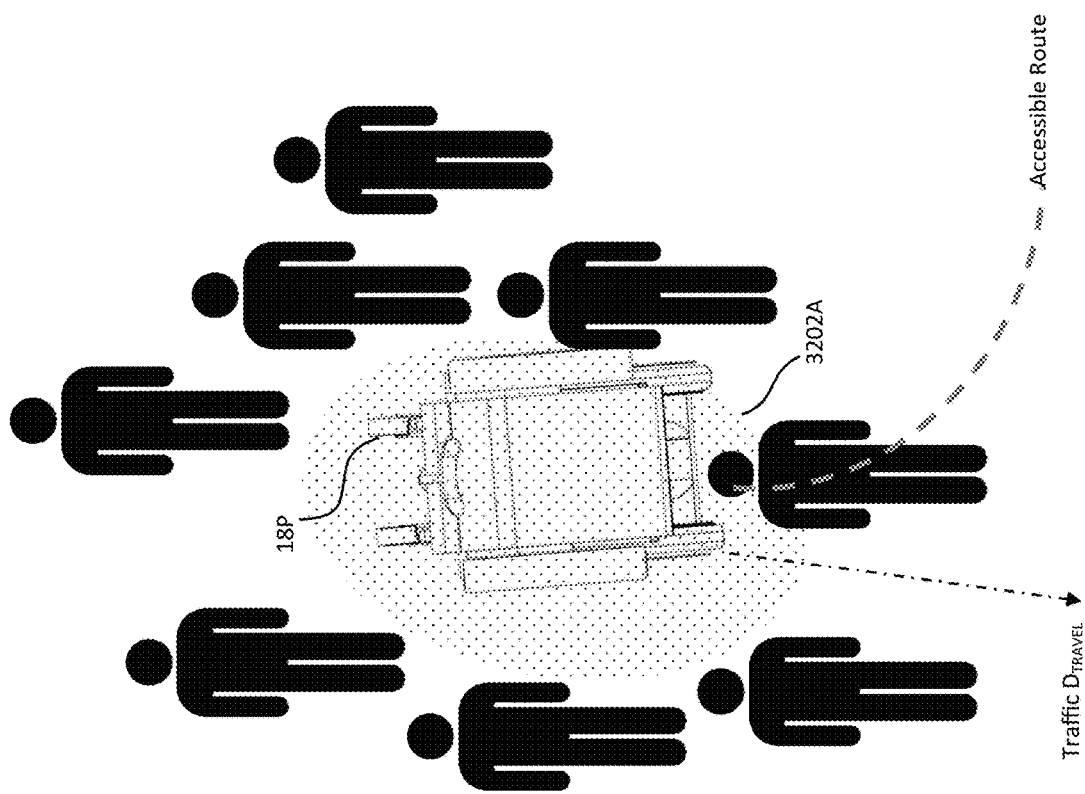
FIG. 33 depicts crowd navigation enhanced by integration of a navigation system.

FIG. 33 illustrates crowd navigation enhanced by integration of the previously disclosed best route system. Users may select both crowd following and location based navigation systems at the same time (e.g. via the HMI 352 or a paired smart device 1502) so that the S-MMS 18P may move towards a selected target location, along an accessible route, while navigating the flow of traffic in a crowd. As a non-limiting example, an S-MMS user may select a target end location for the S-MMS 18P to navigate to autonomously from a map on their paired smart device 1502 while the S-MMS 18P is surrounded by a moving crowd of people. This selection is communicated to the S-MMS controller 110B at which point the SAC 302B drive path manager 529, in coordination with navigation 363, determines the optimal accessible route (as illustrated in FIG. 33). Additionally, the tactical manager 527 recognizes that the user is surrounded by a moving crowd and alerts the drive path manager 529 and threat assessor 528 to switch to crowd navigation mode. Based on this, the drive path manager 529 may adjust its navigation approach. Rather than taking the ideal accessible route or following the direction of travel of the crowd (Traffic $D_{TRAVEL}$ in FIG. 33), the drive path manager 529 may cause motion across the main flow of traffic in a crowd by adjusting standard flocking rules. In an embodiment, the drive path manager 529 may cause one or more signals/commands to be transmitted to the motor controller 351 to cause the motor controller to engage the steering and drive of the S-MMS to drive on the edge of the detected free space 3202A in the direction of desired travel in order to create space in the crowd. In some embodiments, this edge following behavior may also be activated when the user inputs manual steering inputs into the HMI 352 while in crowd mode.

As a way to enhance the user experience, an amusement park or stadium may integrate their navigation, mapping, and crowd management systems with the S-MMS 18P through an API. This both enhances the user experience via a more accurate and easy way of finding information for destinations and enhances the facilities management by using S-MMSs 18P to provide real time crowd density and flow information.

Auto Queueing

Queuing can be another tedious task for MMS users. Parks, stadiums, and other facilities can simplify this process by providing auto-queuing guidance to S-MMSs 18, for example, through an application loaded in memory 120 and accessing the S-MMS controller 110B via an API 135. In some embodiments, the park may install special symbols such as a machine readable QR code, floor or wall markings, or a coded sequence of lights that instructs S-MMSs 18 as to how they should behave in a queue. In one embodiment, an S-MMS 18 equipped with one or more cameras may use feature extraction 530 on the SAC 302B to evaluate image sensor reports 374 for special symbols. When recognized by feature extraction 530, sensor track fusion 500 may alert the drive path manager 529 and cause the S-MMS controller 110B to send one or more control messages to the motor controller 351 and/or HMI 352 to cause the motor controller to engage the steering and drive of the S-MMS and/or cause the HMI to provide feedback or take another action. Additionally or alternatively, auto-queuing information may be transmitted wirelessly to the S-MMS using one or more of the previously disclosed methods, such as Bluetooth. This allows a user to cease manual operation while queuing and have the S-MMS controller 110B simply and automatically guide the S-MMS 18 through the queue (e.g. onto a ride or into a stadium). In some embodiments, S-MMSs 18 may be guided through queues by other wireless means, such as those disclosed for wireless ID of individuals and animals and or turn and look functions.

Figure 34:
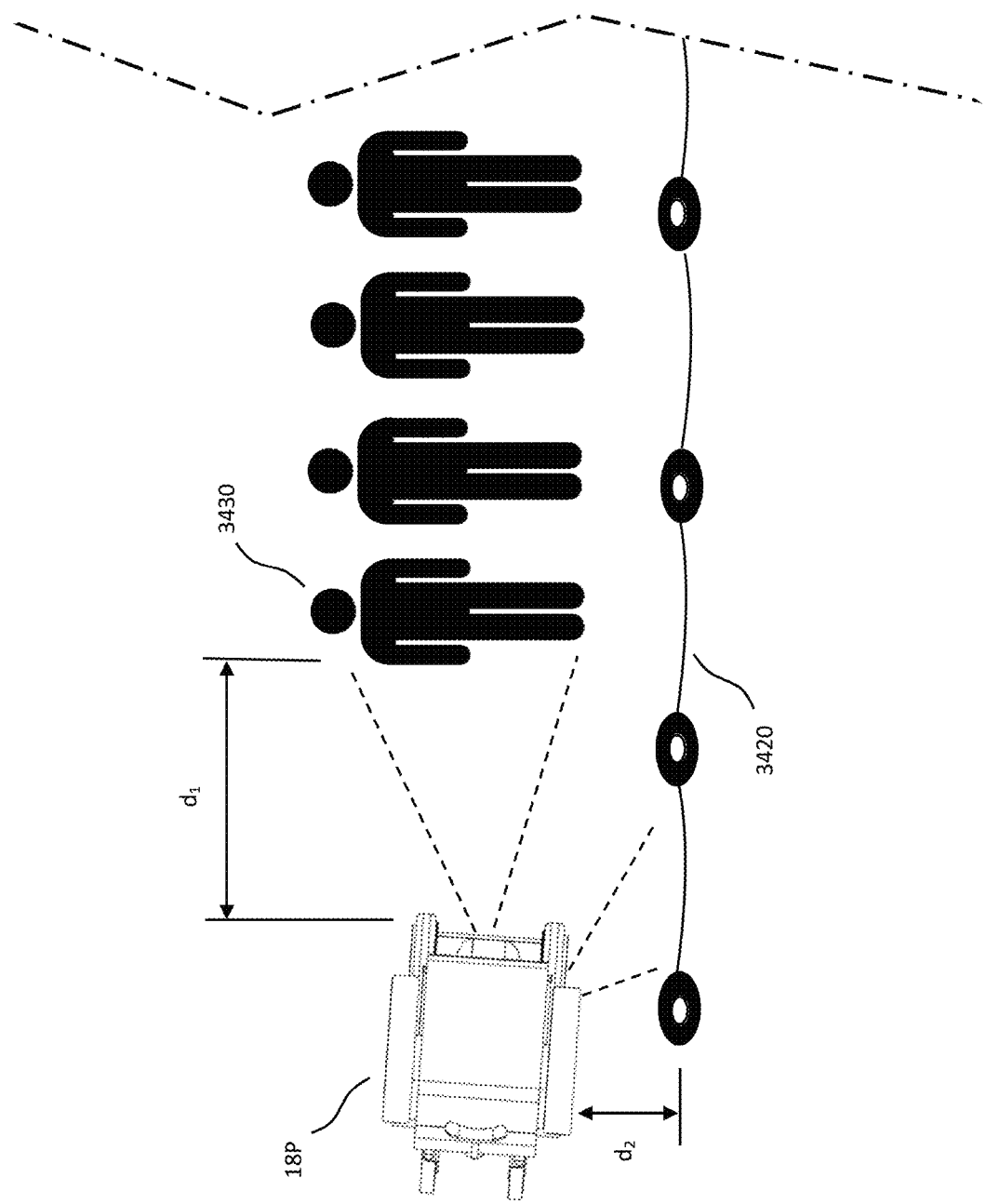
FIG. 34 depicts an embodiment of auto-queuing functionality.

For locations where auto-queuing as previously disclosed might not be available, the user may pull into a queue and then select a feature to follow a queue autonomously. FIG. 34 illustrates an embodiment of this functionality. In an example, many queues are separated by fabric lines 3420. In an embodiment, an S-MMS 18P user may select queuing mode via the HMI 352 or on a paired smart device 1502 when entering a queue. Via one or more of the input methods (for example using a touch screen on a paired smart device) the user may select the fabric line 3420 from an image. Based on their selection, the drive path manager 529 of the SAC 302B may combine a wall-following algorithm based on the selected reference with collision avoidance functionality (e.g. collision manager 526) which maintains a distance to $d_1$ to the next person in the queue 3410 and a distance $d_2$ to the divider 3420 to provide hands-free operation in a queue. The selected reference may be recognized by feature extraction 530 from image sensor reports 374 using one or more of published edge detection, feature recognition, and/or color recognition techniques.

In some embodiments, S-MMS users may be guided through a facility, queue, ride or other activity by augmented reality overlays (FIG. 21) provided by a facility so that navigation may still be partially or completely manually controlled by the user within one or more parameters.

Augmented, Situationally Aware Reality

The mobility MMSs enable freedom for their users. This freedom of choice, and the independence it enables, comes with a requirement of new skills and responsibilities. As an example, new users of an MMS now have control of a device that can cause injury to others, and they must develop new skills to operate the MMS safely. Users who struggle to develop the necessary control of their device may find it taken away or their freedom limited. New MMS users need training and encouragement to safely operate their systems.

In some embodiments, one or more cameras may be located on the S-MMS 18. These cameras may be used to provide the user with a view of the areas around and behind them (e.g. via a display that is also mounted on the S-MMS 18). In this example, image data is communicated to the S-MMS controller 110B, such as via a communication interface of the CNI 371, and the S-MMS controller 110B generates an image display via video or still images to the display. Alternately, one or more displays may be connected directly to one or more cameras. Moreover, based on ambient conditions, the image display may be filtered or otherwise modified by the S-MMS controller 110B for purposes of enhancing user situational awareness. Examples of such modification by the S-MMS controller 110B include filters that highlight contrasts, transitions in the image, and/or filters such as infrared filters to assist with night driving.

As previously disclosed (FIG. 21), the S-MMS 18 may be configured to pair with virtual reality (VR) or augmented reality (AR) systems. In one embodiment, this capability is used to provide safe, secure training. Training scenarios or programs may be either preprogrammed (e.g. included in memory 120 of the S-MMS 18) or downloaded to the device from one or more remote servers 1510 as desired. In some embodiments, these scenarios may utilize specific features and capabilities of the S-MMS controller 110B, motor controller 351 and/or HMI 352 accessed via an API 135. Data related to the training plan, progress, and level of the user may be stored in a secure memory 120 on the S-MMS 18 and on a secure memory on a remote server 1510 in some embodiments. Additionally, data associated with the user may be associated with a unique individual user profile. The training programs may allow unique behavior of S-MMS 18 controls while still maintaining and being subservient to the critical safety systems (e.g. collision avoidance 526 and stability management 525) of the SAC 302B.

A training simulation may involve working the controls (e.g. HMI 352) of the S-MMS 18 to complete exercises. In an embodiment, the game application may consist of game logic hosted on a complex application space 130 which is set up by a parent, or otherwise configured based on a desired goal. The S-MMS 18, in some scenarios in concert with an application running on a smart device 1502 and/or sensory device(s) such as a headset 2102, is guided by the user through an augmented or virtual world to achieve a desired outcome, training, or encouragement. In some embodiments, with an AR device 2102, a user could drive a course and collect virtual coins that they see in AR, or navigate to avoid virtual obstacles like cones, puddles, alligators, chairs, etc. that are projected on the real environment inside the AR device 2102. The S-MMS controller 110 may respond to virtual objects like it would those objects in the real world, allowing the user to learn safe proximity to objects in all directions. The training could progress in difficulty, allow users to achieve different levels, or encourage repeating exercises or training levels that are not successfully completed. In some embodiments, the achievement of levels or tasks in an augmented or virtual training simulation may unlock new real features, settings, or performance levels on the user's S-MMS. As a non-limiting example, the S-MMS 18 maximum speed may increase after completing a predefined number of levels.

In some embodiments, these or similar AR and VR programs may be used to periodically test a user's capabilities over time to analyze for any changes in their overall skill level, reaction time, and other metrics. This data may be very useful in analyzing changes in a user's overall health and ability especially, for instance, if the results of the tests degrade regularly over time. User result data may be stored and associated with an individual user profile and may be treated as ePHI.

AR may additionally or alternatively be used as a behavioral incentive system. S-MMS 18 users may be encouraged to navigate to locations by having a target set by another person or system. As a non-limiting example, if a parent 1544 wanted their child to drive an S-MMS 18 toward their van so they could go to school, the parent could set the van as the target either via a web interface 1542 or smart device 1532, and the user would see (via AR) a path to the van. The user could navigate, with the S-MMS controller 110B correcting back to the path determined by the drive path manager 529 of the SAC 302B with a predetermined amount of assistance, or no assistance, depending on settings and preferences. A score may be kept and rewards or feedback given during the trip or at the destination for levels of achievement based on how well the user controlled the S-MMS 18 compared to an ideal path as determined by the drive path manager 529.

These same or similar AR and VR capabilities may be utilized for general gaming. Socialization may be a challenge for MMS users. Inclusion, contribution, and community all derive from, or are reliant on, socialization of some kind. Games like Pokémon Go show that gaming outside the home is a real, powerful, communal activity. Gaming with an S-MMS 18 offers opportunities for S-MMS users and non-users to share in common activities in the same environment. However, location-based gaming relies on the accessibility of the location to the player. The SAC's 302B real-time understanding of the accessibility of the S-MMS gamer's surroundings allows a game hosted on the S-MMS 18 to modify gameplay so all game elements are available to the player within the accessible area proximate to the S-MMS. Accessibility awareness opens up the game to all users equally, ensuring complete inclusion in the game community.

While the safety systems of the disclosed S-MMS controller 110B maintain situational awareness of the surroundings, the user may have limited access to this awareness until a S-MMS controller action is triggered. Providing enhanced user awareness of potential accessibility or safety issues provides them with more information about their surroundings sooner.

Early awareness of potential stability, collision, and/or health issues helps the user grow in independence by relying less on the S-MMS controller 110B to intervene. In addition, it may allow users to create safer plans and more efficient manual navigation routes and maneuvers. Awareness may be delivered to the user in many ways via the HMI 352, including through voice assistants like Siri™, or as visual cues overlaid on the real world through AR. Paired AR equipment (FIG. 21) allows the display of visual warnings overlaid on the real environment. These warnings may take many forms, including highlighting or spotlighting dangerous conditions, displaying preferred paths, or displaying navigation instructions to a predetermined location. In one embodiment, paired AR glasses are used to display an overlay of the situational awareness map, maintained by the tactical manager 527 of the SAC 302B, onto the view directly in front of the user. Additionally or alternatively, one or more routes determined by the drive path manager 529 may be displayed on the AR glasses. A critical use is to provide information about unsafe conditions before the actual danger or condition is imminent. In some embodiments, only data deemed critical to the user (e.g. by threat assessor 528) is displayed. This may include the ability to reduce (rather than add) the amount of visibility and information available to the user. Additionally or alternatively, by accelerating the display of concerns, users who are driving fast S-MMSs 18 or those with cognitive impairments that delay reaction time would be able to better navigate.

In an embodiment, in concert with turn and look mode, connected wearables may be utilized to assist with navigation tasks. An example of this is the pairing of smart glasses such as Google Glass 2102 with an S-MMS 18M. When the user turns their head, the S-MMS controller 110B may automatically pivot the S-MMS 18M to match where the user is looking. While eventually items such as Google Glass may be common, many individuals may want a less conspicuous solution. For those users, the disclosed system may be configured work with "Navigation Accessories". These accessories may include things like baseball caps, hair ribbons, or other accessories with embedded IMU sensors and wireless transceivers that allow similar navigation functionality with discrete, stylish concealment.

To facilitate the understanding of the embodiments described herein, a number of terms are defined below. The terms defined herein have meanings as commonly understood by a person of ordinary skill in the relevant art. Terms such as "a," "an," and "the" are not intended to refer to only a singular entity, but rather include the general class of which a specific example may be used for illustration. The terminology herein is used to describe specific embodiments, but their usage does not delimit the disclosure, except as set forth in the claims.

The term "circuit" means at least either a single component or a multiplicity of components, either active and/or passive, that are coupled together to provide a desired function. Terms such as "wire," "wiring," "line," "signal," "conductor," and "bus" may be used to refer to any known structure, construction, arrangement, technique, method, and/or process for physically transferring a signal from one point in a circuit to another. Also, unless indicated otherwise from the context of its use herein, the terms "known," "fixed," "given," "certain", and "predetermined" generally refer to a value, quantity, parameter, constraint, condition, state, process, procedure, method, practice, or combination thereof that is, in theory, variable, but is typically set in advance and not varied thereafter when in use.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment.

Communication between various systems and devices is disclosed herein. Communication may occur using wired and/or wireless communication methods and protocols including, but not limited to, cellular, 802.11, Wi-Fi, 802.15, Bluetooth, 802.20, and WiMAX. NON-TRANSITORY COMPUTER READABLE MEDIUM The various operations of methods described above may be performed by any suitable means capable of performing the operations, such as various hardware and/or software component(s), circuits, and/or module(s).

The various illustrative logical blocks, modules, and circuits described in connection with the present disclosure may be implemented or performed with a hardware processor, a digital signal processor (DSP), an application specific integrated circuit (ASIC), a field programmable gate array signal (FPGA) or other programmable logic device (PLD), discrete gate or transistor logic, discrete hardware components, or combinations thereof designed to perform the functions described herein. A hardware processor may be a microprocessor, commercially available processor, controller, microcontroller, or state machine. A processor may also be implemented as a combination of two computing components, e.g., a combination of a DSP and a microprocessor, a plurality of microprocessors, one or more microprocessors in conjunction with a DSP core, or any other such configuration.

In one or more aspects, the functions described may be implemented in software, firmware, or any combination thereof executing on a hardware processor. If implemented in software, the functions may be stored as one or more executable instructions or code on a non-transitory computer-readable storage medium. A computer-readable storage media may be any available media that can be accessed by a processor. By way of example, and not limitation, such computer-readable storage media can comprise RAM, ROM, EEPROM, CD-ROM or other optical disk storage, magnetic disk storage or other magnetic storage devices, or any other medium that can be used to store executable instructions or other program code or data structures and that can be accessed by a processor. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Processes or steps described in one implementation can be suitably combined with steps of other described implementations.

Certain aspects of the present disclosure may comprise a computer program product for performing the operations presented herein. For example, such a computer program product may comprise a computer readable storage medium having instructions stored (and/or encoded) thereon, the instructions being executable by one or more processors to perform the operations described herein.

Software or instructions may be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a terminal and/or base station can obtain the various methods upon coupling or providing the storage means to the device.

For the sake of convenience, the operations are described as various interconnected functional blocks or distinct software modules. This is not necessary, however, and there may be cases where these functional blocks or modules are equivalently aggregated into a single logic device, program, or operation with unclear boundaries. In any event, the functional blocks and software modules or described features can be implemented by themselves or in combination with other operations in either hardware or software.

Having described and illustrated the principles of the systems, methods, processes, and/or apparatuses disclosed herein in a preferred embodiment thereof, it should be apparent that the systems, methods, processes, and/or apparatuses may be modified in arrangement and detail without departing from such principles. Claim is made to all modifications and variation coming within the spirit and scope of the following claims.

What is claimed is:

1. A method for a motorized mobile system (MMS) comprising:
   generating first sensor data about an object from a first sensor with respect to a first sensor reference frame, wherein the first sensor data about the object comprises a first range measurement to the object and a first bearing measurement to the object, the first range measurement having an associated first uncertainty, and the first bearing measurement having an associated second uncertainty;

generating second sensor data about the object from a second sensor with respect to a second sensor reference frame, wherein the second sensor data about the object comprises a second range measurement to the object and a second bearing measurement to the object, the second range measurement having an associated third uncertainty, and the second bearing measurement having an associated fourth uncertainty;

receiving, by a processor, the first and second sensor data;

responsive to receiving the first and second sensor data, matching, by the processor, the first and second sensor data by time;

responsive to matching the first and second sensor data by time, determining, by the processor, whether one or more of the matching first and second sensor data comprises polar coordinates;

responsive to determining one or more of the matching first and second sensor data comprises polar coordinates, converting, by the processor, the one or more matching first and second sensor data comprising polar coordinates to Cartesian coordinates;

translating, by the processor, the first sensor data from the first sensor reference frame to a Cartesian coordinate system of a motorized mobile system reference frame;

translating, by the processor, the second sensor data from the second sensor reference frame to the Cartesian coordinate system of the motorized mobile system reference frame;

selecting, by the processor, a lower range uncertainty between the first uncertainty and the third uncertainty;

selecting, by the processor, a lower bearing uncertainty between the second uncertainty and the fourth uncertainty; and combining, by the processor, the bearing measurement associated with the selected lower bearing uncertainty and the range measurement associated with the selected lower range uncertainty as a location of the object within a reduced area of uncertainty in the Cartesian coordinate system of the motorized mobile system reference frame.

2. The method of claim 1 wherein the processor uses the location of the object within the reduced area of uncertainty for at least one navigation operation.

3. The method of claim 1 wherein the processor uses the location of the object within the reduced area of uncertainty for obstacle avoidance.

4. The method of claim 1 wherein the processor identifies the location of the object within the reduced area of uncertainty on a situational awareness map.

5. The method of claim 1 wherein the first uncertainty is larger than the second uncertainty, and the fourth uncertainty is larger than the third uncertainty.

6. The method of claim 1 wherein the processor retrieves the first, second, third, and fourth uncertainties from a memory.

7. The method of claim 1 wherein uncertainty comprises known error in a physical measurement.

8. The method of claim 1 wherein the motorized mobile system is selected as a mobile chair, a mobility scooter, an electronic conveyance vehicle, a riding lawn mower, a grocery cart, an all-terrain vehicle, an off-road vehicle, or a golf cart.

9. The method of claim 1 wherein the object comprises at least one of a physical thing, a person, an animal, a ground feature, and a surface condition.

10. The method of claim 1 wherein the first sensor is selected as at least one of an optical sensor, a sound sensor, a hall effect sensor, a proximity sensor, a radar sensor, a sonar sensor, an ultrasonic sensor, a LIDAR sensor, and a camera capable of distance detection.

11. The method of claim 1 wherein the second sensor is selected as at least one of an optical sensor, a sound sensor, a hall effect sensor, a proximity sensor, a radar sensor, a sonar sensor, an ultrasonic sensor, a LIDAR sensor, and a camera capable of distance detection.

12. The method of claim 1 wherein the first sensor determines the first range measurement as a distance to the object from a point of operation of the first sensor.

13. The method of claim 1 wherein the first sensor determines the first bearing measurement as a direction to the object from a point of operation of the first sensor.

14. The method of claim 13 wherein the direction to the object is expressed in degrees offset from a true baseline direction.

15. The method of claim 1 wherein the second sensor determines the second range measurement as a distance to the object from a point of operation of the second sensor.

16. The method of claim 1 wherein the second sensor determines the second bearing measurement as a direction to the object from a point of operation of the first sensor.

17. The method of claim 16 wherein the direction to the object is expressed in degrees offset from a true baseline direction.

18. The method of claim 1 wherein the processor processes the first uncertainty as a parameter, associated with a result of the first range measurement, that characterizes a dispersion of values that could reasonably be attributed to the first range measurement.

19. The method of claim 1, wherein the processor processes the second uncertainty as a parameter, associated with a result of the first bearing measurement, that characterizes a dispersion of values that could reasonably be attributed to the first bearing measurement.

20. The method of claim 19 wherein the target is selected as at least one of an optical target, a retro-reflective target, a graphic, a sticker, and a decal.

21. The method of claim 1 wherein the processor processes the third uncertainty as a parameter, associated with a result of the second range measurement, that characterizes a dispersion of values that could reasonably be attributed to the second range measurement.

22. The method of claim 1, wherein the processor processes the fourth uncertainty as a parameter, associated with a result of the second bearing measurement, that characterizes a dispersion of values that could reasonably be attributed to the second bearing measurement.

23. The method of claim 22 wherein the target is selected as at least one of an optical target, a retro-reflective target, a graphic, a pattern, a sticker, and a decal.

24. The method of claim 1 wherein at least one of the first and second sensors is located on a vehicle other than the motorized mobile system, and the processor receives data about the object from the at least one of the first and second sensors located on the vehicle other than the motorized mobile system.

25. The method of claim 1 wherein a target is associated with the object, and the first sensor measures a range and a bearing to the target associated with the object, generates the range to the target as the first range measurement to the object, and generates the bearing to the target as the first bearing measurement to the object.

26. The method of claim 1 wherein a target is associated with the object, and the second sensor measures a range and a bearing to the target associated with the object, generates the range to the target as the second range measurement to the object, and generates the bearing to the target as the second bearing measurement to the object.

27. The method of claim 1 wherein the processor converts the one or more matching first and second sensor data comprising polar coordinates to Cartesian coordinates using a standard conversion comprising:

$$x_m = r_m \cos \theta_m \text{ and } y_m = r_m \sin \theta_m, \quad \text{Eq. 1}$$

wherein $r_m$ is a range to the object in a polar coordinate system, $\theta_m$ is a bearing of the object in the polar coordinate system, $x_m$ is a range coordinate of the object in the Cartesian coordinate system of the motorized mobile system reference frame, and $y_m$ is a bearing coordinate of the object in the Cartesian coordinate system of the motorized mobile system reference frame.

28. The method of claim 1 further comprising providing one or more of orientation, attitude, and heading to the processor by an inertial measurement unit, wherein the processor uses the one or more of orientation, attitude, and heading to convert the one or more matching first and second sensor data comprising polar coordinates to the Cartesian coordinates.

29. A method for a motorized mobile system (MMS) comprising:

generating first sensor data about an object from a first sensor with respect to a first sensor reference frame, the object located proximate to the motorized mobile system, wherein the first sensor data about the object comprises a first range measurement to the object and a first bearing measurement to the object, the first range measurement having an associated first uncertainty, and the first bearing measurement having an associated second uncertainty;

generating second sensor data about the object from a second sensor with respect to a second sensor reference frame, the object located proximate to the motorized mobile system, wherein the second sensor data about the object comprises a second range measurement to the object and a second bearing measurement to the object, the second range measurement having an associated third uncertainty, and the second bearing measurement having an associated fourth uncertainty;

receiving, by a processor, the first and second sensor data;

responsive to receiving the first and second sensor data, matching, by the processor, the first and second sensor data by time;

responsive to matching the first and second sensor data by time, determining, by the processor, whether one or more of the matching first and second sensor data comprises polar coordinates;

responsive to determining one or more of the matching first and second sensor data comprises polar coordinates, converting, by the processor, the one or more matching first and second sensor data comprising polar coordinates to Cartesian coordinates;

translating, by the processor, the first sensor data from the first sensor reference frame to a Cartesian coordinate system of a motorized mobile system reference frame;

translating, by the processor, the second sensor data from the second sensor reference frame to the Cartesian coordinate system of the motorized mobile system reference frame;

selecting, by the processor, a lower range uncertainty between the first uncertainty and the third uncertainty;

selecting, by the processor, a lower bearing uncertainty between the second uncertainty and the fourth uncertainty; and combining, by the processor, the bearing measurement associated with the selected lower bearing uncertainty and the range measurement associated with the selected lower range uncertainty as a location of the object within a reduced area of uncertainty in the Cartesian coordinate system of the motorized mobile system reference frame.

* * * * *